(12) United States Patent
Hatakeyama et al.

(10) Patent No.: US 11,453,741 B2
(45) Date of Patent: Sep. 27, 2022

(54) STRETCHABLE FILM AND METHOD FOR FORMING THE SAME

(71) Applicant: SHIN-ETSU CHEMICAL CO., LTD., Tokyo (JP)

(72) Inventors: Jun Hatakeyama, Joetsu (JP); Motoaki Iwabuchi, Joetsu (JP); Joe Ikeda, Joetsu (JP); Shiori Nonaka, Joetsu (JP); Koji Hasegawa, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 497 days.

(21) Appl. No.: 16/514,068

(22) Filed: Jul. 17, 2019

(65) Prior Publication Data

US 2020/0040125 A1    Feb. 6, 2020

(30) Foreign Application Priority Data

Aug. 2, 2018    (JP) .............................. JP2018-146265

(51) Int. Cl.
| | |
|---|---|
| *C14C 11/00* | (2006.01) |
| *C08G 18/32* | (2006.01) |
| *C08L 75/16* | (2006.01) |
| *C08J 5/18* | (2006.01) |
| *A61B 5/25* | (2021.01) |

(52) U.S. Cl.
CPC ............ *C08G 18/3206* (2013.01); *A61B 5/25* (2021.01); *C08J 5/18* (2013.01); *C08L 75/16* (2013.01); *C08L 2203/16* (2013.01); *C08L 2203/202* (2013.01)

(58) Field of Classification Search
CPC ............ C08G 18/3812; C08G 18/5015; C08G 18/6275; C08G 18/3839; C08G 18/61; C08G 18/672; C08G 18/8175; C08L 75/16
See application file for complete search history.

(56) References Cited

U.S. PATENT DOCUMENTS 5,128,434 A * 7/1992 Lai .................. G02B 1/043
528/65
5,760,100 A * 6/1998 Nicolson ............ C08G 18/4833
528/33

(Continued)

FOREIGN PATENT DOCUMENTS

| EP | 3354670 A1 | 8/2018 |
|---|---|---|
| JP | 2583412 B2 | 2/1997 |

(Continued)

OTHER PUBLICATIONS

Dec. 4, 2019 Extended European Search Report issued in European Patent Application No. 19189849.3.

(Continued)

*Primary Examiner* — Michael M Dollinger
(74) *Attorney, Agent, or Firm* — Oliff PLC

(57) ABSTRACT

The present invention is a stretchable film of a cured product of a resin including: a polymer compound having a urethane bond in the main chain, a repeating unit containing a fluorine atom, and a repeating unit containing a silicon atom. The present invention provides a stretchable film that has excellent stretchability and strength, with the film surface having excellent water repellency, and a method for forming the same.

10 Claims, 6 Drawing Sheets

(56) References Cited

U.S. PATENT DOCUMENTS

| | | | | |
|---|---|---|---|---|
| 5,789,461 | A | * | 8/1998 | Nicolson ................ B29C 39/42 |
| | | | | 528/33 |
| 5,945,498 | A | * | 8/1999 | Hopken ............. C08G 18/4833 |
| | | | | 528/42 |
| 6,313,335 | B1 | * | 11/2001 | Roberts ............. C08G 18/0823 |
| | | | | 524/588 |
| 6,673,889 | B1 | * | 1/2004 | Weinert ............... C08G 18/672 |
| | | | | 560/158 |
| 10,501,585 | B2 | * | 12/2019 | Hatakeyama ...... C08G 18/7893 |
| 10,696,779 | B2 | * | 6/2020 | Hatakeyama .............. C08J 5/18 |
| 10,717,804 | B2 | * | 7/2020 | Hatakeyama ........ C07F 7/0879 |
| 10,800,916 | B2 | * | 10/2020 | Hatakeyama .............. C08J 5/18 |
| 11,078,317 | B2 | * | 8/2021 | Hatakeyama .......... C08G 18/44 |
| 2001/0034413 | A1 | | 10/2001 | Hanada et al. |
| 2005/0164010 | A1 | * | 7/2005 | Trombetta ......... C08G 18/6692 |
| | | | | 525/406 |
| 2012/0249995 | A1 | | 10/2012 | Hatakeyama et al. |
| 2015/0004406 | A1 | | 1/2015 | Suzuki et al. |
| 2015/0368453 | A1 | * | 12/2015 | Wada ...................... G03F 7/027 |
| | | | | 522/42 |
| 2018/0094164 | A1 | | 4/2018 | Ito et al. |
| 2018/0134860 | A1 | | 5/2018 | Hatakeyama et al. |
| 2018/0194941 | A1 | * | 7/2018 | Kurtoglu ............. C08G 18/3206 |
| 2018/0215876 | A1 | | 8/2018 | Hatakeyama et al. |
| 2020/0040125 | A1 | * | 2/2020 | Hatakeyama ...... C08G 18/3893 |

FOREIGN PATENT DOCUMENTS

| | | |
|---|---|---|
| JP | 2624060 B2 | 6/1997 |
| JP | H11-502894 A | 3/1999 |
| JP | 2001-329038 A | 11/2001 |
| JP | 2001-524558 A | 12/2001 |
| JP | 2004-033468 A | 2/2004 |
| JP | 2007-077359 A | 3/2007 |
| JP | 2007-140446 A | 6/2007 |
| JP | 2011-194757 A | 10/2011 |
| JP | 2012-152725 A | 8/2012 |
| JP | 2013-139534 A | 7/2013 |
| JP | 2018-053193 A | 4/2018 |
| JP | 2018-083935 A | 5/2018 |
| WO | 2014/104074 A1 | 7/2014 |

OTHER PUBLICATIONS

Mar. 27, 2021 Office Action issued in Korean Patent Application No. 10-2019-0093756.

Murase, Heihachi et al., "Characterization of Molecular Interfaces in Hydrophobic Systems", Progress in Organic Coatings, 1997, vol. 31, pp. 97-104.

May 31, 2022 Office Action issued in Japanese Application No. 2019-124324.

* cited by examiner

STRETCHABLE FILM AND METHOD FOR FORMING THE SAME

TECHNICAL FIELD

The present invention relates to a stretchable film that combines stretchability, strength, and water repellency, together with a method for forming the same.

BACKGROUND ART

A recent growing popularity of Internet of Things (IoT) has accelerated the development of such major wearable devices as watches and glasses that allow for Internet access. Even in the fields of medicine and sports, wearable devices for constantly monitoring the user's physical state are increasingly demanded, and such technological development is expected to be further encouraged.

One typical wearable device is attached to the human body of users or attached to a cloth that is in directly contact with the body to constantly monitor the state of physical conditions. The wearable device normally includes a bio-electrode for detecting an electric signal transmitted from a body, wires for sending the electric signal to a sensor, a semiconductor chip serving as a sensor, and a battery, as well as an adhesive pad to be attached to the skin. Patent Document 1 describes detailed structures of a bio-electrode, a wiring part surrounding the bio-electrode, and an adhesive pad. The wearable device disclosed in Patent Document 1 includes a bio-electrode, a silicone-based adhesive film disposed around the bio-electrode, a sensor device, and a meandering-shaped stretchable silver wiring part coated with a stretchable urethane film between the bio-electrode and the sensor device.

The urethane film has high stretchability and strength, and excellent mechanical properties as a film coated on a stretchable wiring part. Unfortunately, the hydrolysis inherent in the urethane film lowers its strength and stretchability, while the silicone film has no such hydrolysis, but the strength inherently remains low.

The use of silicone urethane polymers, whose main chain has both a urethane bond and a siloxane bond, has been examined. Advantageously, cured products of the silicone urethane polymer are characterized by higher strength than single silicone and lower hydrolysis than single polyurethane. Such cured products unfortunately fail to achieve the strength and stretchability equivalent to single polyurethane and the water repellency equivalent to single silicone, and the strength and water repellency are in-betweens of those inherent in silicone and polyurethane.

On the other hand, blended materials of polyurethane and silicone have been investigated. For Example, Patent Documents 2 and 3 describe materials in which non-reactive silicone and crosslinkable polyurethane have been blended. In films formed from these materials, the silicone rises to the film surface of cured polyurethane (bleed out) to improve the water repellency of the film surface. The silicone is not crosslinked, however, and tends to come off from the film surface to lower the water repellency thereby. The silicone does not rise to the film surface without the surface, thereby failing to improve the water repellency of a laminate that is compression molded with sheets on both sides of the film.

Diol materials have been proposed to synthesize polyurethane having a siloxane in the side chain. Patent Documents 4 and 5 show diol compounds to form polyurethane having a siloxane in the side chain.

Polyurethane compounds having a fluorinated alkylene group in the main chain have been proposed. Making good use of the releasability of a fluorinated alkylene group, urethane acrylate has been proposed as a component of materials for nanoimprinting lithography (Patent Document 6). Having high water repellency, fluorinated alkylene groups are used for applications that require water repellency, so with silicone urethane.

In the interactions between a water molecule and a methyl group or a trifluoromethyl group, it has been reported that a methyl group orients to the oxygen atom of a water molecule, and a trifluoromethyl group orients to the hydrogen atom of a water molecule. The distances across the orientation are indicated that the distance between water and a methyl group is longer than the distance between water and a trifluoromethyl group (Non-Patent Document 1). It is conceived that longer distance across the orientation of water and resin makes the interaction with water smaller and water slip on the resin surface higher. In resist protective coat for liquid immersion lithography, it has been reported that the combination of a fluoroalkyl group and an alkyl group makes the distance across an orientation still longer than in the cases of using each one of a fluoroalkyl group and an alkyl group, thereby making it possible to improve the water slip of resin remarkably. (Patent Document 7).

CITATION LIST

Patent Literature

Patent Document 1: Japanese Patent Laid-Open Publication No. 2004-033468
Patent Document 2: Japanese Patent Laid-Open Publication No. 2011-194757
Patent Document 3: Japanese Patent Laid-Open Publication No. 2013-139534
Patent Document 4: Japanese Patent No. 2583412
Patent Document 5: Japanese Patent No. 2624060
Patent Document 6: International Patent Laid-Open Publication No. WO 2014/104074
Patent Document 7: Japanese Patent Laid-Open Publication No. 2007-140446

Non Patent Literature

Non Patent Document 1: Progress in Organic Coatings, 31, p 97-104 (1997)

SUMMARY OF THE INVENTION

Technical Problem

Due to these backgrounds, it has been demanded to develop a stretchable film having excellent stretchability and strength that are equivalent to those of polyurethane as well as higher water repellency, and a method for forming the same.

In view of the circumstances, the present invention aims to provide a stretchable film that is excellent in stretchability, strength, and water repellency on the film surface as well as a method for forming the same.

Solution to Problem

To solve the issues described above, the present invention provides a stretchable film of a cured product of a resin comprising a polymer compound having a urethane bond in a main chain thereof, a repeating unit containing a fluorine atom, and a repeating unit containing a silicon atom.

The inventive stretchable film is excellent in stretchability and strength as well as water repellency on the film surface.

In this case, the repeating unit containing a silicon atom preferably has the silicon atom in the side chain.

The stretchable film like this is quite excellent in stretchability and strength as well as water repellency on the film surface.

In the stretchable film, the repeating unit containing a fluorine atom preferably has the fluorine atom in the side chain.

The stretchable film like this is particularly excellent in stretchability and strength as well as water repellency on the film surface.

In the stretchable film of the present invention, the polymer compound preferably has a structure shown by the following general formula (1):

(1)

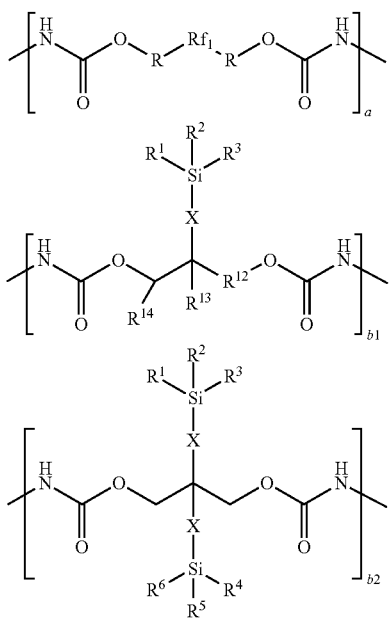

wherein $R^1$, $R^2$, $R^3$, $R^4$, $R^5$, and $R^6$ each represent a linear, branched, or cyclic alkyl group having 1 to 6 carbon atoms, a phenyl group, a 3,3,3-trifluoropropyl group, or a $-(OSiR^7R^8)_n-OSiR^9R^{10}R^{11}$ group; $R^7$, $R^8$, $R^9$, $R^{10}$, and $R^{11}$ each have the same meaning as $R^1$ to $R^6$; each R independently represents a single bond or a methylene group; "n" represents a number in a range of 0 to 100; $R^{12}$ represents a single bond, a methylene group, or an ethylene group; $R^{13}$ represents a hydrogen atom or a linear alkyl group having 1 to 4 carbon atoms; $R^{14}$ represents a hydrogen atom or a methyl group; X represents a linear or branched alkylene group having 3 to 7 carbon atoms, optionally containing an ether group; $Rf_1$ represents a linear or branched alkylene group having 1 to 200 carbon atoms and at least one fluorine atom, optionally containing an ether group; and "a", "b1", and "b2" are each number of units in the structure and are integers in ranges of $1 \leq a \leq 20$, $0 \leq b1 \leq 20$, $0 \leq b2 \leq 20$, and $1 \leq b1+b2 \leq 20$.

The stretchable film like this is excellent in stretchability and strength, together with having very high water repellency, because the polymer compound has a polyurethane structure that contains both of a repeating unit of urethane having a fluoroalkyl group or a fluoroalkylene group and a repeating unit of urethane having a siloxane chain in the side chain.

In this case, the polymer compound is preferably a reaction product of a diol compound and a compound having an isocyanate group, and the diol compound contains a diol compound Ma as well as a diol compound Mb1 and/or a diol compound Mb2 shown by the following general formulae (2):

(2)

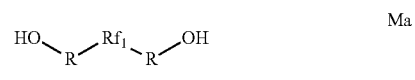
Ma

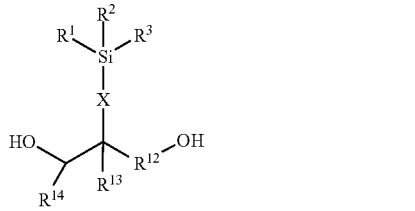
Mb1

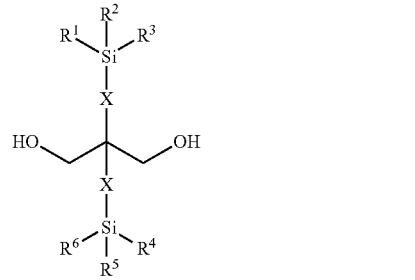
Mb2 wherein $R^1$ to $R^4$, X, $Rf_1$, and R are as defined above.

The stretchable film like this is quite excellent in stretchability and strength as well as water repellency on the film surface.

In the stretchable film of the present invention, the polymer compound is preferably a compound having a (meth)acrylate group at the terminal, shown by the following general formula (3):

(3)

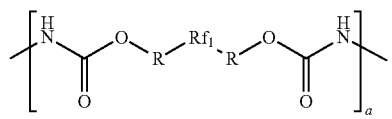

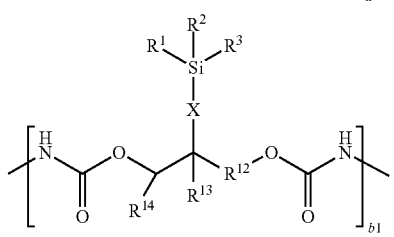

-continued

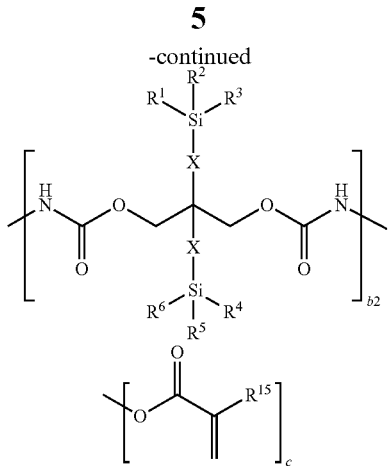

wherein $R^1$ to $R^{14}$, X, $Rf_1$, and R are as defined above; $R^{15}$ represents a hydrogen atom or a methyl group; and "a", "b1", "b2", and "c" are each number of units in one molecule and are in ranges of $1 \le a \le 20$, $0 \le b1 \le 20$, $0 \le b2 \le 20$, $1 \le b1+b2 \le 20$, and $1 \le c \le 4$.

The stretchable film like this is not deformed by heat and hardly causes lowering of the strength after repeating expansion and contraction because the cured product of resin containing the polymer compound attains the strength not only through hydrogen bonds of urethane but also through covalent bonds of acrylic crosslinking due to crosslink of the (meth)acrylate groups.

In the stretchable film of the present invention, the polymer compound preferably has a weight average molecular weight of 500 or more.

The stretchable film like this is quite excellent in stretchability and strength.

It is preferable that the inventive stretchable film exhibit a stretching property of 40 to 1000% in a tensile test regulated by JIS K6251.

The stretchable film having such stretchability is particularly excellent as a stretchable film.

It is preferable that the inventive stretchable film be used as a film to be in contact with a conductive wiring having stretchability.

The inventive stretchable film can be preferably used particularly in such uses.

The present invention also provides a method for forming a stretchable film, comprising:

mixing a diol compound containing a diol compound Ma as well as a diol compound Mb1 and/or a diol compound Mb2, together with a compound having an isocyanate group, to be a mixture;

forming a film from the mixture; and curing the film by heating;

wherein the diol compound Ma as well as the diol compound Mb1 and/or the diol compound Mb2 are shown by the following general formulae (2):

(2)

$$HO \diagdown R \diagdown Rf_1 \diagdown R \diagdown OH \quad Ma$$

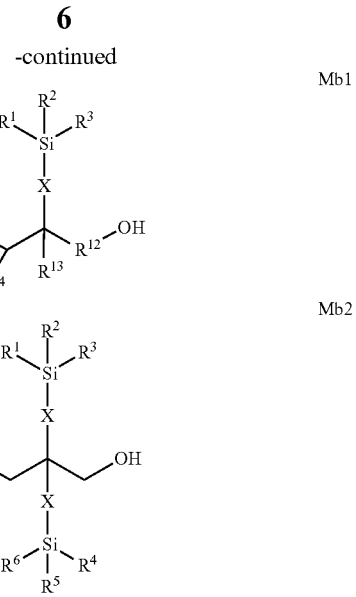

wherein $R^1$, $R^2$, $R^3$, $R^4$, $R^5$, and $R^6$ each represent a linear, branched, or cyclic alkyl group having 1 to 6 carbon atoms, a phenyl group, a 3,3,3-trifluoropropyl group, or a $-(OSiR^7R^8)_n-OSiR^9R^{10}R^{11}$ group; $R^7$, $R^8$, $R^9$, $R^{10}$, and $R^{11}$ each have the same meaning as $R^1$ to $R^6$; each R independently represents a single bond or a methylene group; "n" represents a number in a range of 0 to 100; $R^{12}$ represents a single bond, a methylene group, or an ethylene group; $R^{13}$ represents a hydrogen atom or a linear alkyl group having 1 to 4 carbon atoms; $R^{14}$ represents a hydrogen atom or a methyl group; X represents a linear or branched alkylene group having 3 to 7 carbon atoms, optionally containing an ether group; $Rf_1$ represents a linear or branched alkylene group having 1 to 200 carbon atoms and at least one fluorine atom, optionally containing an ether group.

The inventive method for forming a stretchable film makes it possible to easily form a stretchable film having excellent stretchability and strength that are equivalent to or superior to those of polyurethane, together with very high water repellency on the film surface.

The present invention also provides a method for forming a stretchable film, comprising:

forming a film of a resin containing a compound having a (meth)acrylate group at a terminal thereof; and curing the film by heating and/or light irradiation;

wherein the compound is shown by the following general formula (3):

(3)

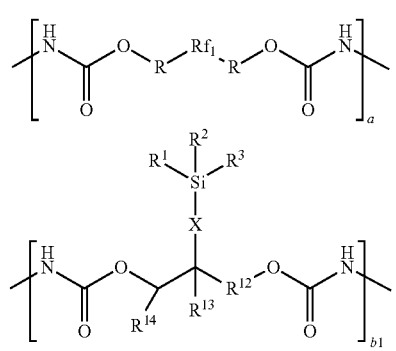

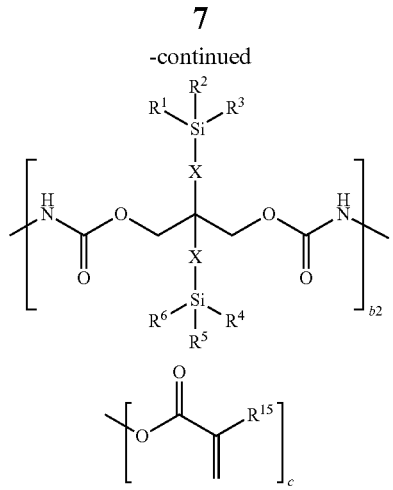

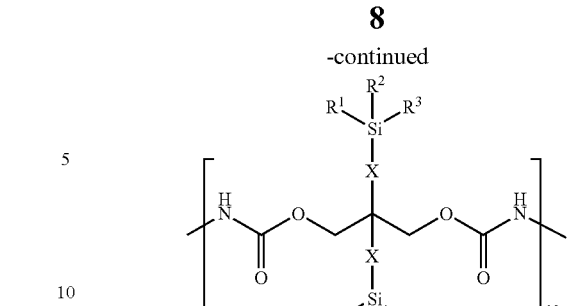

wherein R, $R^2$, $R^3$, $R^4$, $R^5$, and $R^6$ each represent a linear, branched, or cyclic alkyl group having 1 to 6 carbon atoms, a phenyl group, a 3,3,3-trifluoropropyl group, or a —$(OSiR^7R^8)_n$—$OSiR^9R^{10}R^{11}$ group; $R^7$, $R^8$, $R^9$, $R^{10}$, and $R^{11}$ each have the same meaning as $R^1$ to $R^6$; each R independently represents a single bond or a methylene group; "n" represents a number in a range of 0 to 100; $R^{12}$ represents a single bond, a methylene group, or an ethylene group; $R^{13}$ represents a hydrogen atom or a linear alkyl group having 1 to 4 carbon atoms; $R^{14}$ represents a hydrogen atom or a methyl group; X represents a linear or branched alkylene group having 3 to 7 carbon atoms, optionally containing an ether group; $Rf_1$ represents a linear or branched alkylene group having 1 to 200 carbon atoms and at least one fluorine atom, optionally containing an ether group; $R^{15}$ represents a hydrogen atom or a methyl group; and "a", "b1", "b2", and "c" are each number of units in one molecule and are in ranges of $1 \le a \le 20$, $0 \le b1 \le 20$, $0 \le b2 \le 20$, $1 \le b1+b2 \le 20$, and $1 \le c \le 4$.

The inventive method for forming a stretchable film makes it possible to easily form a stretchable film having excellent stretchability and strength that are equivalent to or superior to those of polyurethane, together with very high water repellency on the film surface, and to combine heat curing and photo-curing as described above.

The present invention further provides a polymer compound comprising a structure shown by the following general formula (1), having a weight average molecular weight in a range of 500 to 1000000;

(1)

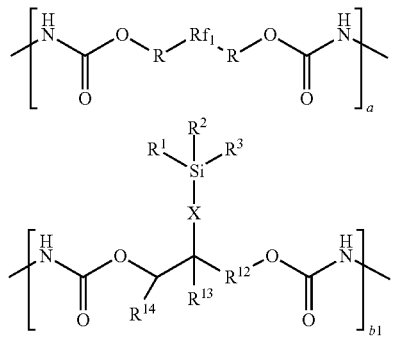

wherein $R^1$, $R^2$, $R^3$, $R^4$, $R^5$, and $R^6$ each represent a linear, branched, or cyclic alkyl group having 1 to 6 carbon atoms, a phenyl group, a 3,3,3-trifluoropropyl group, or a —$(OSiR^7R^8)_n$—$OSiR^9R^{10}R^{11}$ group; $R^7$, $R^8$, $R^9$, $R^{10}$, and R each have the same meaning as $R^1$ to $R^6$; each R independently represents a single bond or a methylene group; "n" represents a number in a range of 0 to 100; $R^{12}$ represents a single bond, a methylene group, or an ethylene group; $R^{13}$ represents a hydrogen atom or a linear alkyl group having 1 to 4 carbon atoms; $R^{14}$ represents a hydrogen atom or a methyl group; X represents a linear or branched alkylene group having 3 to 7 carbon atoms, optionally containing an ether group; $Rf_1$ represents a linear or branched alkylene group having 1 to 200 carbon atoms and at least one fluorine atom, optionally containing an ether group; and "a", "b1", and "b2" are each number of units in the structure and are integers in ranges of $1 \le a \le 20$, $0 \le b1 \le 20$, $0 \le b2 \le 20$, and $1 \le b1+b2 \le 20$.

The polymer compound like this allows a resin containing this polymer to be cured to form a stretchable film having excellent stretchability and strength that are equivalent to polyurethane as well as high water repellency.

In this case, it is preferable to contain a structure shown by the following general formula (3):

(3)

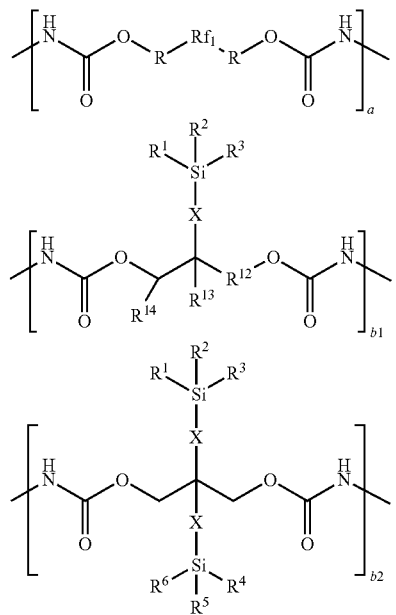

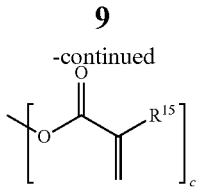

wherein $R^1$ to $R^{14}$, X, $Rf_1$, and R are as defined above; $R^{15}$ represents a hydrogen atom or a methyl group; and "a", "b1", "b2", and "c" are each number of units in the structure and are in ranges of $1 \leq a \leq 20$, $0 \leq b1 \leq 20$, $0 \leq b2 \leq 20$, $1 \leq b1+b2 \leq 20$, and $1 \leq c \leq 4$.

The polymer compound like this makes it possible to obtain a stretchable film having particularly excellent strength.

Advantageous Effects of Invention

As described above, the inventive stretchable film has a urethane bond in the main chain to have excellent stretchability and strength that are equivalent to those of polyurethane, and the film surface has very high water repellency due to interaction of the fluoroalkyl group and the trialkylsilyl group. The stretchable film like this may be brought in contact with a conductive wiring or used for coating one side or the both sides of a conductive wiring to give a stretchable wiring film. The stretchable wiring film like this is also excellent in water repellency on the surface not only excellent in stretchability and strength. Accordingly, the stretchable film of the present invention can be used particularly preferably as a stretchable film that is capable of mounting not only a wiring part for connecting a bio-electrode and a sensor but also all of such a bio-electrode and sensor in a wearable device.

DESCRIPTION OF EMBODIMENTS

Figure 1:
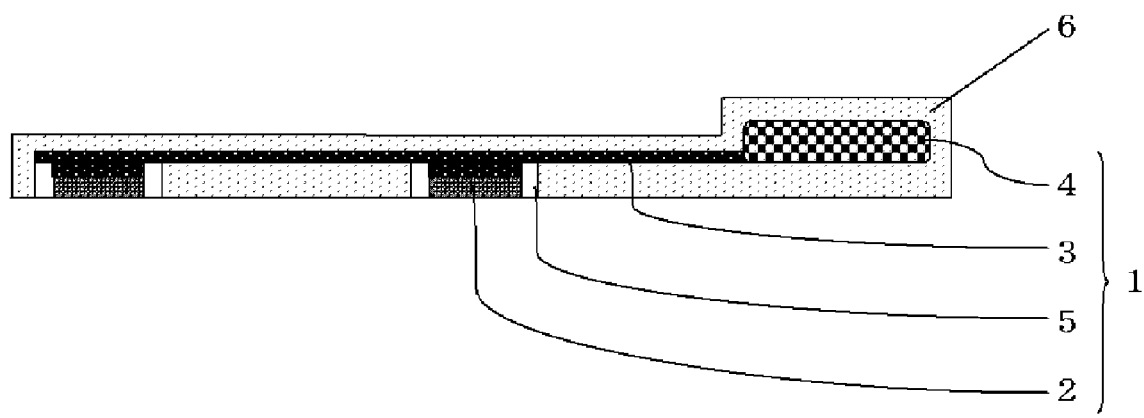
FIG. 1 is a sectional view showing an electrocardiograph covered with the inventive stretchable film.

As described above, polyurethane has sufficient stretchability and strength, but has drawbacks of lower water repellency and lowering the strength and stretchability due to hydrolysis. Accordingly, when a polyurethane sheet has been stuck onto clothes by hot melt and so on, the polyurethane sheet sometimes cause peeling and cracking by washing the clothes repeatedly. Similarly, when a device is covered with polyurethane and stuck onto clothes, the device sometimes fails to function by washing the clothes repeatedly. In a cured product of a silicone urethane polymer having both of a urethane bond and a siloxane bond in the main chain, the strength and water repellency are in the middle of those of polyurethane and silicone, and each of them is beyond the strength of polyurethane only or the water repellency of silicone only. In the method of forming a film by blending polyurethane and silicone, followed by baking to unevenly distribute silicone on the film surface to improve the water repellency, the film surface has lower strength, and the silicone fails to rise to the surface without a surface, thereby failing to improve the water repellency in a tightly covered state, for example, when the film is sandwiched with sheets on both sides. Additionally, this method requires previously blending a solvent with a boiling point in the range of 100 to 200° C. to accelerate the uneven distribution of the silicon on the surface, thereby causing limitations on the composition and a process of forming a film such as failing to form a film without solvent. Polyurethane sheets having a fluoroalkyl group or a fluoroalkylene group shows higher water repellency, but is inferior in strength and stretchability. When this sheet is stuck to clothes and then tested for washing repeatedly as described above, the sheet sometimes causes cracking and peeling. Under these circumstances, it has been desired to develop a stretchable film having excellent stretchability and strength that are equivalent to polyurethane, with the film surface having sufficiently higher strength as well as excellent water repellency and surface hardness that are equivalent to or superior to those of silicone; and a method for forming the same.

Accordingly, the present inventors have diligently investigated to solve the foregoing subject. As a result, the inventors have found that a film having very high water repellency as well as excellent stretchability and strength can be obtained using a base resin containing a polymer compound having a repeating unit containing a fluorine atom, a repeating unit containing a silicon atom, and a urethane bond in the main chain; and the film acts as a stretchable film having excellent stretchability and strength that are equivalent to those of polyurethane, with the film surface having excellent water repellency that is equivalent to or superior to that of silicone, to be particularly favorable as a coating film of a stretchable wiring in wearable devices; thereby bringing the present invention to completion.

Thus, the present inventors have found that the film of a cured product of a resin containing a polymer compound having a urethane bond in the main chain, a repeating unit containing a fluorine atom, and a repeating unit containing a silicon atom has excellent stretchability and strength that are equivalent to those of polyurethane as well as very high water repellency, thereby being useful as a film for coating a bio-electrode having stretchability.

That is, the present invention is a stretchable film of a cured product of a resin comprising a polymer compound having a urethane bond in the main chain, a repeating unit containing a fluorine atom, and a repeating unit containing a silicon atom.

Hereinafter, the present invention will be specifically described, but the present invention is not limited thereto.

<Stretchable Film>

The inventive stretchable film is a cured product of a resin, and this resin contains a polymer compound having a urethane bond in the main chain, a repeating unit containing a fluorine atom, and a repeating unit containing a silicon atom. The polymer compound may be any compound that has a repeating unit containing a fluorine atom and a repeating unit containing a silicon atom, together with a urethane bond in the main chain, and is not particularly limited. In each repeating unit, the fluorine atom(s) and the silicon atom(s) may be bonded to any position(s), and the positions are not particularly limited. The stretchable film like this is excellent in stretchability and strength, and the film surface is also excellent in water repellency.

[Polymer Compound]

The polymer compound contained in the resin has a repeating unit containing a fluorine atom and a repeating unit containing a silicon atom, and has a urethane bond in the main chain. The repeating unit containing a fluorine atom may have the fluorine atom(s) in the side chain, and the repeating unit containing a silicon atom may have the silicon atom(s) in the side chain. The polymer compound like this preferably has a structure shown by the following general formula (1):

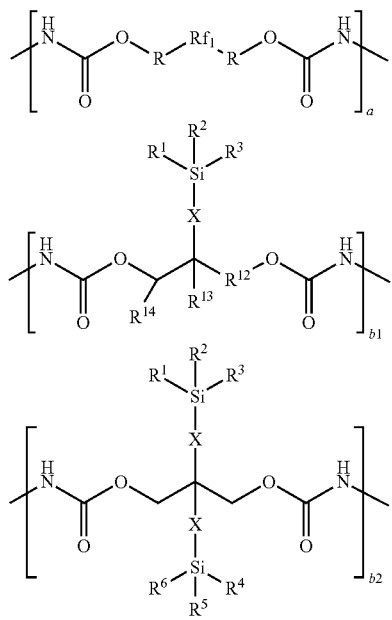

(1)

wherein $R^1$, $R^2$, $R^3$, $R^4$, $R^5$, and $R^6$ each represent a linear, branched, or cyclic alkyl group having 1 to 6 carbon atoms, a phenyl group, a 3,3,3-trifluoropropyl group, or a —(OSiR$^7$R$^8$)$_n$—OSiR$^9$R$^{10}$R$^{11}$ group; $R^7$, $R^8$, $R^9$, $R^{10}$, and $R^{11}$ each have the same meaning as $R^1$ to $R^6$; each R independently represents a single bond or a methylene group; "n" represents a number in the range of 0 to 100; $R^{12}$ represents a single bond, a methylene group, or an ethylene group; $R^{13}$ represents a hydrogen atom or a linear alkyl group having 1 to 4 carbon atoms; $R^{14}$ represents a hydrogen atom or a methyl group; X represents a linear or branched alkylene group having 3 to 7 carbon atoms, optionally containing an ether group; $Rf_1$ represents a linear or branched alkylene group having 1 to 200 carbon atoms and at least one fluorine atom, optionally containing an ether group; and "a", "b1", and "b2" are each number of units in the structure and are integers in ranges of 1≤a≤20, 0≤b1≤20, 0≤b2≤20, and 1≤b1+b2≤20.

Incidentally, in the structure shown by the general formula (1), the repeating unit containing $Rf_1$ is also referred to as a "repeating unit-a", the repeating unit having one side chain containing a silicon atom is referred to as a "repeating unit-b1", and the repeating unit having two side chains each containing a silicon atom is referred to as a "repeating unit-b2".

The polymer compound is preferably a compound having a (meth)acrylate group at the terminal, shown by the following general formula (3):

(3)

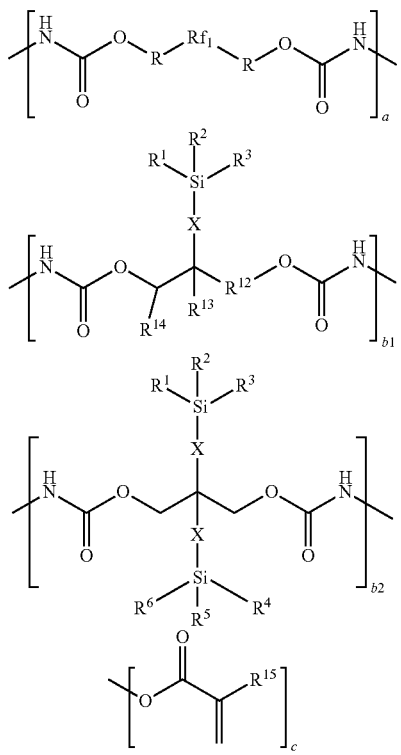

wherein $R^1$ to $R^{14}$, X, $Rf_1$, and R are as defined above; $R^{15}$ represents a hydrogen atom or a methyl group; and "a", "b1", "b2", and "c" are each number of units in one molecule and are in ranges of 1≤a≤20, 0≤b1≤20, 0≤b2≤20, 1≤b1+b2≤20, and 1≤c≤4.

The polymer compound like this is crosslinkable through the (meth)acrylate groups, thereby allowing the resin containing this polymer compound to form a cured product with excellent strength. It is also possible to form a stretchable film by synthesizing such a polymer compound (urethane-(meth)acrylate polymer) and adding a radical generator thereto, followed by crosslinking with radicals generated by light irradiation or heat.

Each repeating unit described above has a moiety to compose a urethane bond, through which each repeating unit binds to form a urethane bond in the main chain. The structure shown by the general formula (1) contains the repeating unit-a as well as the repeating unit-b1 and/or the repeating unit-b2, and may further contain another structural unit(s). For example, the structure may contain a (meth)

acrylate unit at the terminal or in the middle of it. The repeating units may bond with each other in any order.

The polymer compound like this is a polyurethane that has both of a repeating unit of urethane having a fluoroalkyl group or a fluoroalkylene group and a repeating unit of urethane having a siloxane bond(s) in the side chain. Accordingly, the film of a cured product of a resin based on this polymer compound has excellent stretchability and strength that are equal to those of polyurethane, with the film surface having excellent water repellency that is equal to or superior to that of silicone, thereby being particularly preferable as a coating film of a stretchable wiring in wearable devices.

The polymer compound having a structure shown by the general formula (1) can be obtained by reaction of a diol compound shown by the following general formulae (2) and a compound having an isocyanate group(s) (hereinafter, also referred to as an isocyanate compound),

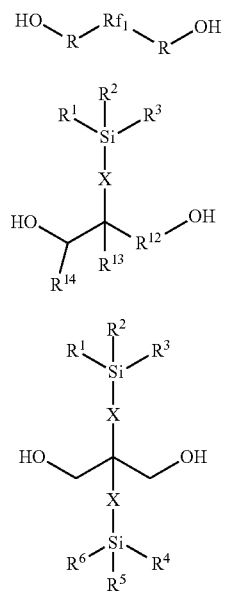

wherein $R^1$ to $R^{14}$, X, $Rf_1$, and R are as defined above.

The diol compound described above preferably has a diol compound Ma as well as a diol compound Mb1 and/or a diol compound Mb2 shown by the general formulae (2). In this context, the diol compound Ma, the diol compound Mb1, and the diol compound Mb2 correspond to the repeating unit-a, the repeating unit-b1, and the repeating unit-b2 respectively. The diol compound may contain a compound that has a plurality of hydroxy groups such as another diol compound. Such a diol compound reacts with an isocyanate compound to form a urethane bond to make a polymer compound having a structure shown by the general formula (1).

As the diol compound Ma having a fluoroalkyl group or a fluoroalkylene group shown by the general formula (2), the following can be specifically exemplified.

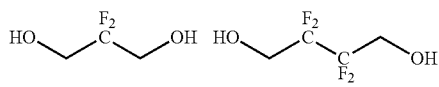

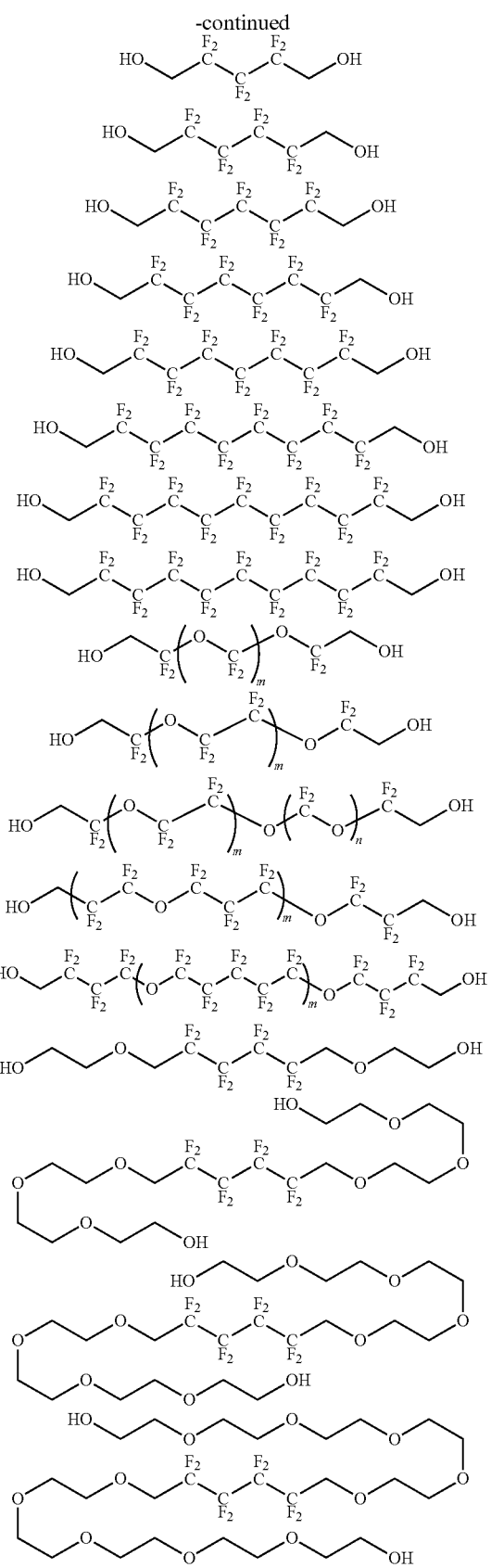

In these formulae, "m" and "n" are each in the range of 0 to 20.

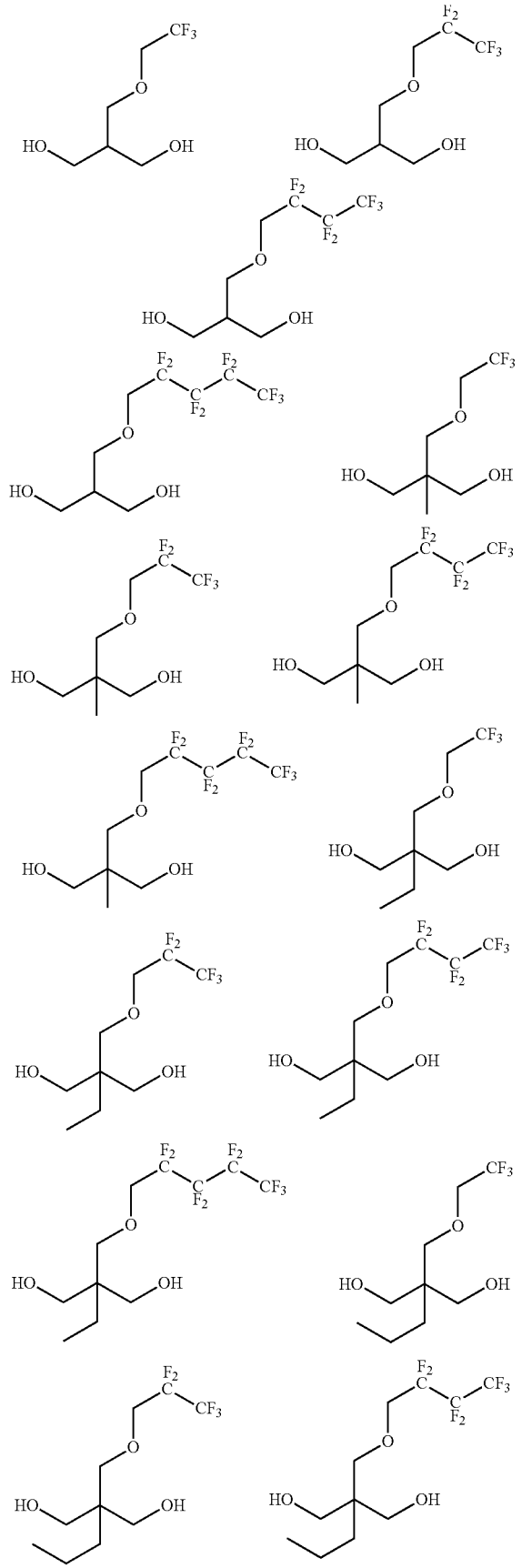
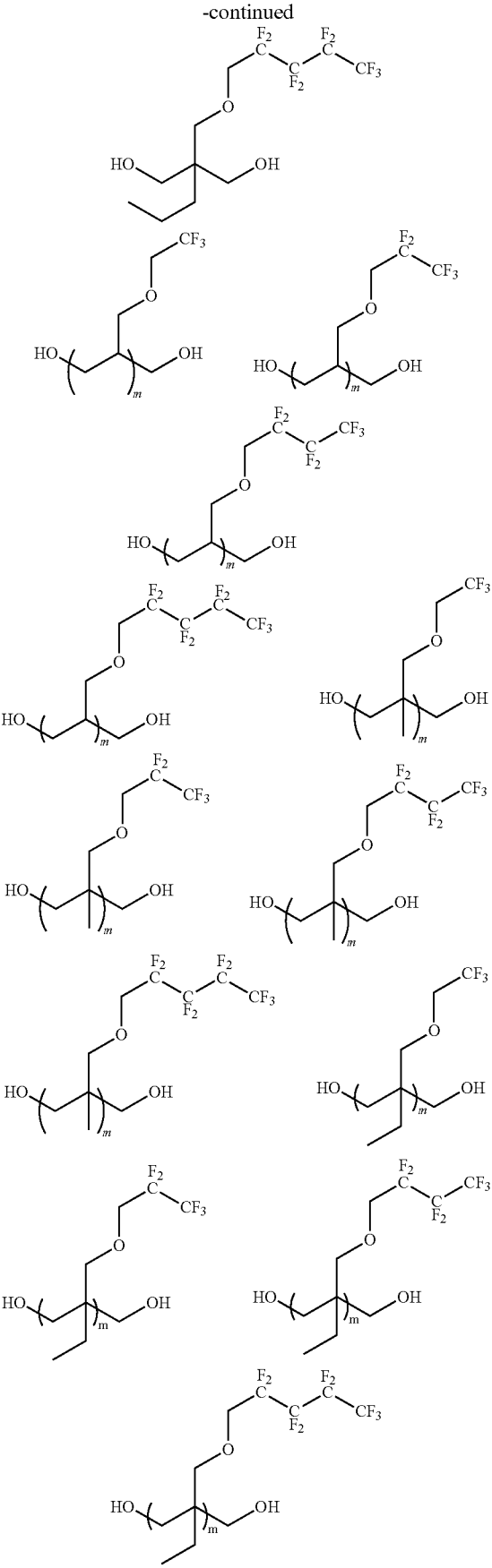
-continued

17
-continued
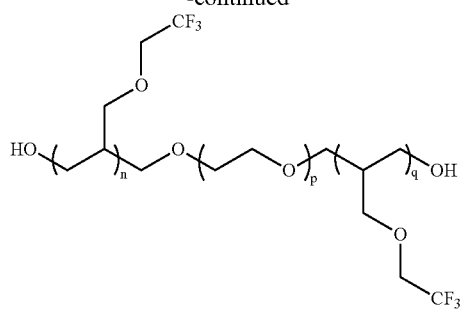
18
-continued
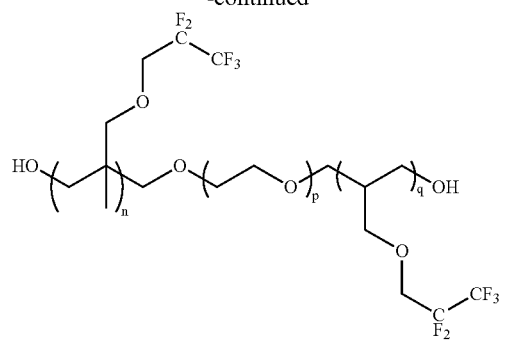
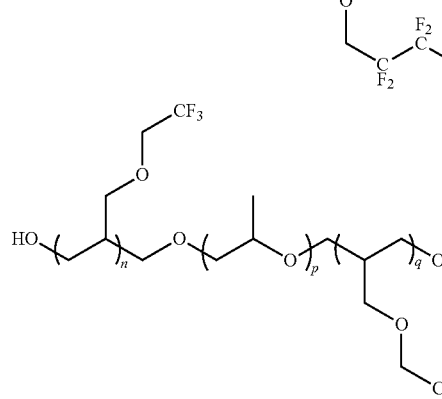
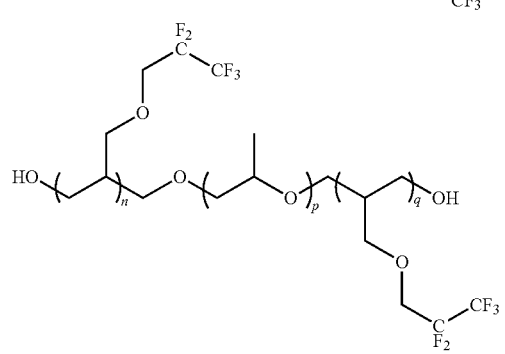

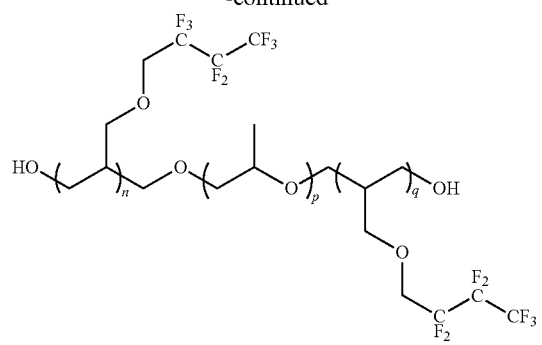
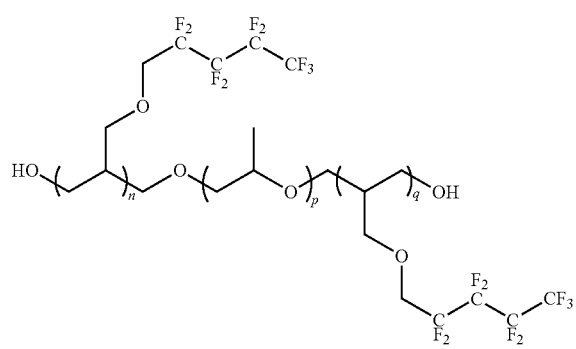
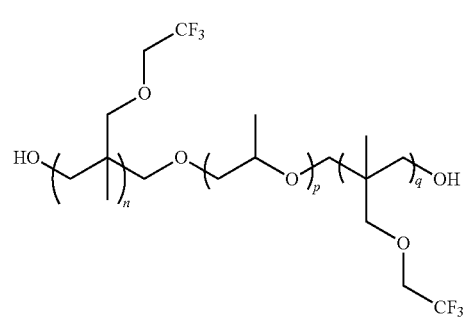
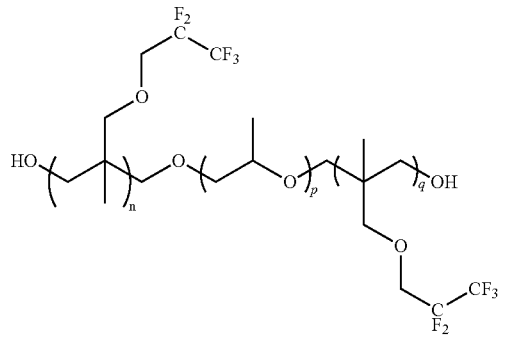
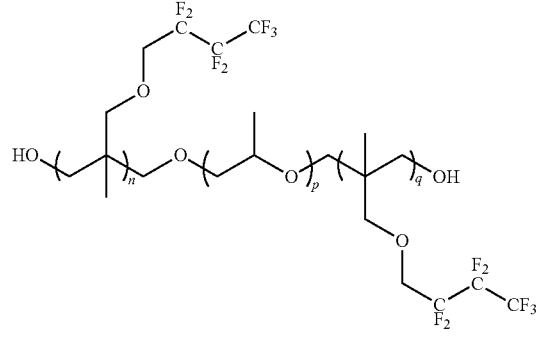
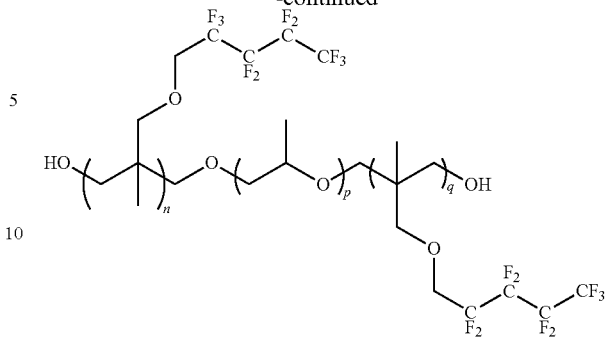
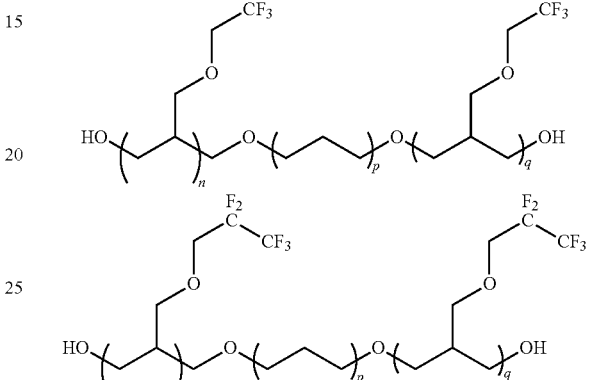
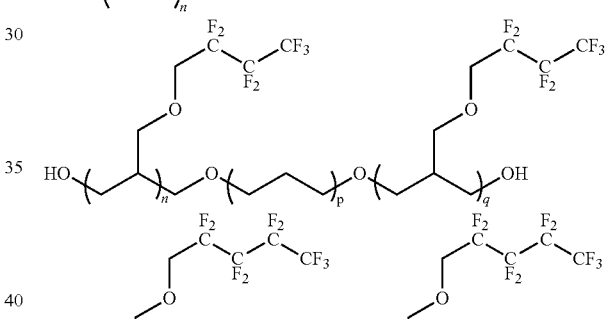
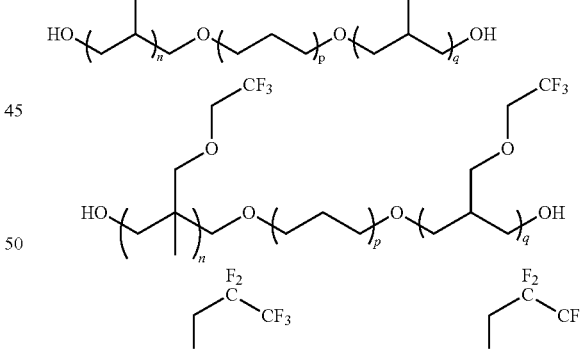
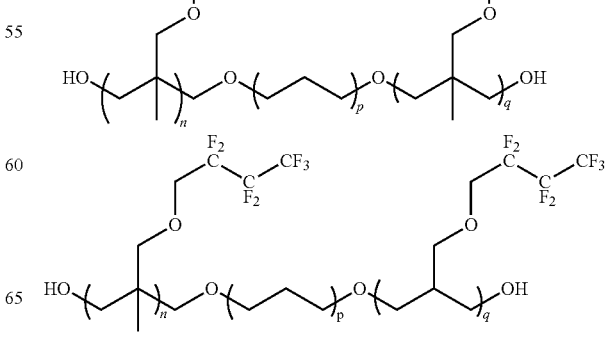

21
-continued
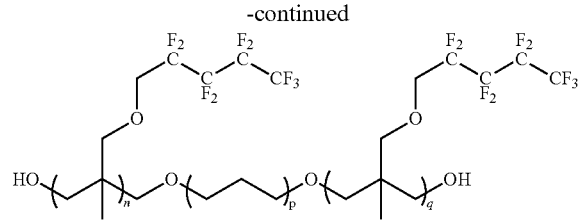
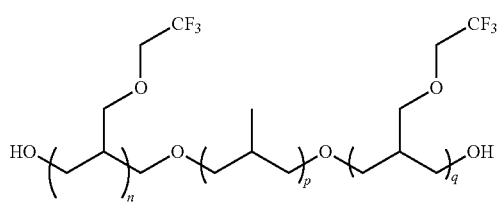
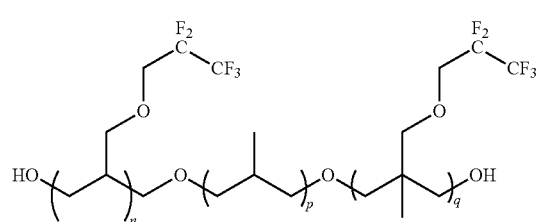
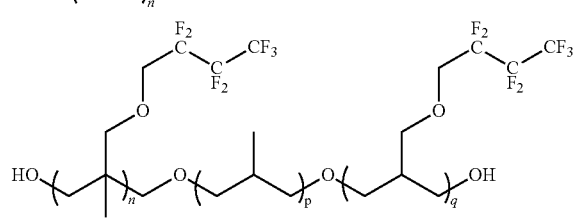
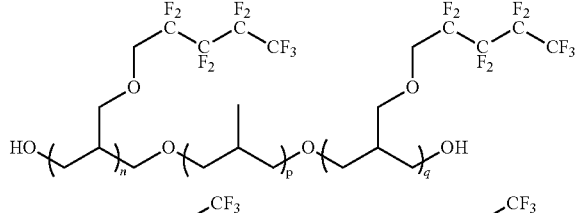
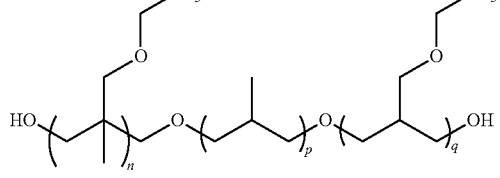
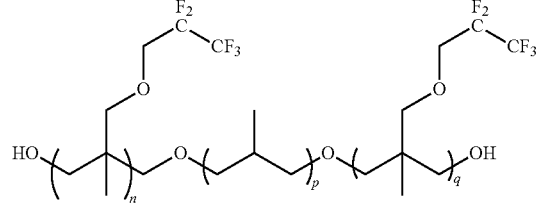
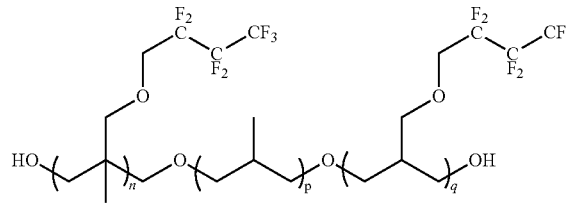
22
-continued
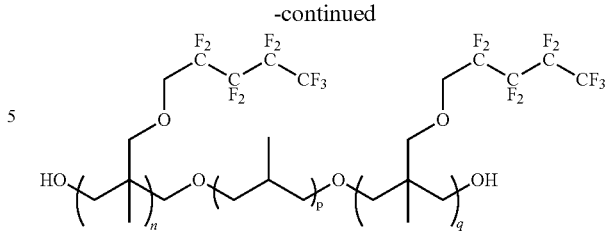
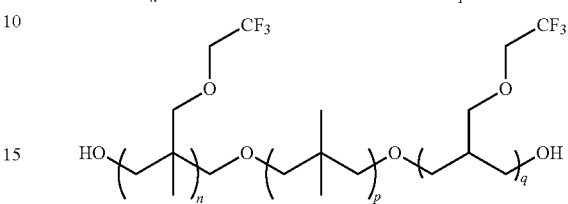
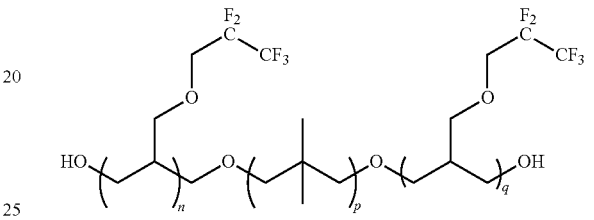
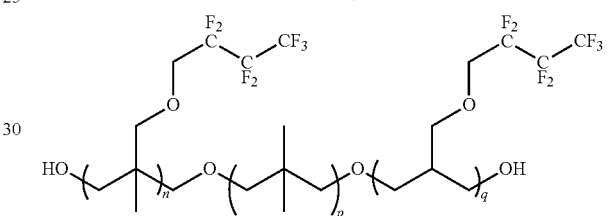
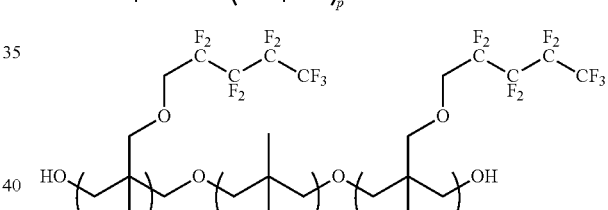
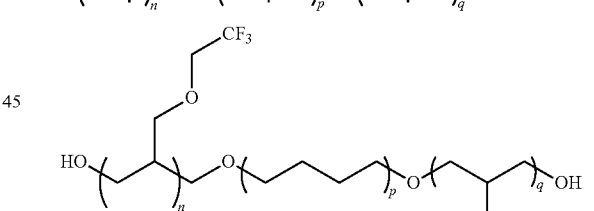
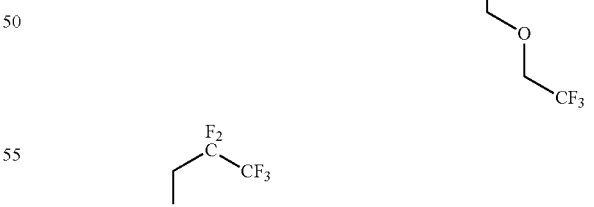
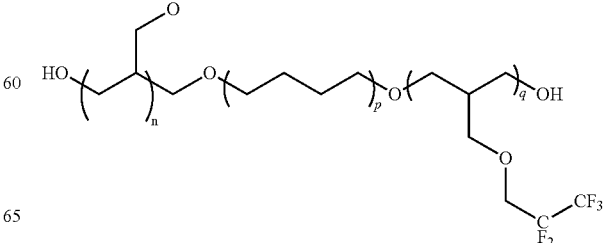

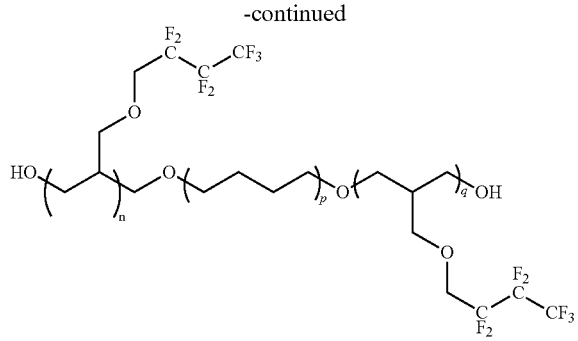
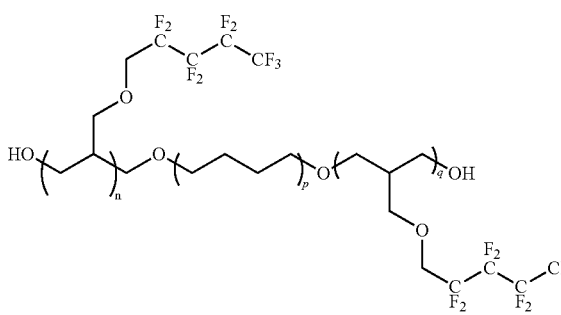
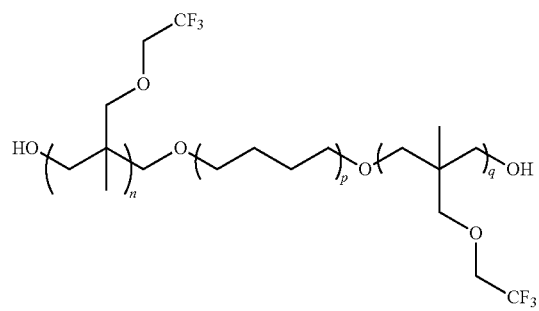
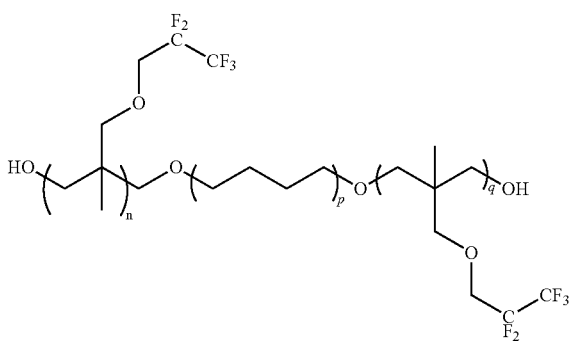
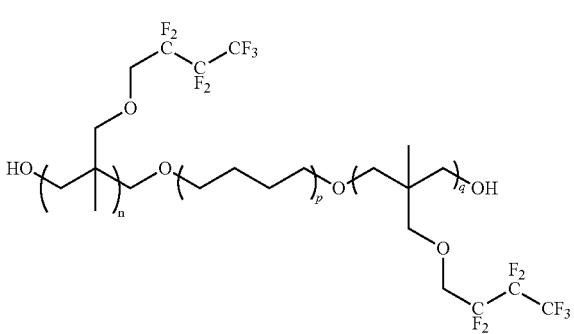
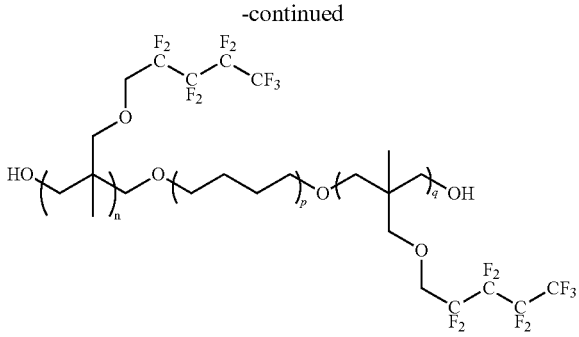
In these formulae, "n" and "q" are each in the range of 1 to 20, provided that $2 \leq n+q \leq 20$; and "p" is in the range of $1 \leq p \leq 40$.
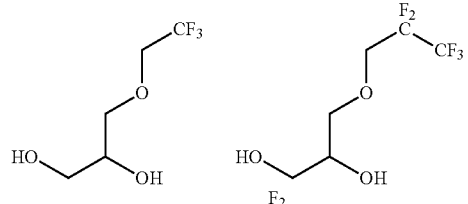
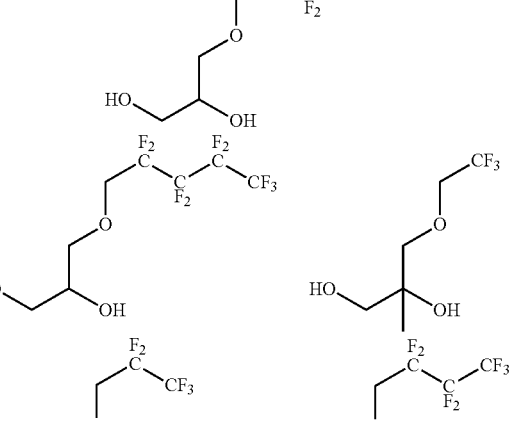
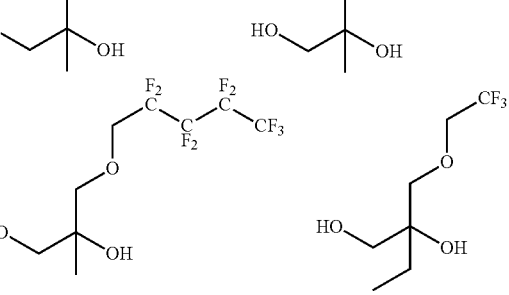
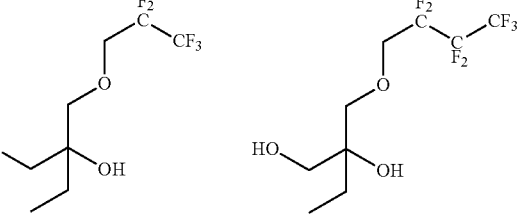

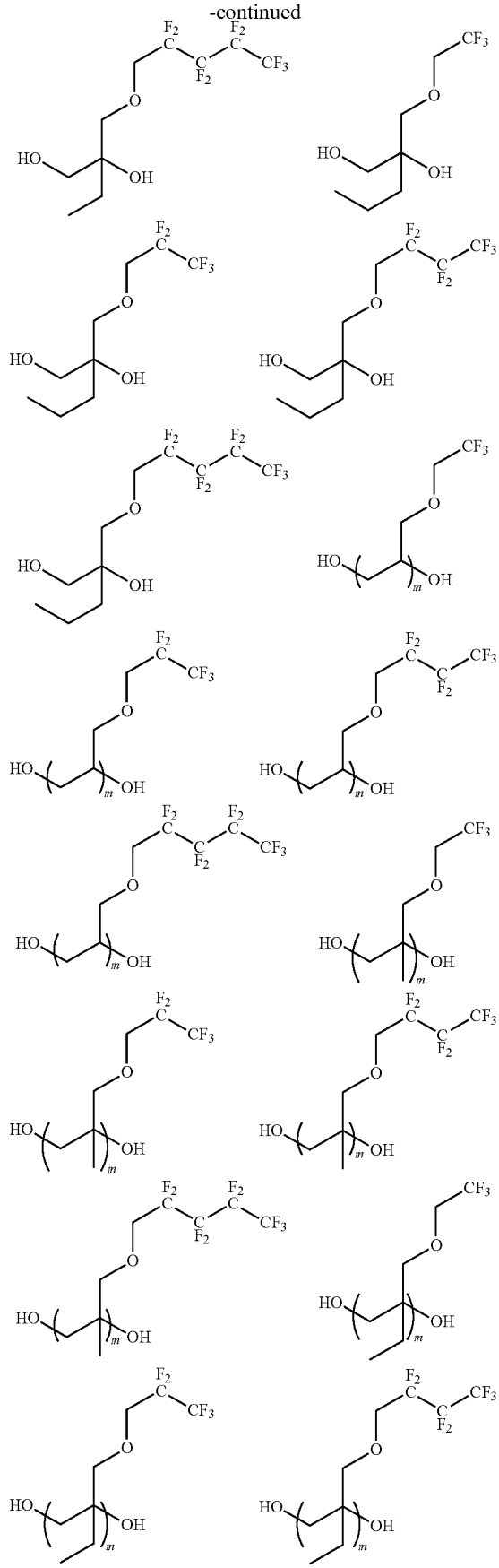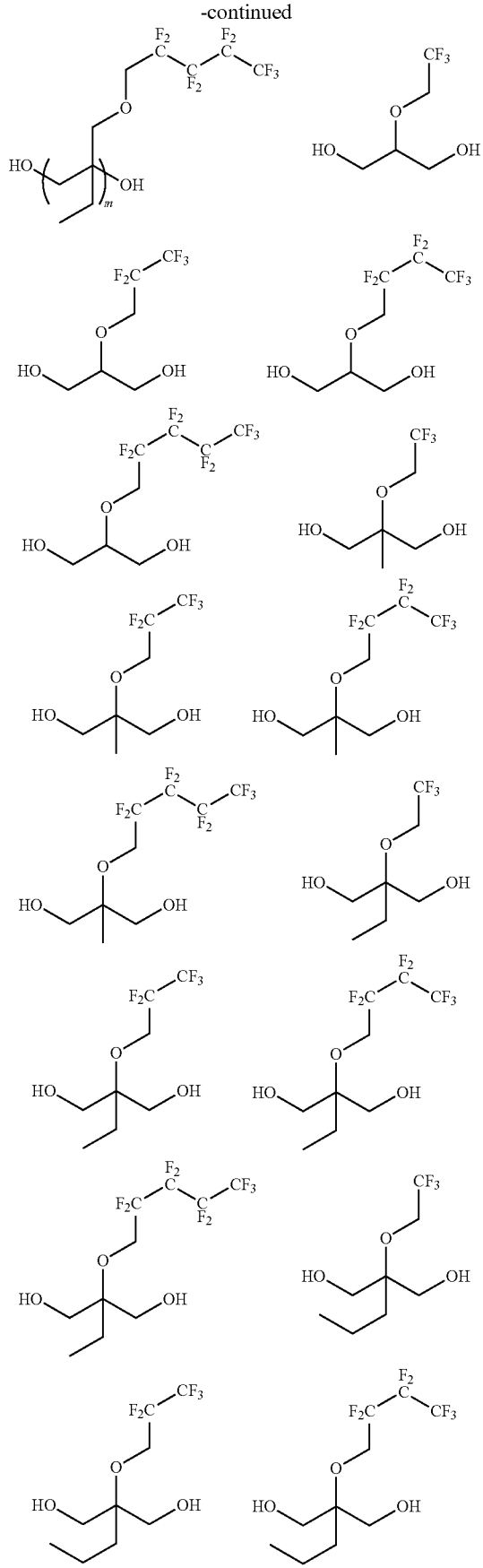

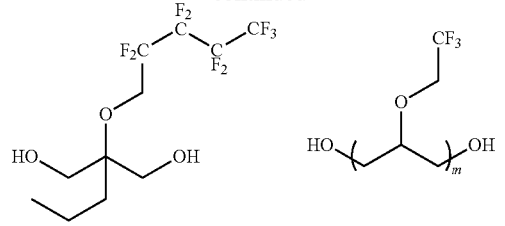
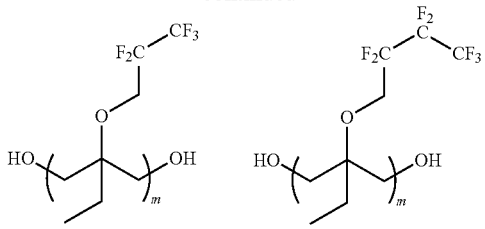
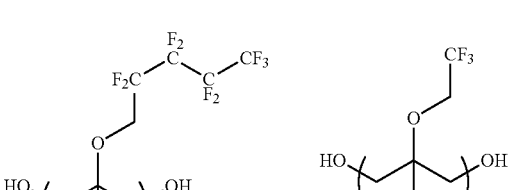
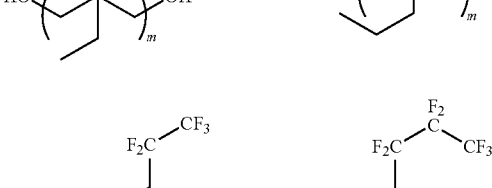
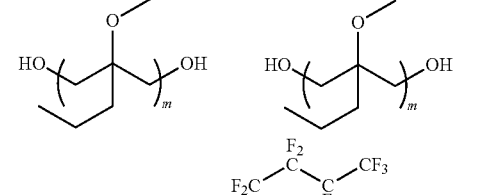
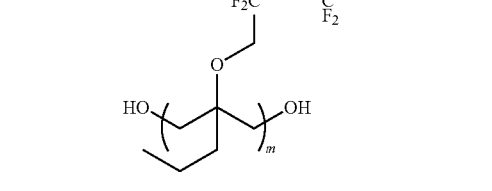
In these formulae, "m" is in the range of 0 to 20.
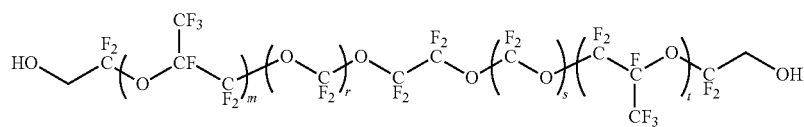
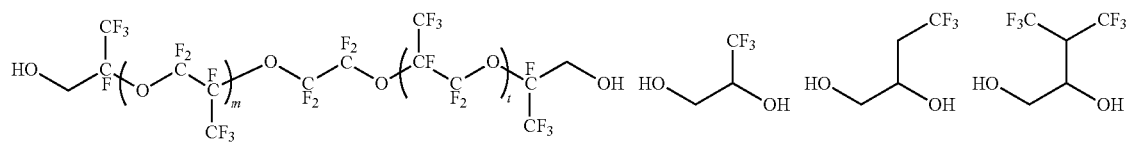
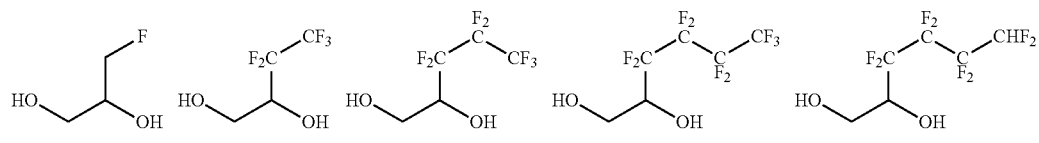
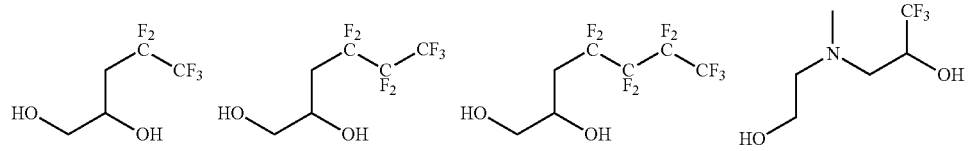

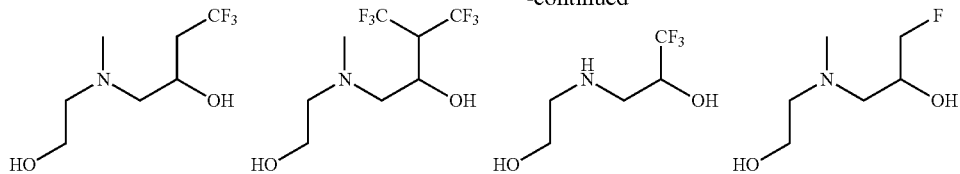

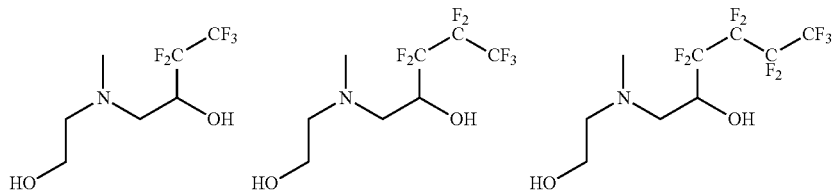

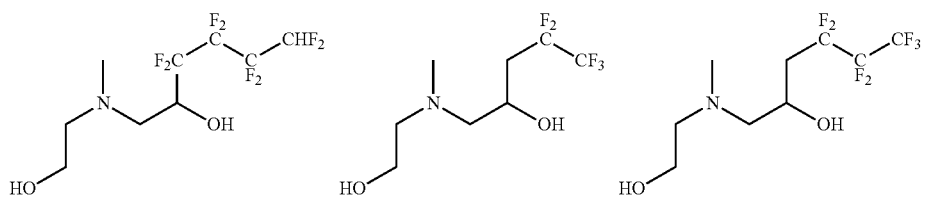

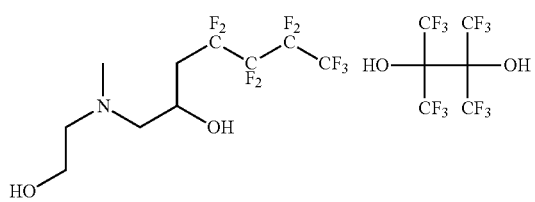

In these formulae, "m", "r", "s", and "t" are each in the range of 0 to 20.

The diol compound Mb1 shown by the general formula (2) having a siloxane pendant can be obtained by, for example, reaction of glycerin monoallyl ether and a short-chain siloxane compound having an Si—H group in the siloxane chain in the presence of a platinum catalyst. Illustrative examples of these diol compounds include the following.

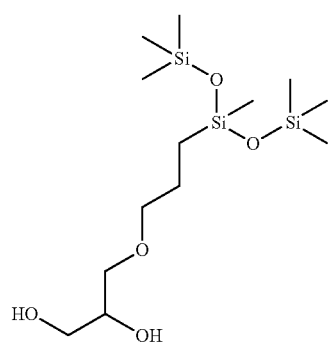

-continued

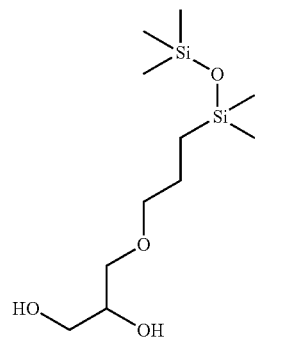

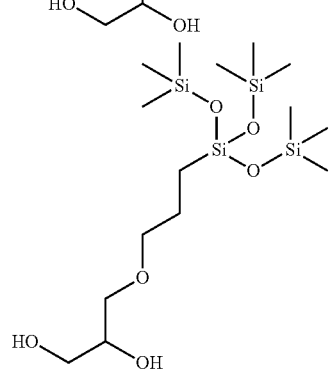

-continued
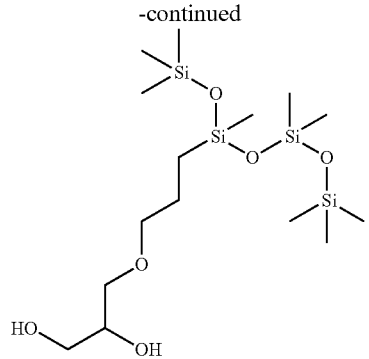
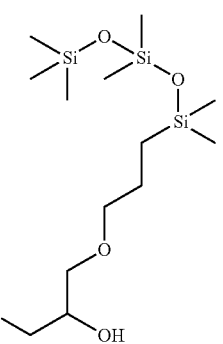
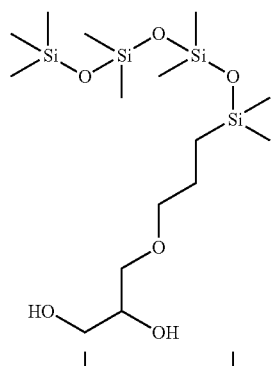
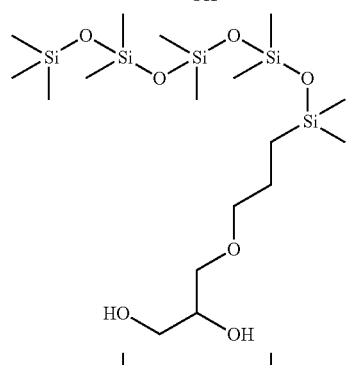
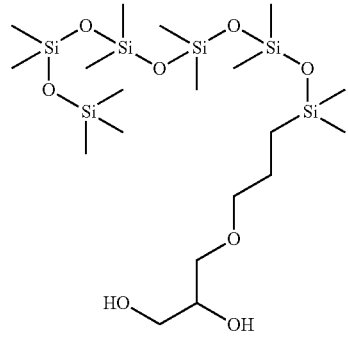
-continued
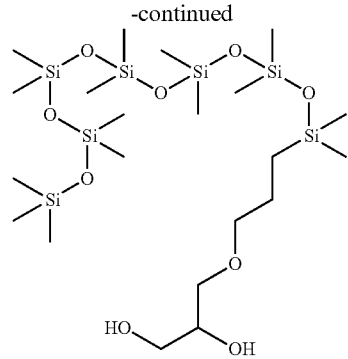
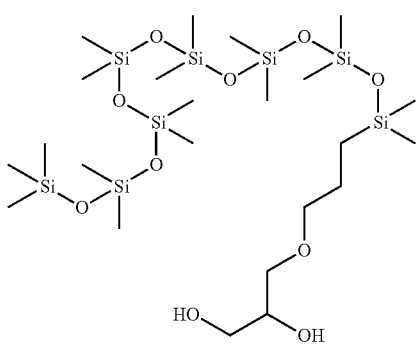
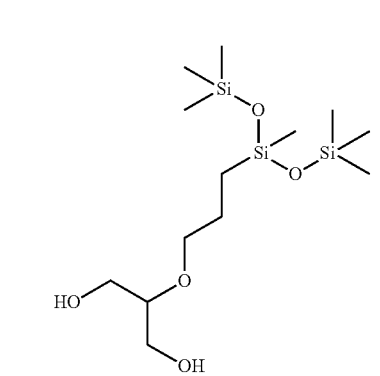
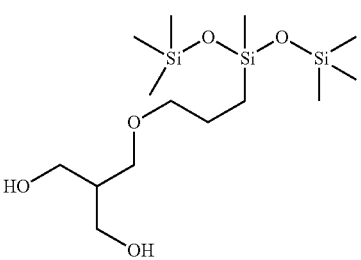
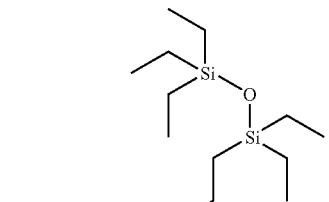
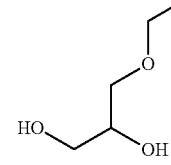

33
-continued
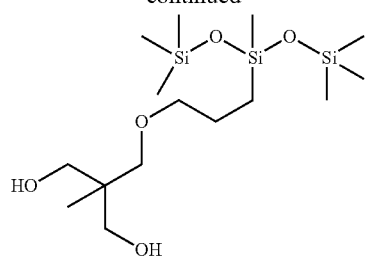
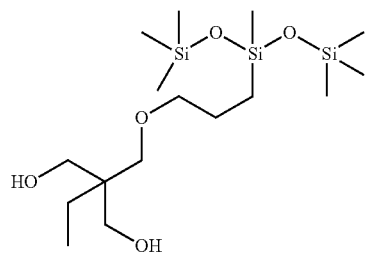
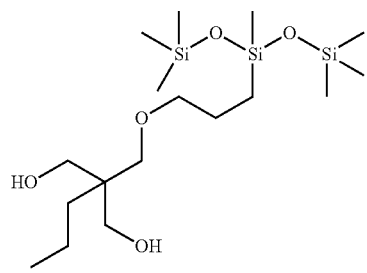
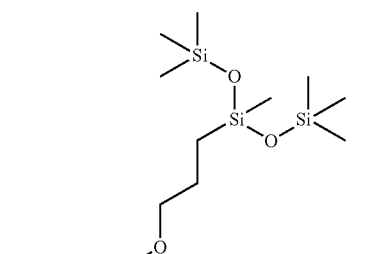
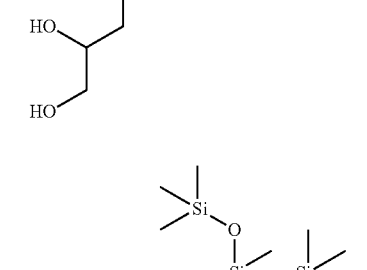
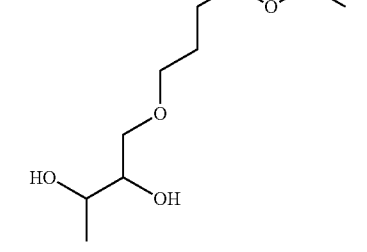
34
-continued
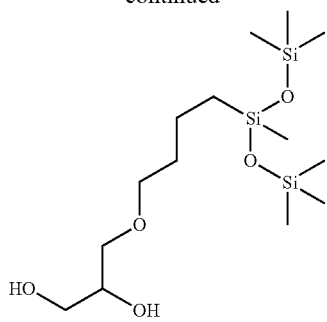
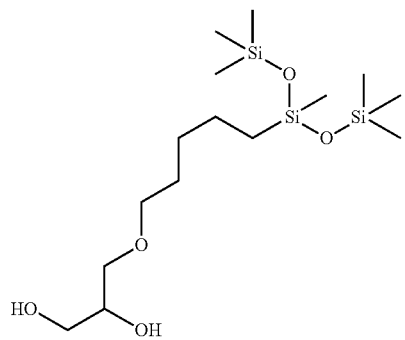
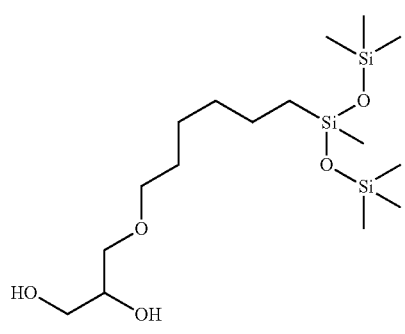
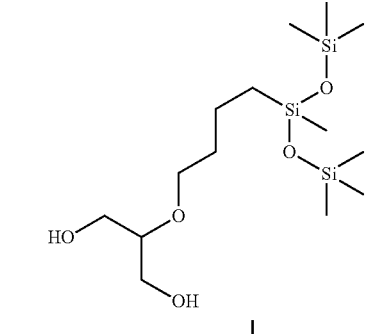
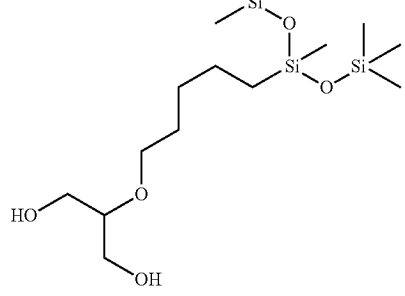

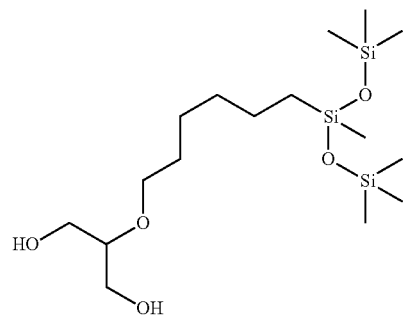
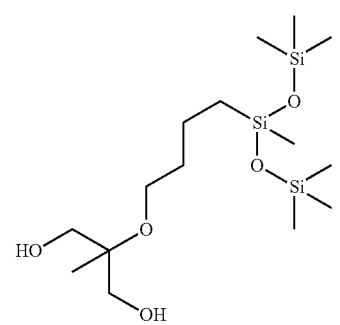
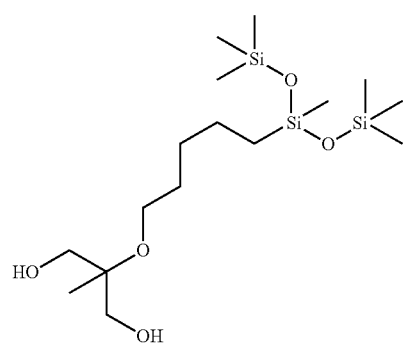
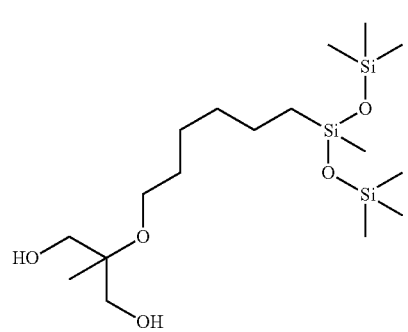
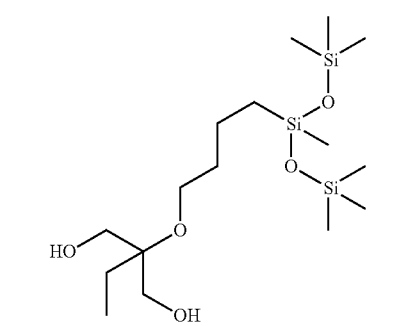
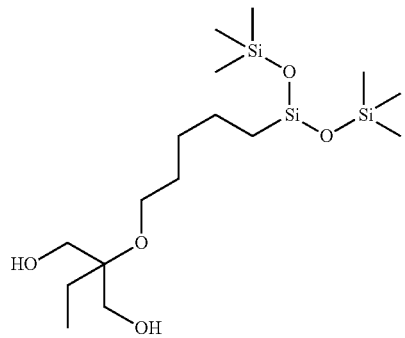
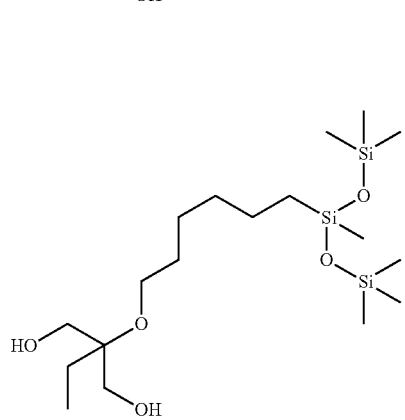
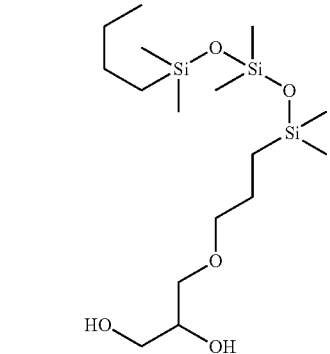
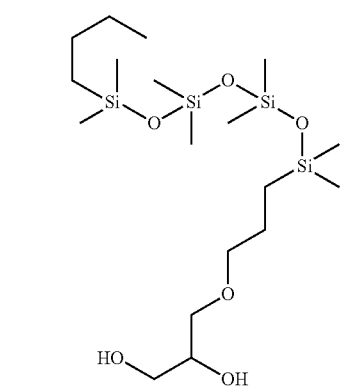

37
-continued
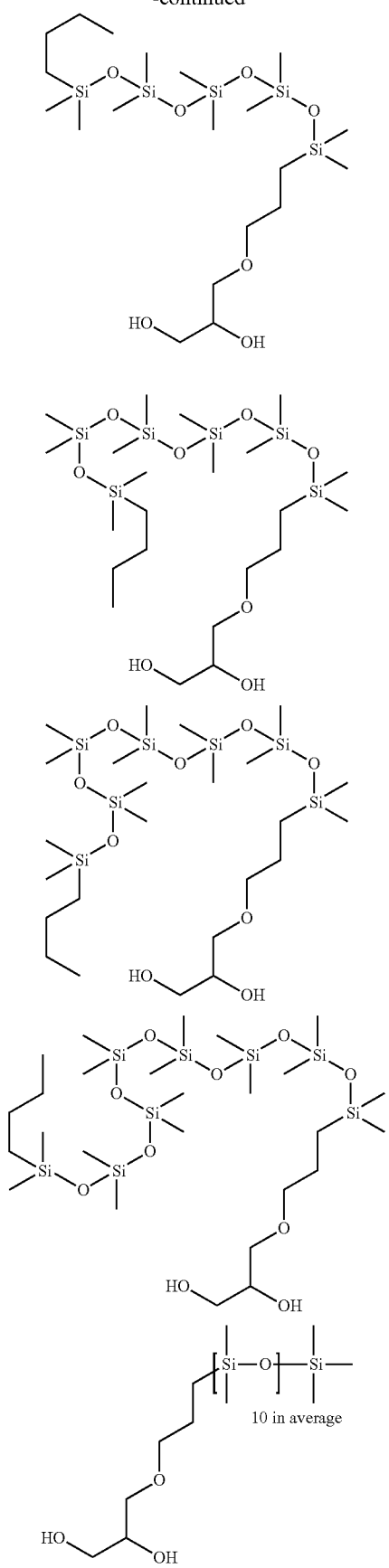
38
-continued
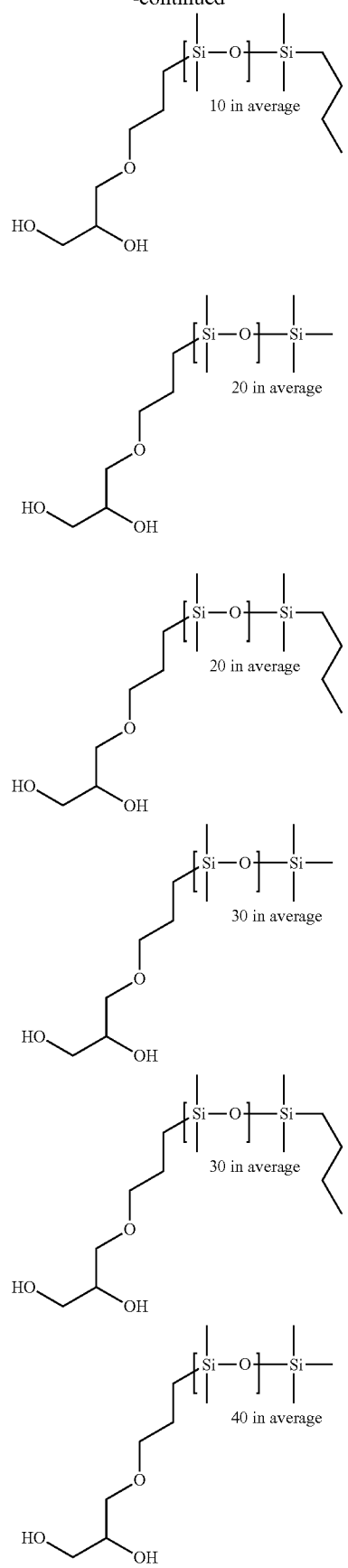

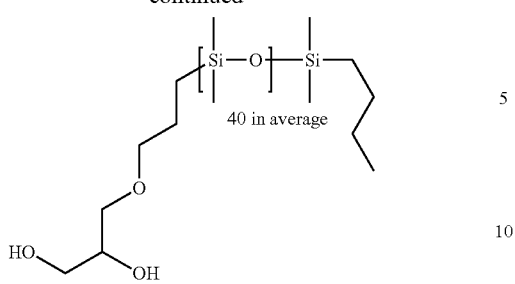

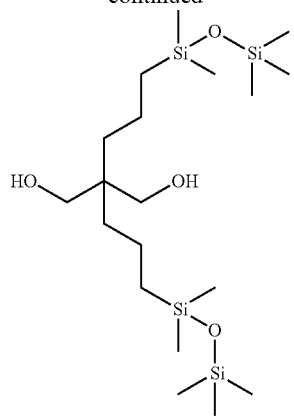

The diol compound Mb2 shown by the general formula (2) having double siloxane pendants can be obtained by, for example, reaction of diol compound having a diallyl ether group and short-chain siloxane compounds each having an Si—H group in the siloxane chain in the presence of a platinum catalyst. Illustrative examples of these diol compounds obtained by such a way include the following.

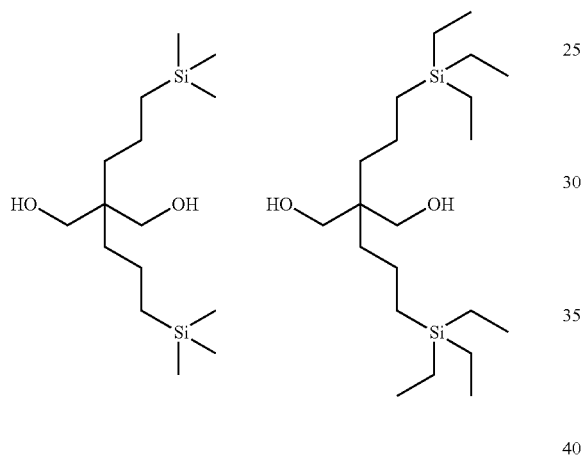

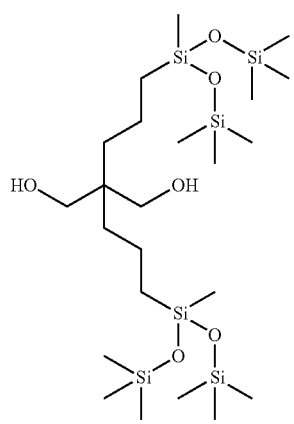

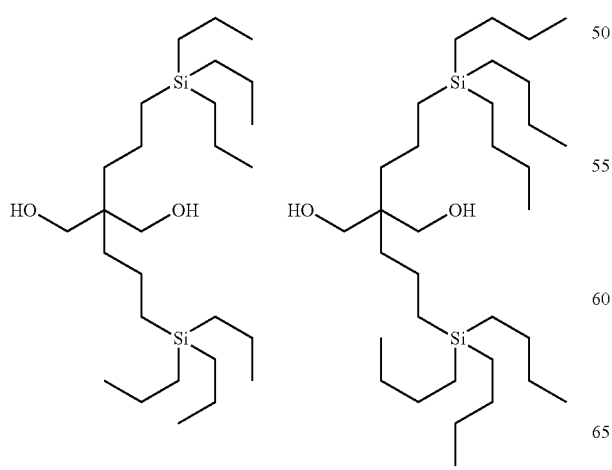

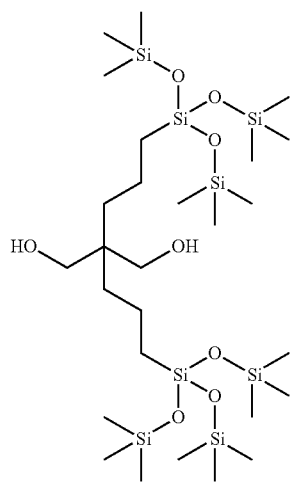

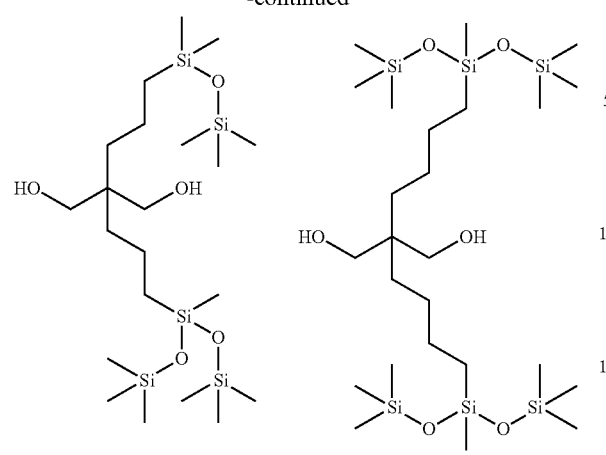
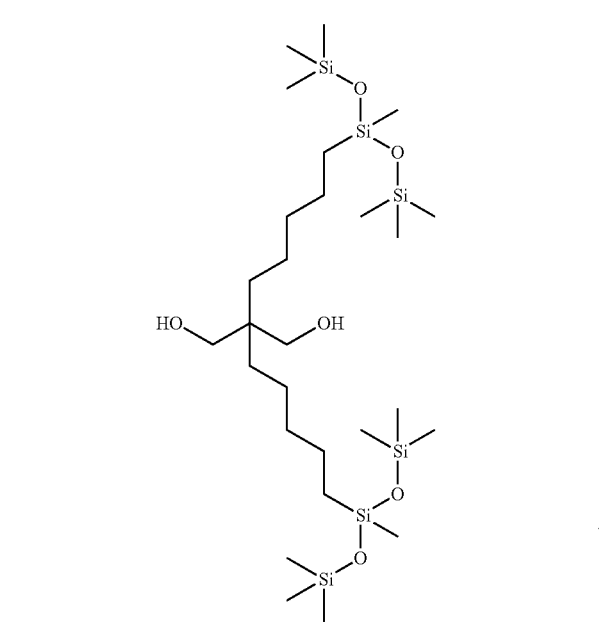
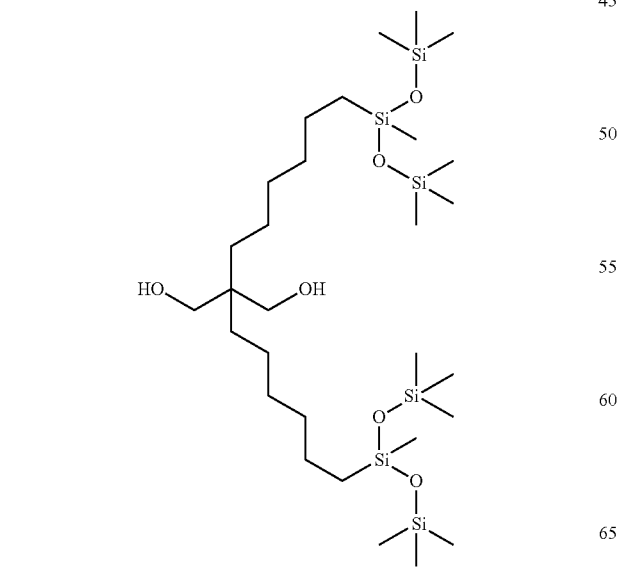
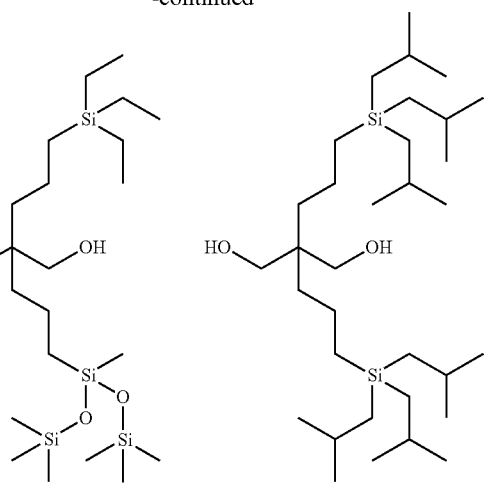
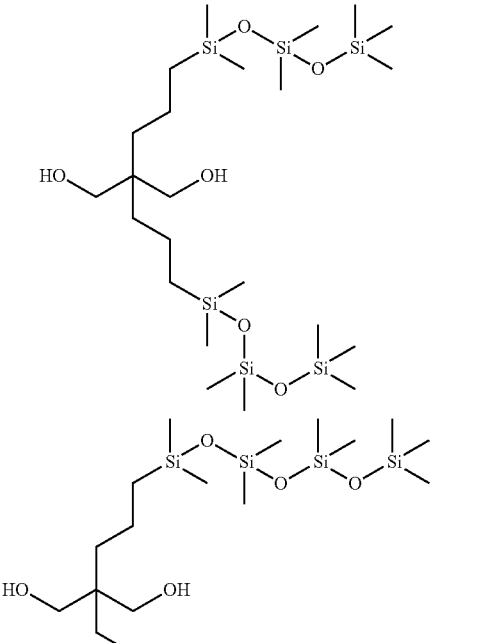
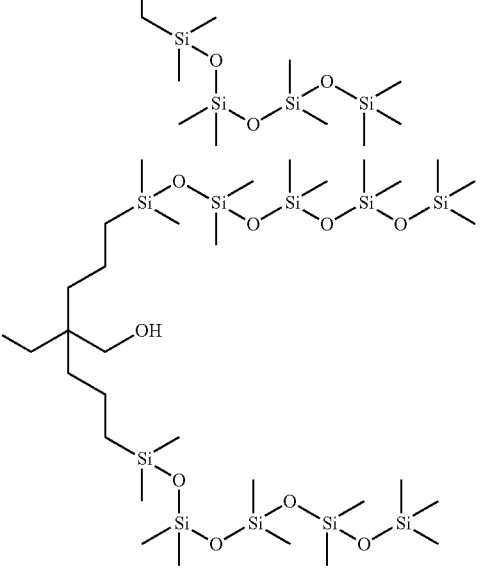

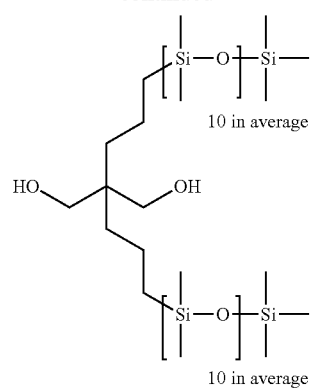
10 in average
10 in average
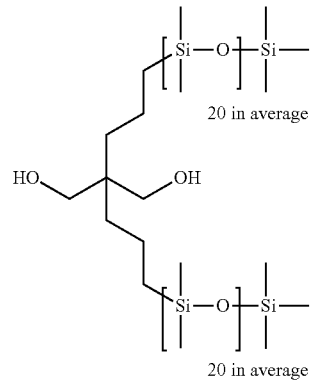
20 in average
20 in average
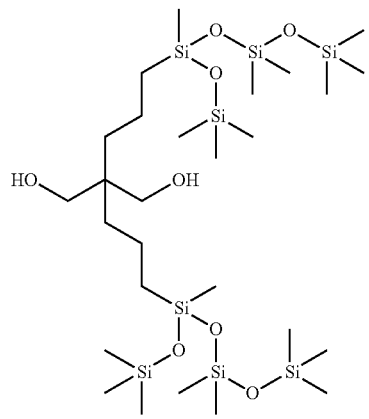
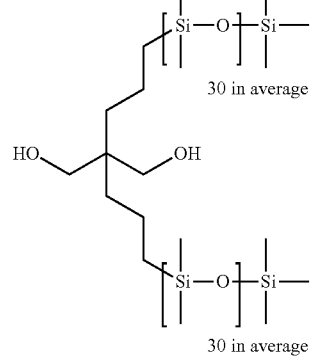
30 in average
30 in average
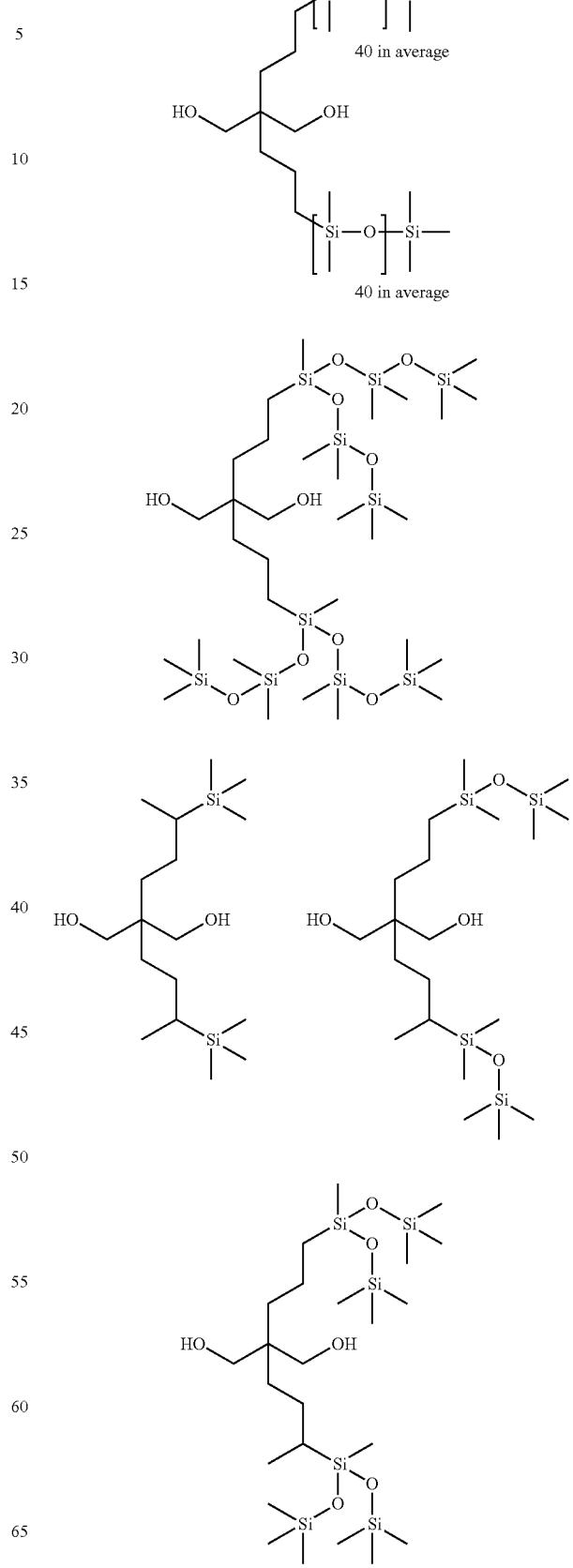
40 in average
40 in average 45
-continued
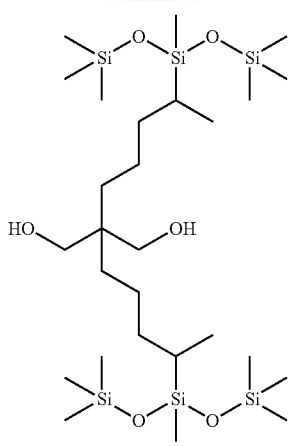
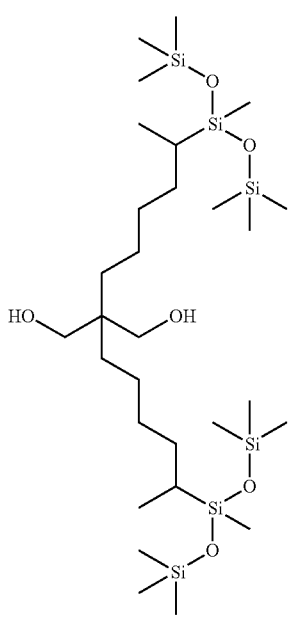
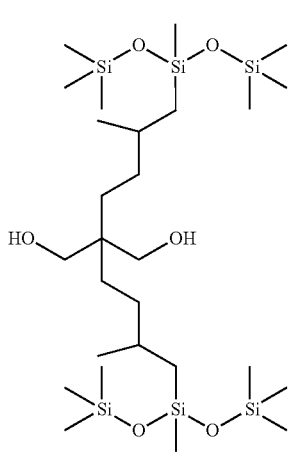
46
-continued
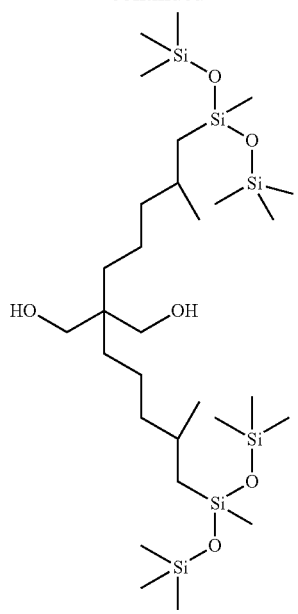
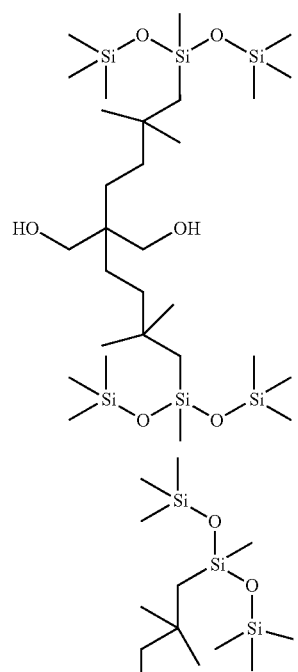

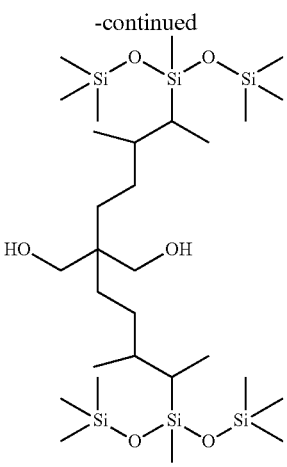
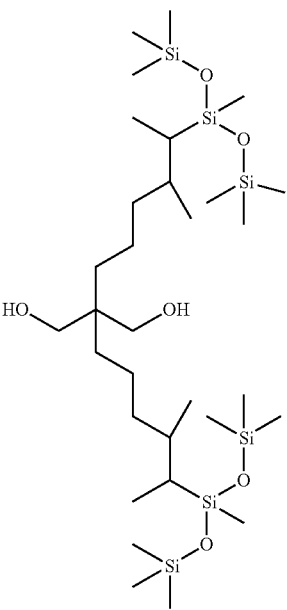
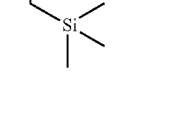
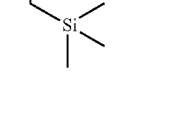
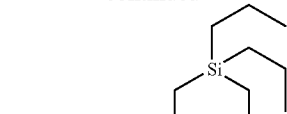
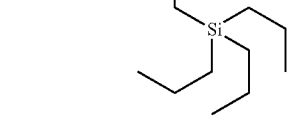
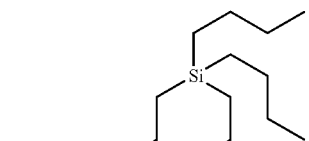
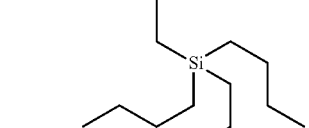
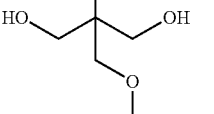
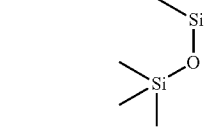

-continued
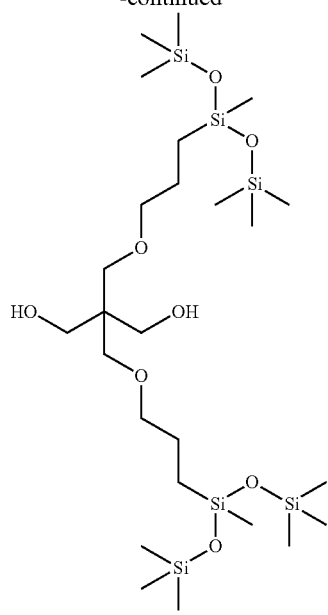
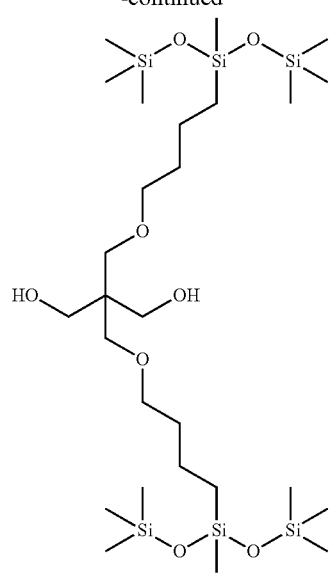
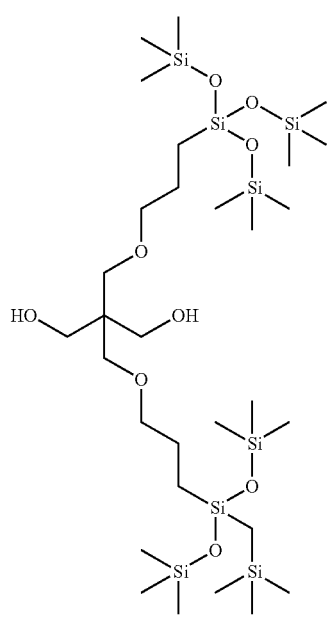
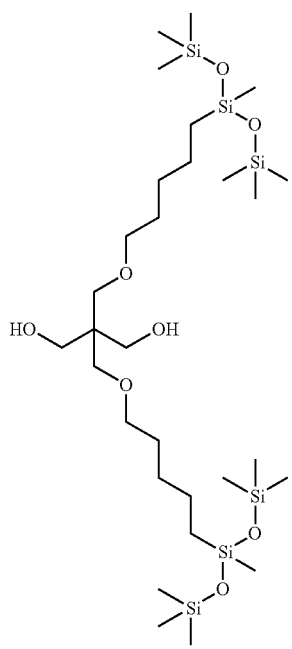

51
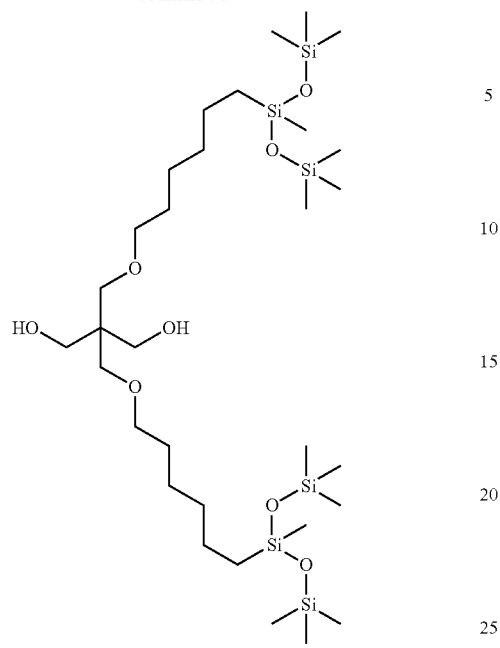
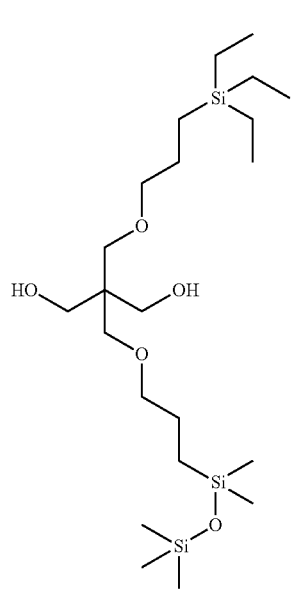
52
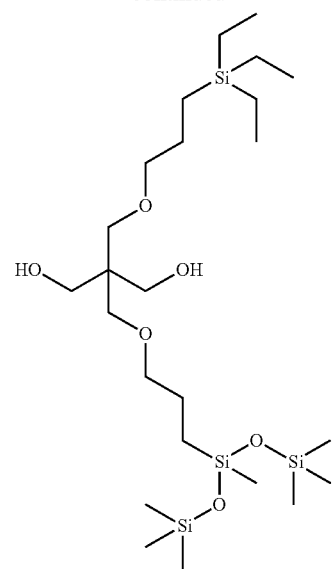
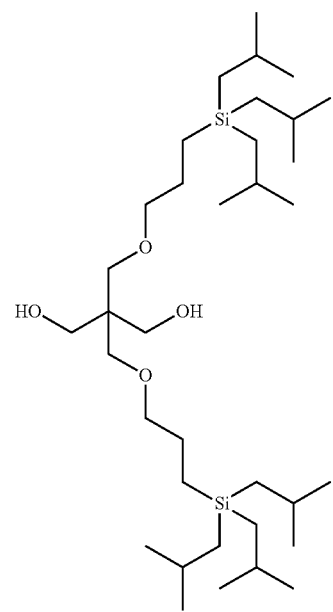

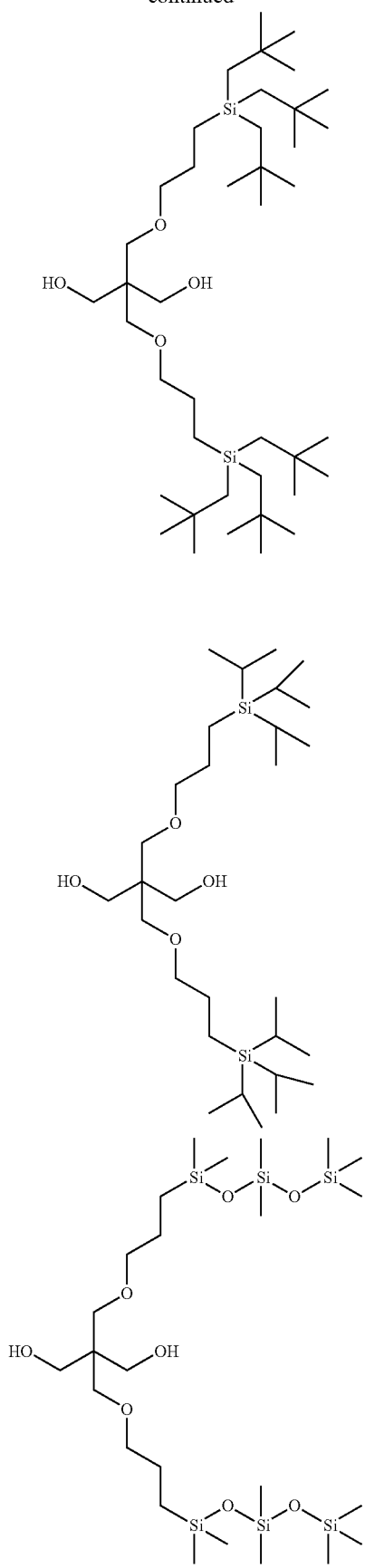
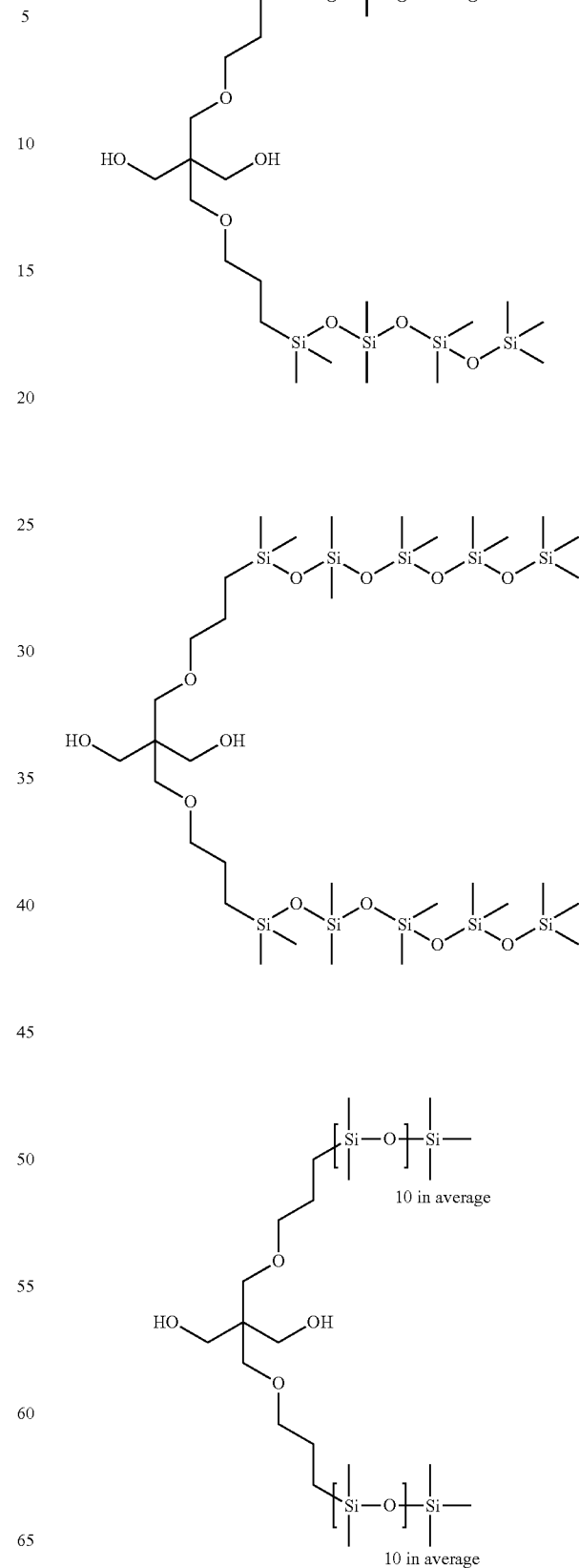

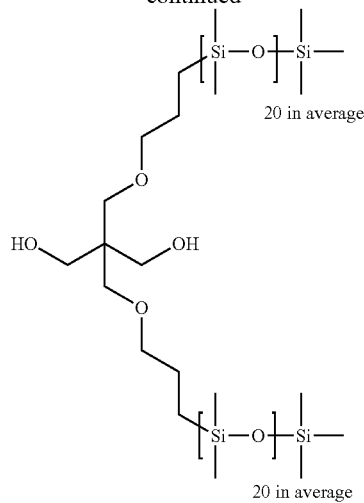
20 in average
20 in average
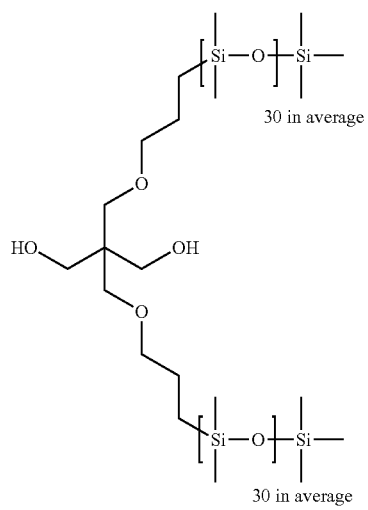
30 in average
30 in average
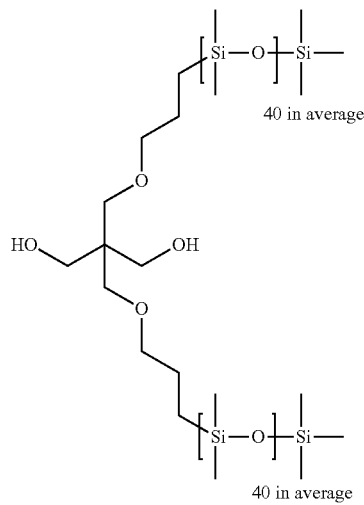
40 in average
40 in average
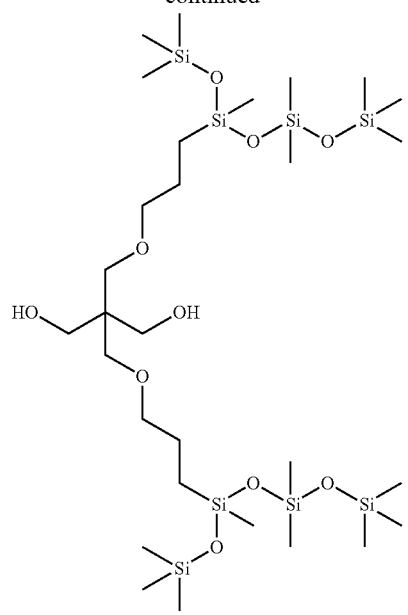
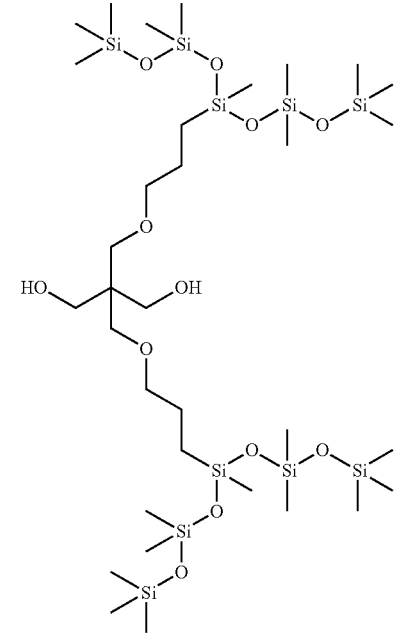

57
-continued
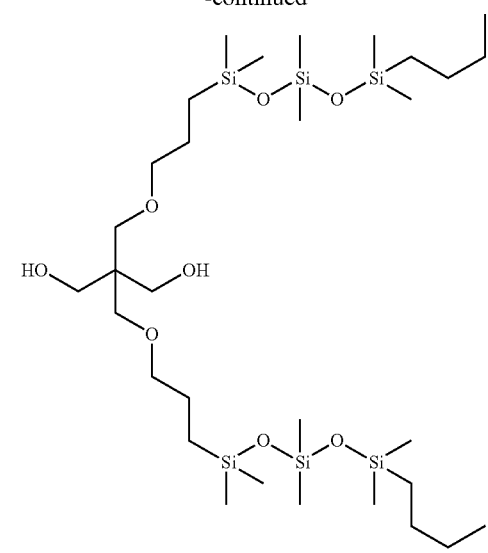
58
-continued
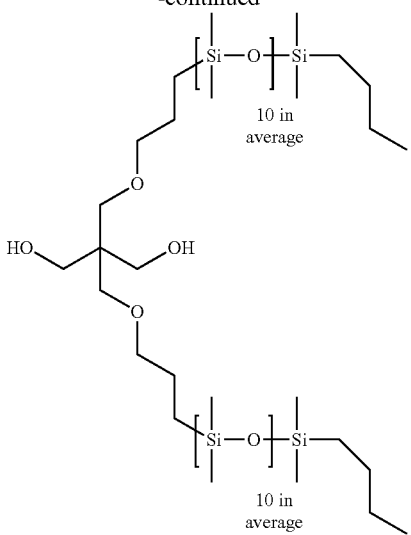
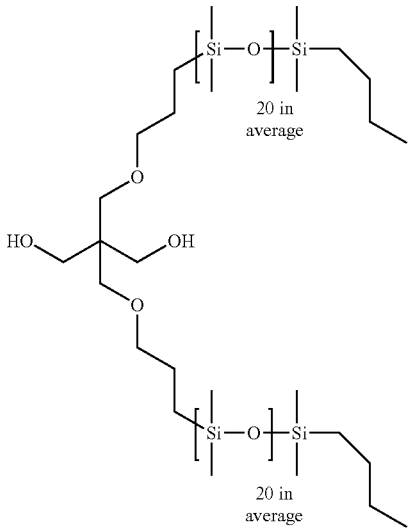
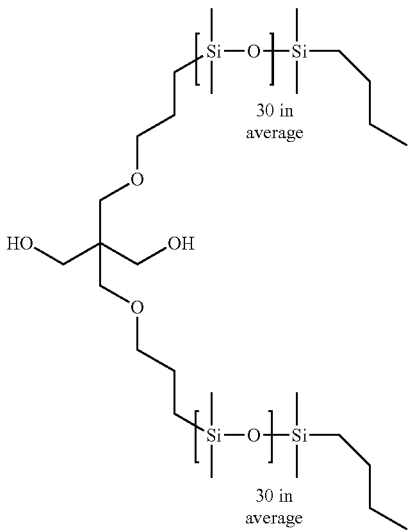

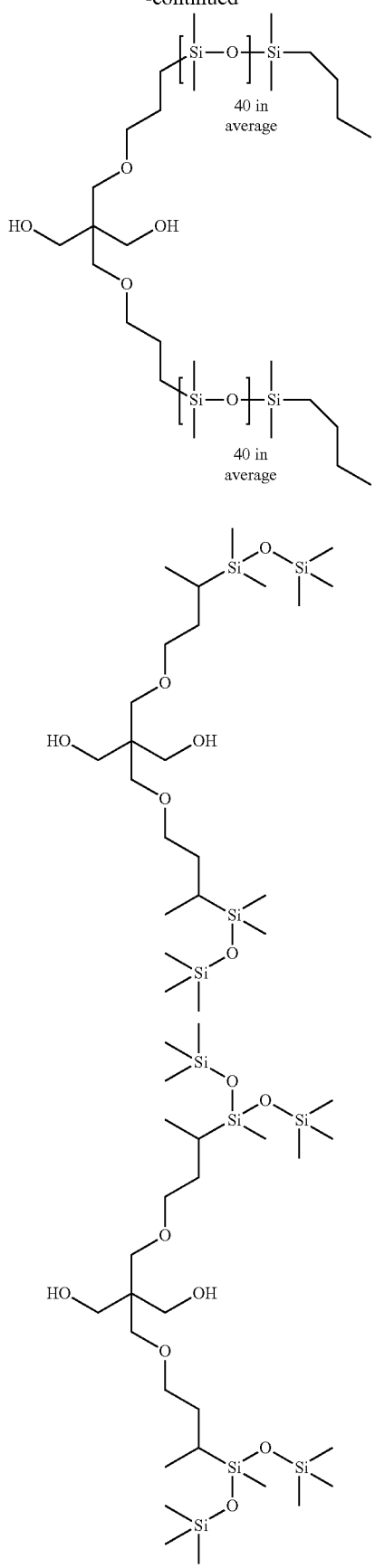

61
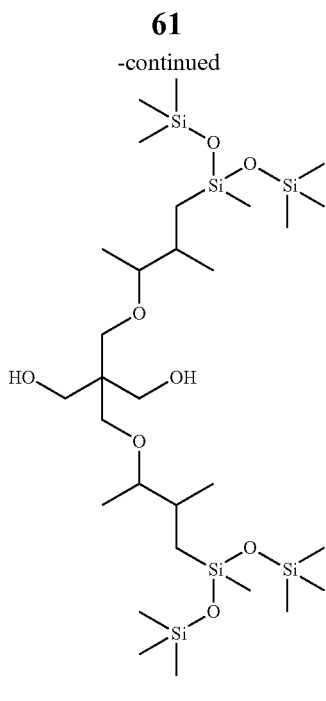
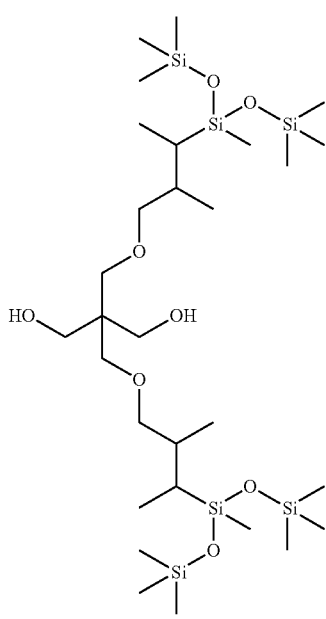
62
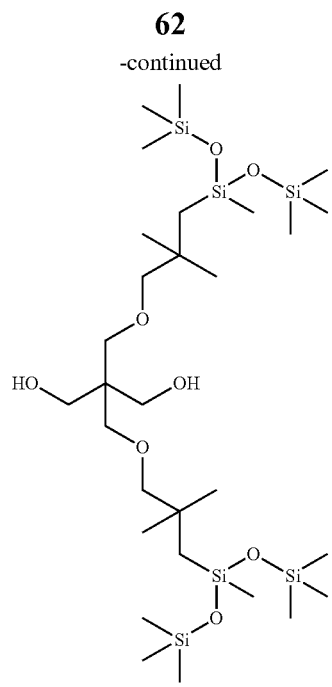
As a compound having isocyanate groups to react with the diol compound shown by the general formulae (2), the following can be specifically illustrated.
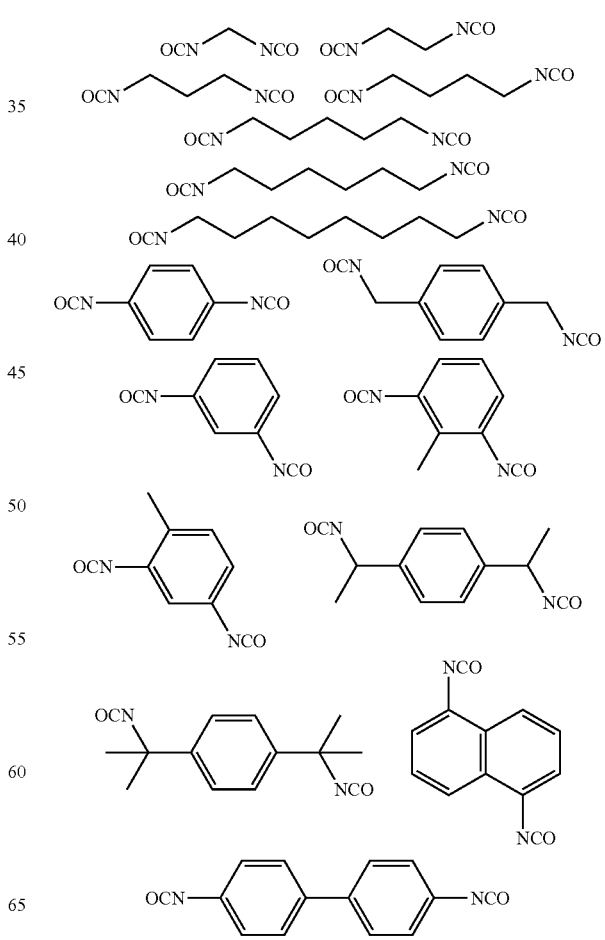

-continued
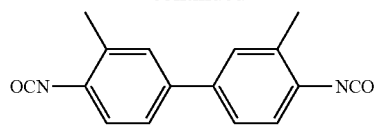
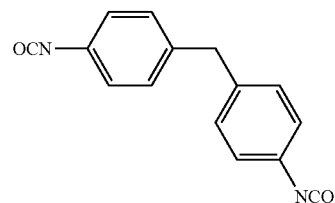
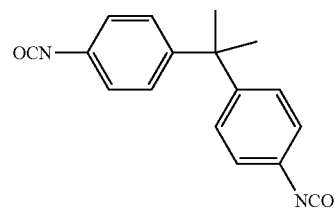
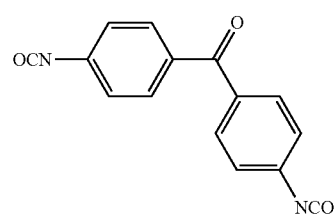
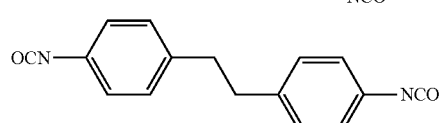
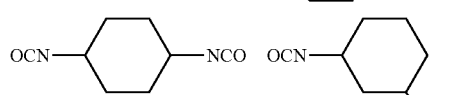
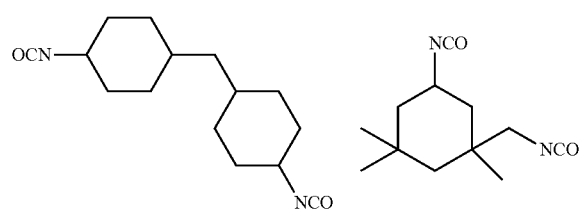
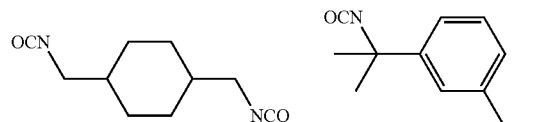
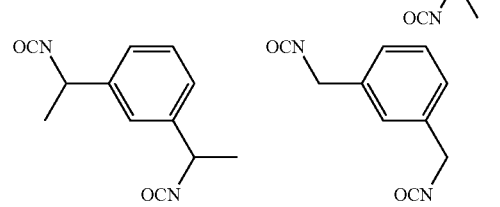
-continued
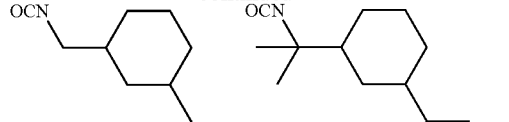
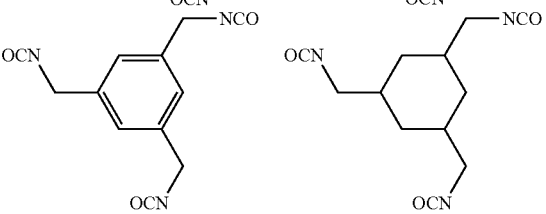
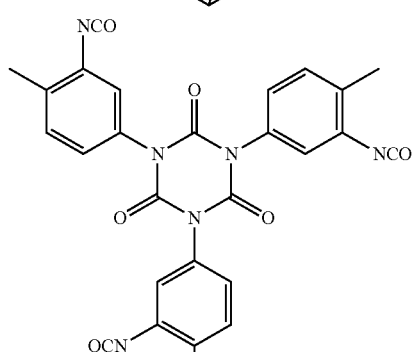
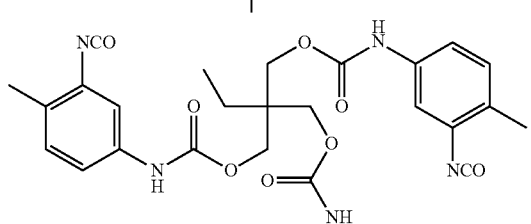
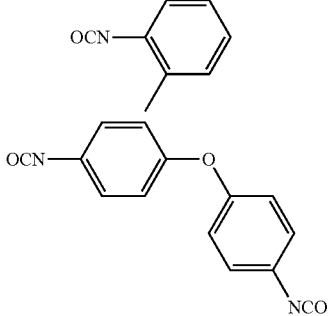
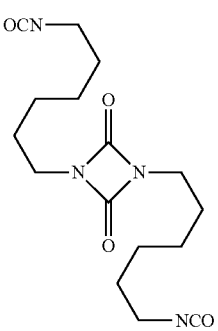
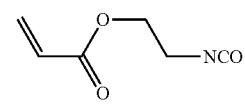

-continued

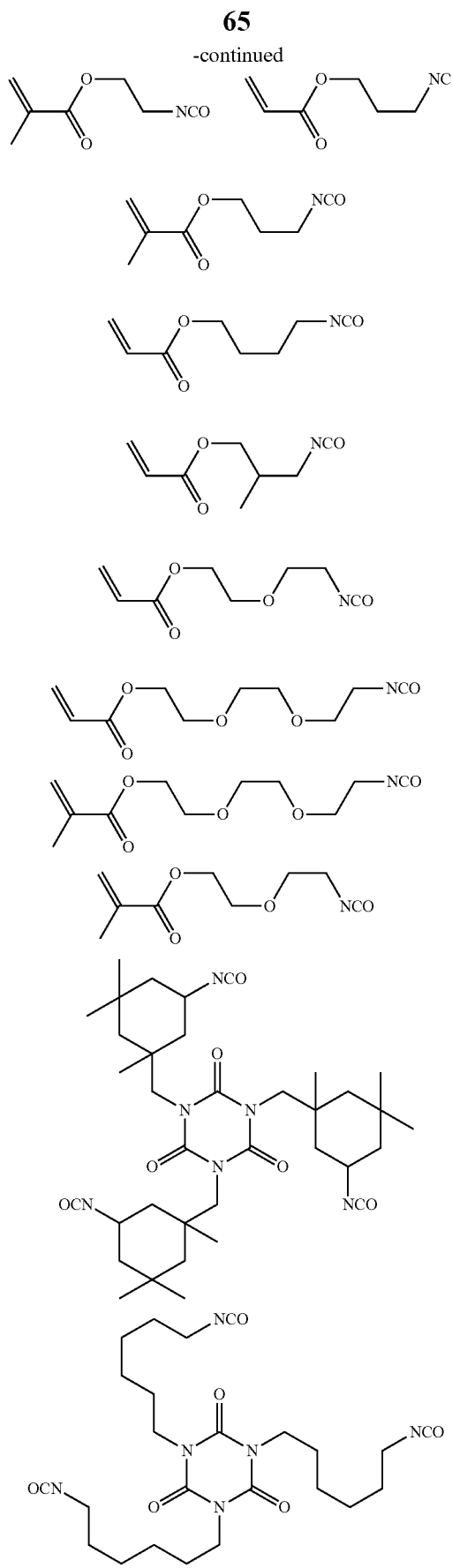

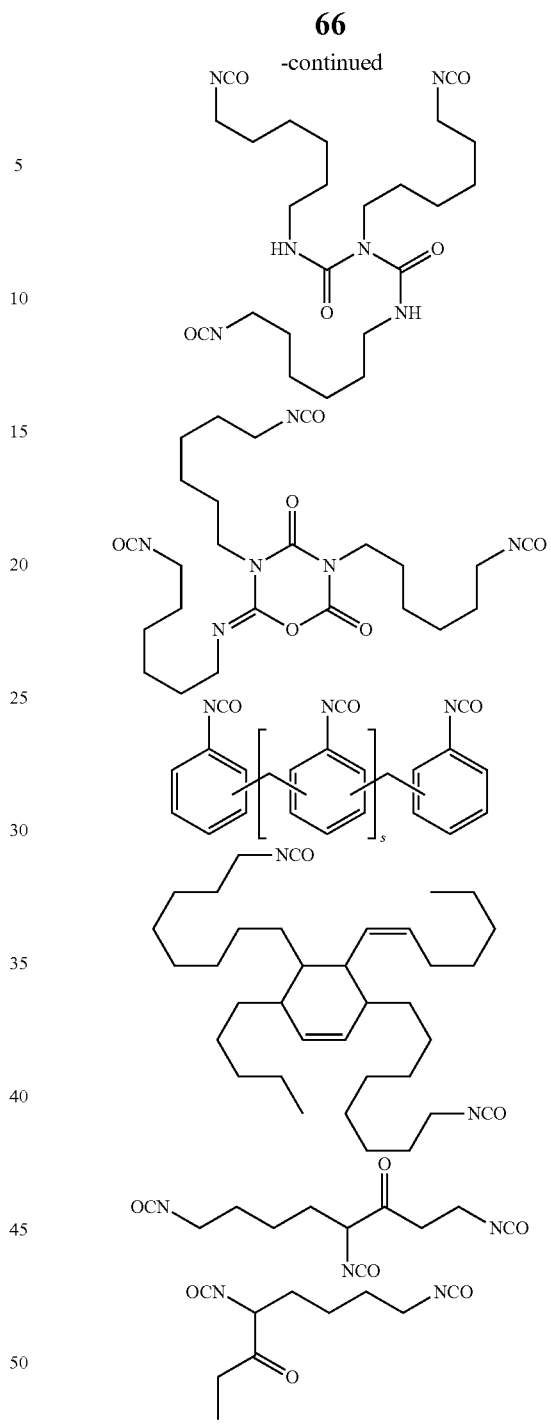

In the formulae, "s" is an integer of 1 or more.

Among the isocyanate compounds described above, especially the compounds having a (meth)acrylate group are allowed to react with a diol compound shown by the general formulae (2) to give a compound having a (meth)acrylate group at the terminal shown by the general formula (3).

The isocyanate compounds described above have higher reactivity with a diol compound shown by the general formula (2) (silicone-pendant diol), and it is important to control the reactivity thereby. The isocyanate compound can react with moisture in the air to inactivate the isocyanate groups during the storage, and has to be carefully stored by sufficient moistureproofing and so on. Accordingly, in order to prevent these phenomena, a compound having a blocked isocyanate group may be used, in which the isocyanate group is protected with a substituent.

The blocked isocyanate group has a blocked group that is deprotected by heating to give an isocyanate group. Illustrative examples thereof include isocyanate groups substituted with alcohol, phenol, thioalcohol, imine, ketimine, amine, lactam, pyrazole, oxime, and β-diketone.

A catalyst may be added to decrease the temperature for deprotecting the blocked isocyanate groups. Illustrative examples of the catalyst include organic tin such as dibutyltin dilaurate, bismuth salt, and zinc carboxylate such as zinc 2-ethylhexanoate and zinc acetate.

In particular, JP 2012-152725A shows that the temperature for deprotection reaction can be reduced by including zinc carboxylate of α,β-unsaturated carboxylic acid as a blocked isocyanate dissociation catalyst.

In addition to the diol compound shown by the general formulae (2) and the compound having isocyanate groups, a compound including a plurality of hydroxy groups may be added. The addition of such a compound having a plurality of hydroxy groups allows chain elongation and intermolecular crosslinking.

Illustrative examples of the compound having a plurality of hydroxy groups include the following.

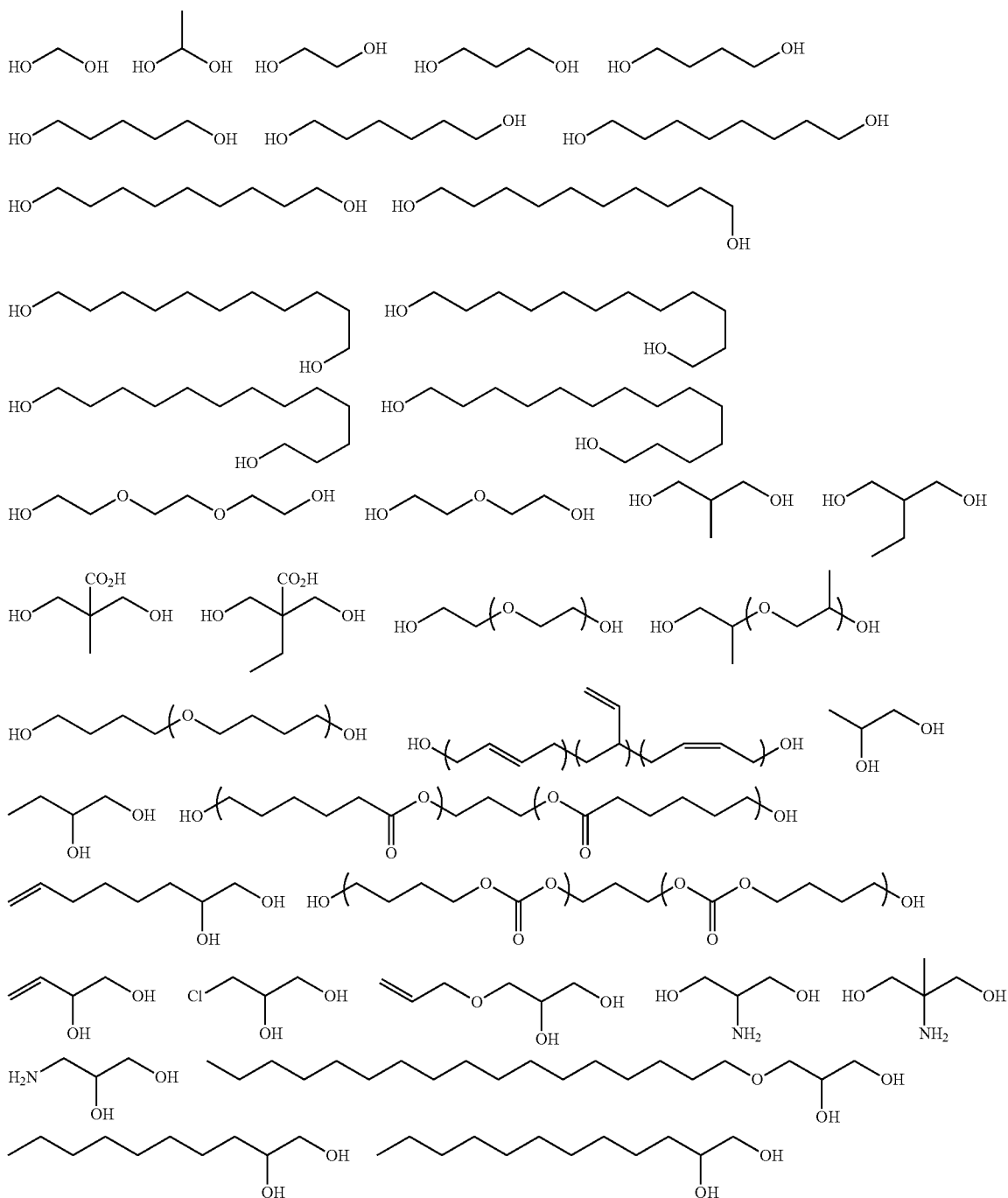

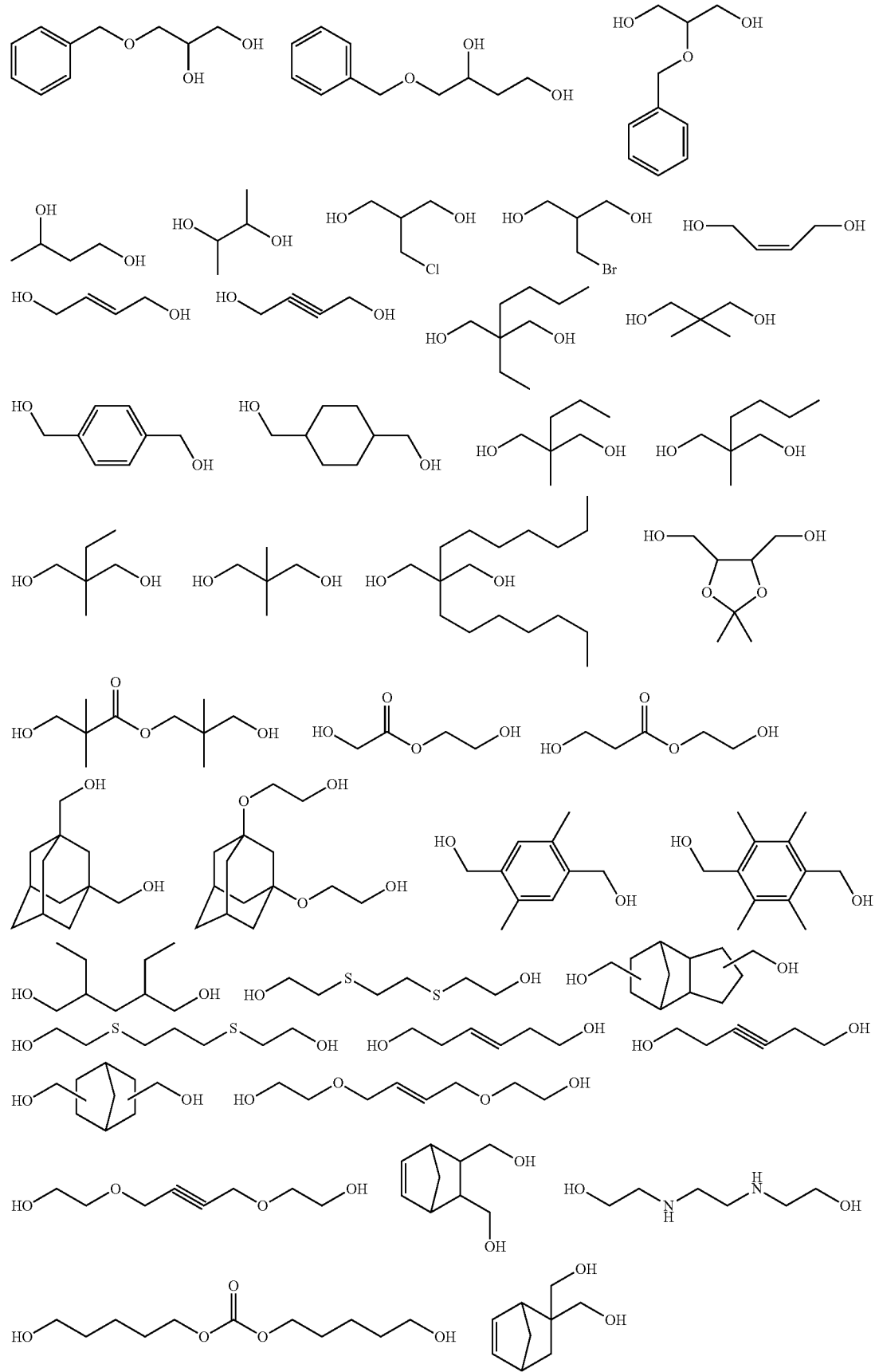

-continued
| 71 | 72 |
|---|---|
| 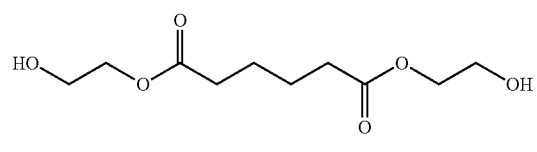 | 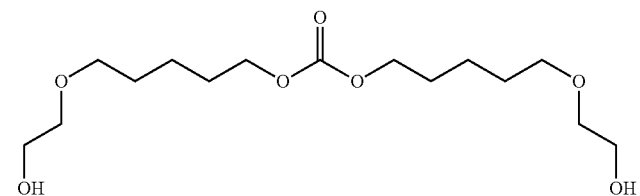 |
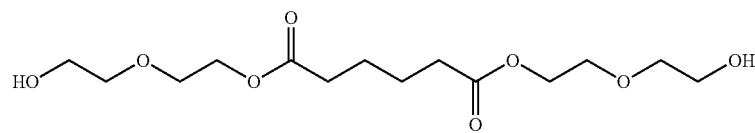
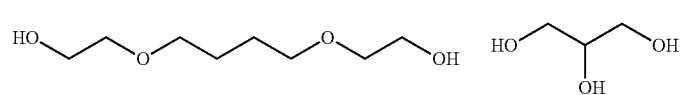 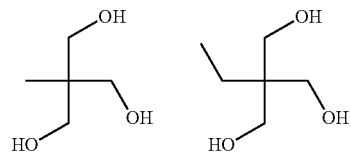
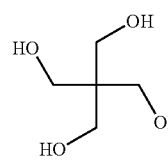 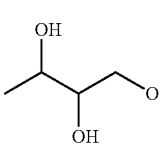 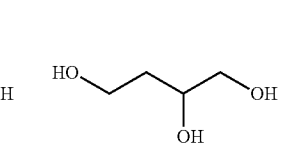 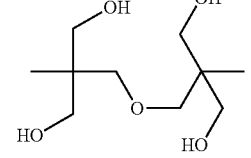
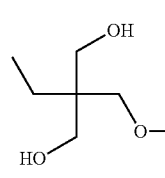 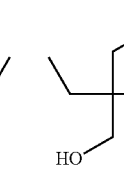 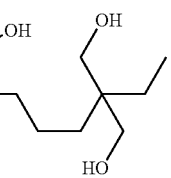 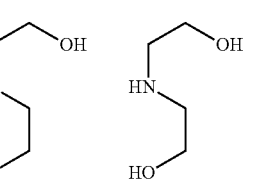 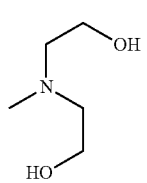
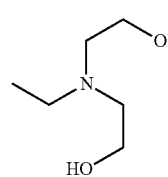 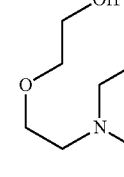 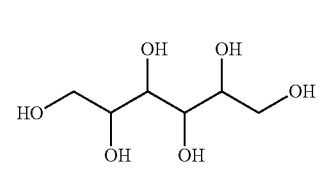
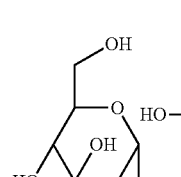 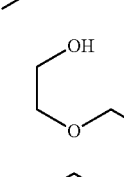 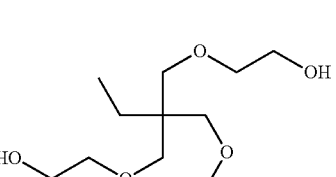
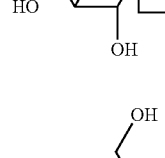 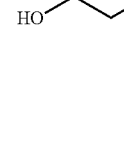 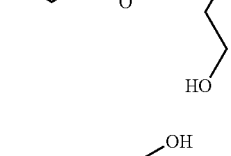
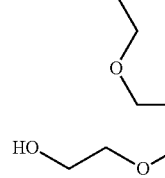 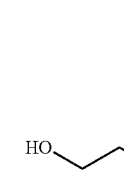 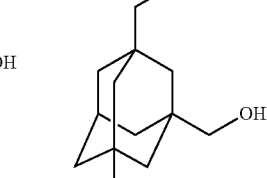

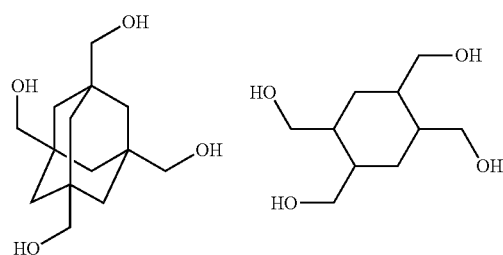
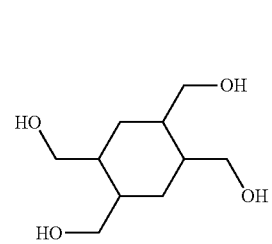
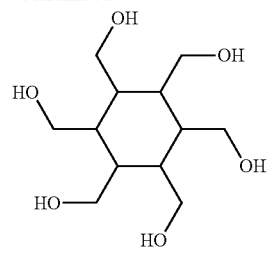
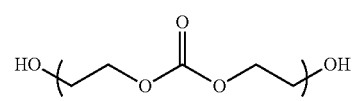
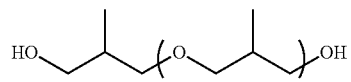
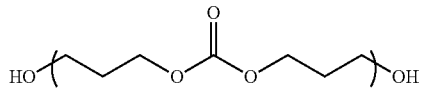
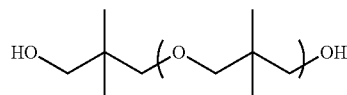
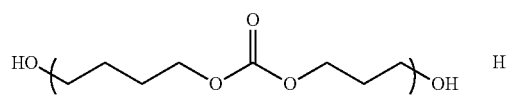
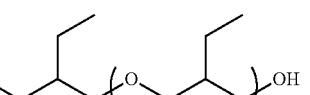
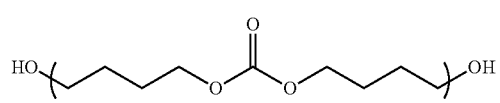
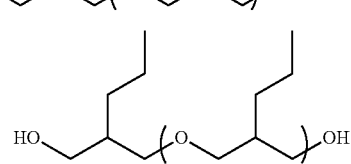
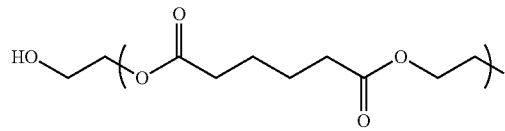
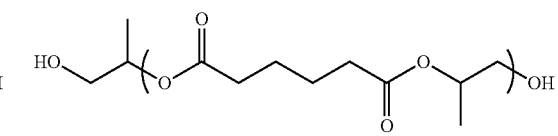
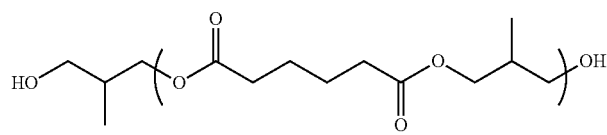
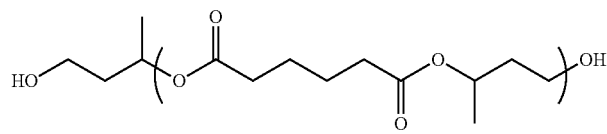
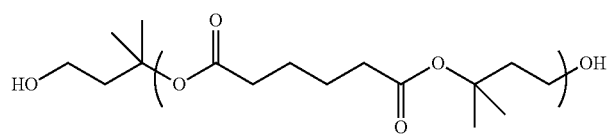
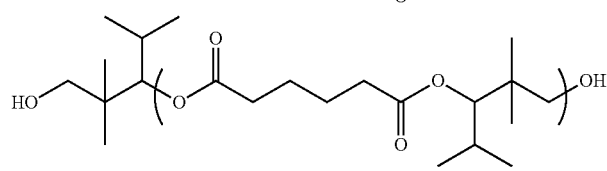
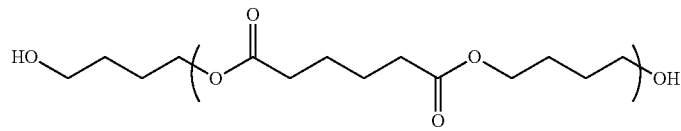
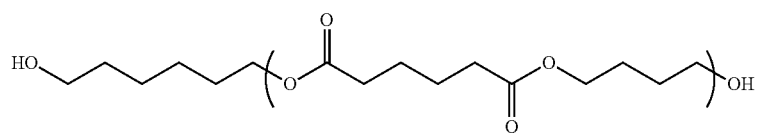
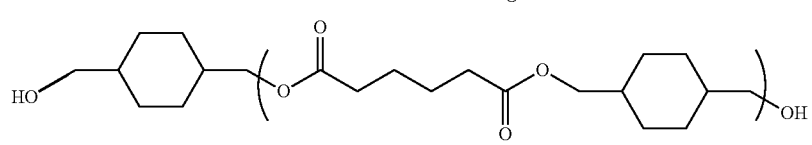

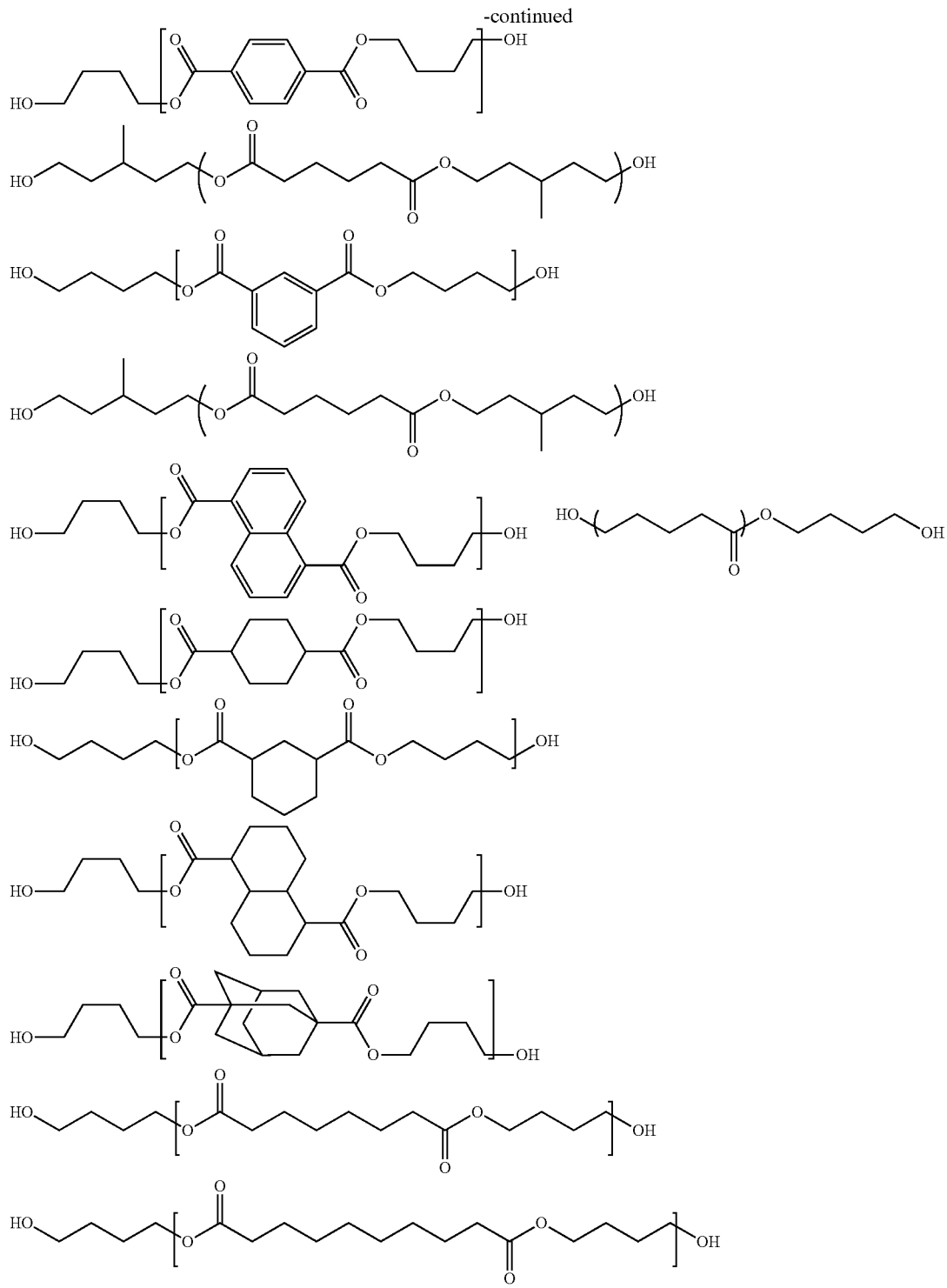

-continued

Additionally, a compound having an amino group can also be added. When an isocyanate group reacts with an amino group, a urea bond is formed. The moiety consisting of a urethane bond and a urea bond is called as a hard segment, and improves the strength through the hydrogen bonds. Thus, the strength is successfully improved by the addition of urea bonds not only by urethane bonds.

The polymer compound preferably has a weight average molecular weight of 500 or more. Such a polymer compound can be favorably used for a urethane-(meth)acrylate resin or a urethane resin for TPU to give the inventive stretchable film as will be described below. The upper limit of the weight average molecular weight is preferably 1,000,000 or less, more preferably 500,000 or less.

The polymer compound preferably has a weight average molecular weight in the range of 500 to 1000000 containing a structure shown by the following general formula (1):

(1)

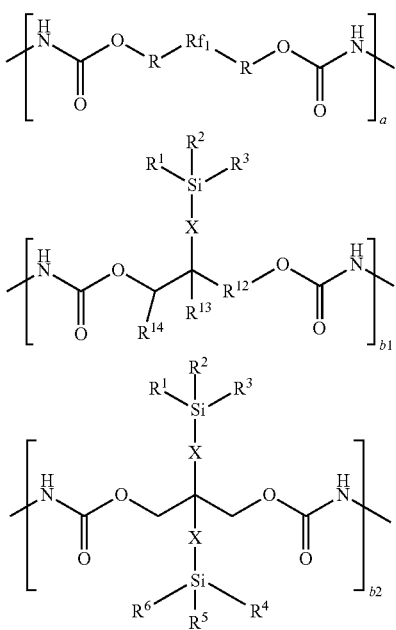

wherein $R^1$ to $R^{14}$, X, $Rf_1$, R, "a", b1, and b2 are as defined above.

The polymer compound is further preferable to contain a structure shown by the following general formula (3):

(3)

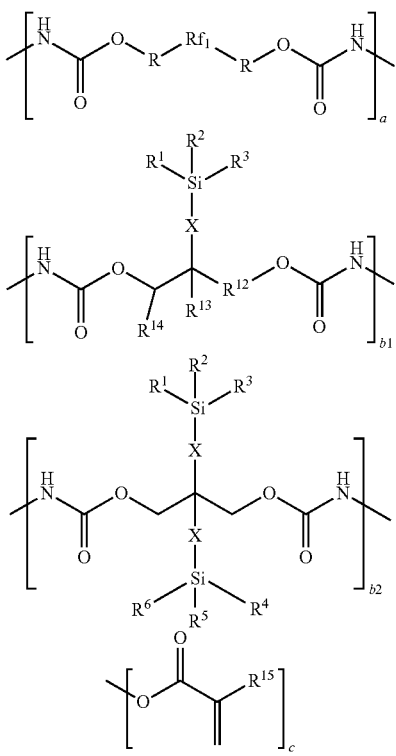

wherein $R^1$ to $R^{15}$, X, $Rf_1$, R, "a", "b1", "b2", and "c" are as defined above.

The polymer compound like this can give a favorable stretchable film having excellent strength.

[Cured Product of Resin]

The stretchable film of the present invention is a cured product of a resin containing the polymer compound described above. The method (curing method) for turning the resin to a cured product include the following.

As a curing method of the polyurethane base resin having a fluoroalkyl group or a fluoroalkylene group and silicone of the present invention, a one-shot process can be exemplified in which a hydroxy compound, an isocyanate compound, a diol compound containing a fluoroalkyl group or a fluoroalkylene group, and a diol compound having silicone are mixed and cured by heating. The one-shot method has an advantage of higher productivity.

Another example is a prepolymer process in which a hydroxy compound and an isocyanate compound are previously mixed, followed by mixing the hydroxy compound and the isocyanate compound additionally, together with a diol compound containing a fluoroalkyl group or a fluoroalkylene group and a diol compound having a silicone pendant(s) to cure the same. In this case, the hydroxy group and the isocyanate group have reacted sufficiently, thereby making it possible to form a film having higher strength and higher stretchability with lower rate of the remained isocyanate groups. In preparing the prepolymer, it is also possible to mix the both of or either of the diol compound containing a fluoroalkyl group or a fluoroalkylene group and the diol compound having a silicone pendant(s) in addition to the hydroxy compound and the isocyanate compound, not only the latter. In preparing the prepolymer, it is preferable to mix excess amount of isocyanate groups, whereby the prepolymer is allowed to have isocyanate terminals.

Incidentally, the stretchable film can also be formed by synthesizing the urethane-(meth)acrylate polymer and adding a radical generator thereto, followed by crosslinking with radicals generated by light irradiation or heating as will be described below.

The crosslinking through polymerization of (meth)acrylate allows the urethane film to attain the strength by covalent bond of crosslinking through acryl groups not only by hydrogen bond of urethane, thereby being free from heat deformation and having characteristics of less lowering the strength in repeated expansion and contraction test.

For the reaction to form urethane, it is possible to add a catalyst, such as an organic tin compound, an organic bismuth compound, an organic aluminum compound, an organic titanium compound, an organic zirconium compound, a tertiary amine compound, and a quaternary ammonium compound.

[Tensile Strength of Stretchable Film]

The inventive stretchable film preferably has a stretching property (in other words, stretchability or elongation) of 40 to 1000% in a tensile test regulated by JIS K6251. With such a stretching property, the stretchable film can be particularly preferably used as a coating film of a stretchable wiring.

[Use of Stretchable Film]

The inventive stretchable film is preferably used for a film to be in contact with a conductive wiring having stretchability. The inventive stretchable film can be favorably used especially for such applications.

The inventive stretchable film described above has excellent stretchability and strength that are equivalent to those of polyurethane, with the film surface having excellent water repellency equivalent to that of silicone.

<Method for forming Stretchable Film>

The present invention also provides a method for forming the stretchable film by mixing a diol compound shown by the general formulae (2) and a compound having an isocyanate group(s), forming a film from the mixture, and curing the film by heating.

One example of the method for forming a stretchable film is a method of mixing a diol compound shown by the general formula (2), together with a protected or unprotected isocyanate compound, a compound having a plurality of hydroxy groups for chain elongation or crosslinking, and in some cases, a compound including an amino group; and applying this mixture to a substrate for peeling (release substrate) to form a film, followed by heat curing.

In this method, a polymer network is formed with increasing the molecular weight while forming urethane bonds through reaction of isocyanate and alcohol. In case of adding a compound that has three or more of hydroxy groups or isocyanate groups, crosslinking reaction proceeds to lower the stretchability, but improve the film strength. Accordingly, it is possible to control the hardness, the stretchability, and the strength by controlling the amount of the compound having two or three hydroxy groups or isocyanate groups. Additionally, an independent stretchable film can be obtained by peeling the film from the substrate after being cured.

Regarding the ratio of molar number of hydroxy group and isocyanate group in the mixture, it is preferable that the hydroxy groups and the isocyanate groups be in the same molar amount, or the molar number of hydroxy groups be larger, that is, the value of the molar number of hydroxy groups divided by the molar number of isocyanate groups be 1 or more. When the isocyanate groups are smaller, carbon dioxide cannot be formed through the reaction of excess isocyanate groups with water, thereby allowing the film to be prevented from the risk of causing voids due to foaming. In general, foamed urethane is produced with excess isocyanate groups. In the inventive stretchable film, however, improved strength is required, and the film is preferably free from void due to foaming thereby.

When the resin in the inventive stretchable film is formed in condition that the molar number of alcohol groups is larger than that of isocyanate groups as described above, a part of the polymer terminals has a structure in which a urethane bond is formed only at one side of a diol compound shown by the general formula (2) to make the other side be alcohol.

The heating temperature is in the range of room temperature to 200° C., preferably in the range of 40 to 160° C. for 5 seconds to 60 minutes. Since isocyanate groups react with moisture in the air, the heating is preferably performed in dry air, under nitrogen atmosphere, or while covering the surface with a release film. The heat curing may be performed by covering either side or the both sides of a film with a release film(s). The covering is preferably performed at one side in curing while winding the film on a roll or at the both sides in batch curing, though the method is not limited thereto.

The stretchable film can also be formed by forming a film from the compound having a (meth)acrylate group(s) at the terminal shown by the general formula (3), followed by heating and/or light irradiation to cure the same. The compound having a (meth)acrylate group(s) at the terminal can be synthesized by mixing a diol compound shown by the general formulae (2) with a protected or unprotected isocyanate compound, a compound having a plurality of hydroxy groups for chain elongation or crosslinking, and (meth)acrylate having a hydroxy group(s) or protected or unprotected isocyanate groups, followed by polymerization to synthesize a urethane polymer having a polymer terminal(s) of a (meth)acrylate, which can be used for forming the stretchable film. In this case, crosslinking is performed by reaction of (meth)acrylate moieties with a radical. As a method for radical crosslinking, addition of a radical generator is desirable. The radical generator includes a thermal-radical generator, which generates a radical by thermal decomposition, and a photo-radical generator, which generates a radical by light irradiation.

Illustrative examples of the thermal-radical generator include an azo radical generator and a peroxide radical generator. Illustrative examples of the azo radical generator include 2,2'-azobisisobutyronitrile (AIBN), 2,2'-azobis(2,4-dimethylvaleronitrile), dimethyl 2,2'-azobis(2-methylpropionate), 2,2'-azobis(4-methoxy-2,4-dimethylvaleronitrile), 2,2'-azobis(cyclohexane-1-carbonitrile), and 4,4'-azobis(4-cyanovaleric acid). Illustrative examples of the peroxide radical generator include benzoyl peroxide, decanoyl peroxide, lauroyl peroxide, succinyl peroxide, t-butylperoxy-2-ethylhexanoate, t-butylperoxypivaloate, and 1,1,3,3-tetramethylbutylperoxy-2-ethylhexanoate.

Illustrative examples of the photo-radical generator include acetophenone, 4,4'-dimethoxybenzyl, benzyl, benzoin, benzophenone, 2-benzoylbenzoic acid, 4,4'-bis(dimethylamino)benzophenone, 4,4'-bis(diethylamino)benzophenone, benzoin methyl ether, benzoin ethyl ether, benzoin isopropyl ether, benzoin butyl ether, benzoin isobutyl ether, 4-benzoylbenzoic acid, 2,2'-bis(2-chlorophenyl)-4,4',5,5'-tetraphenyl-1-2'-biimidazole, methyl 2-benzoylbenzoate, 2-(1,3-benzodioxole-5-yl)-4,6-bis(trichloromethyl)-1,3,5-triazine, 2-benzyl-2-(dimethylamino)-4'-morpholinobutyrophenone, 4,4'-dichlorobenzophenone, 2,2-diethoxyacetophenone, 2,2-dimethoxy-2-phenylacetophenone, 2,4-diethylthioxanthen-9-one, diphenyl(2,4,6-trimethylbenzoyl)phosphine oxide, 1,4-dibenzoylbenzene, 2-ethylanthraquinone, 1-hydroxycyclohexyl phenyl ketone, 2-hydroxy-2-methylpropiophenone, 2-hydroxy-4'-(2-hydroxyethoxy)-2-methylpropiophenone, 2-isonitrosopropiophenone, 2-phenyl-2-(p-toluenesulfonyloxy)acetophenone (BAPO), and camphorquinone.

It is to be noted that the loading amount of the thermal-radical generator or the photo-radical generator is preferably in the range of 0.1 to 50 parts by mass based on 100 parts by mass of the resin.

It is also possible to add a crosslinking agent that has a plurality of (meth)acrylate or thiol. This makes it possible to improve the efficiency of radical crosslinking.

It is also possible to add a monomer that has an alkyl group or an aryl group, or a monomer that has an alkyl group or an aryl group substituted with a silicon-containing group or a fluorine. This makes it possible to decrease the viscosity of the solution to form a stretchable film with thinner thickness. When these monomers each have a polymerizable double bond, they can be fixed into the film in curing the film.

Illustrative examples of the monomer that has an alkyl group or an aryl group include isobornyl acrylate, lauryl acrylate, tetradecyl acrylate, stearyl acrylate, isostearyl acrylate, behenyl acrylate, adamantane acrylate, phenoxyethylene glycol acrylate, and phenoxydiethylene glycol acrylate, but not particularly limited thereto.

In case of forming a stretchable film using a compound having a (meth) acrylate group(s) at the terminal(s), the curing can be performed by combining heat curing and photo-curing. For example, it is possible to form a stretchable film as a base previously by heat curing and to form another stretchable film thereon by photo-curing. The photo-curing has advantages to make heating inessential and the curing time shorter, together with a disadvantage of being unable to cure the portions that cannot receive light. By a combination of heat curing and photo-curing, it becomes possible to select a curing method to make use of each advantage.

The methods of forming the stretchable film include a method of applying the composition onto a planer substrate or a roll. Illustrative examples of the method for applying the composition include spin coating, bar coating, roll coating, flow coating, dip coating, spray coating, doctor coating, and gravure coating. The coating is preferably performed so as to have a coating film thickness of 1 µm to 2 mm.

For sealing a part with unevenness, it is preferable to use a method such as roll coating and spray coating, a method of screen printing to coat a part that requires to be coated, etc. In order to perform various coating or printing, the viscosity of the mixed solution have to be controlled. When lower viscosity is required, an organic solvent may be added; when higher viscosity is required, filler such as silica is mixed.

The organic solvent preferably has a boiling point in the range of 115 to 200° C. at atmospheric pressure. Specifically, it is preferable to use one or more organic solvents selected from 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, amyl acetate, butenyl acetate, isoamyl acetate, phenyl acetate, propyl formate, butyl formate, isobutyl formate, amyl formate, isoamyl formate, methyl valerate, methyl pentenoate, methyl crotonate, ethyl crotonate, propylene glycol monomethyl ether, ethylene glycol monomethyl ether, propylene glycol monoethyl ether, ethylene glycol monoethyl ether, propylene glycol dimethyl ether, diethylene glycol dimethyl ether, propylene glycol monomethyl ether acetate, and propylene glycol monoethyl ether acetate.

In case of curing the compound that has a (meth)acrylate group at the terminal by heating, the heat curing can be performed with a hot plate, in an oven, or by irradiation with far infrared ray, for example. The heating condition is preferably at 30 to 150° C. for 10 seconds to 60 minutes, more preferably 50 to 120° C. for 30 seconds to 20 minutes. The baking may be performed in any environment such as in the atmosphere, in an inert gas, or in vacuum.

In case of curing the compound that has a (meth)acrylate group at the terminal by light irradiation, the light irradiation is preferably performed with a light having a wavelength of 200 to 500 nm. As the light source, a halogen lamp, a xenon lamp, excimer laser, and LED can be used, for example. Irradiation with electron beam is also preferable. The irradiation quantity is preferably in the range of 1 mJ/cm$^2$ to 100 J/cm$^2$.

Illustrative example thereof also includes a method of synthesizing an ultra-high-molecular-weight urethane polymer, followed by heating the same to form a sheet. The thermoplastic urethane like this is called TPU and attains strength through hydrogen bonds between the urethane polymers. TPU is not crosslinked, but possesses higher strength due to the strong hydrogen bonds in urethane. On the other hand, the film causes to deform by repeating expansion and contraction of the film to lower the strength. This is because the repeating of expansion and contraction replaces the positions of the hydrogen bonds between molecules as in thermal deformation.

The urethane film crosslinked through polymerization of (meth)acrylate attains the strength through covalent bonds of acrylic crosslinking not only through hydrogen bonds in urethane, thereby being free from thermal deformation and featured to lessen the lowering of the strength in a repeated expansion and contraction test.

For the reaction to form urethane, it is possible to add a catalyst, such as an organic tin compound, an organic bismuth compound, an organic aluminum compound, an organic titanium compound, an organic zirconium compound, a tertiary amine compound, and a quaternary ammonium compound.

The urethane-(meth)acrylate resin or the urethane resin for TPU preferably has a weight average molecular weight of 500 or more. Such a resin can be favorably used for the stretchable film of the present invention. The resin favorably has the upper limit of the weight average molecular weight of 1,000,000 or less, more preferably 500,000 or less.

The inventive method for forming a stretchable film described above makes it possible to easily form a stretchable film having excellent stretchability and strength that are equivalent to or superior to those of polyurethane, together with very high water repellency on the film surface.

[Application Example of Stretchable Film]

Figure 2:
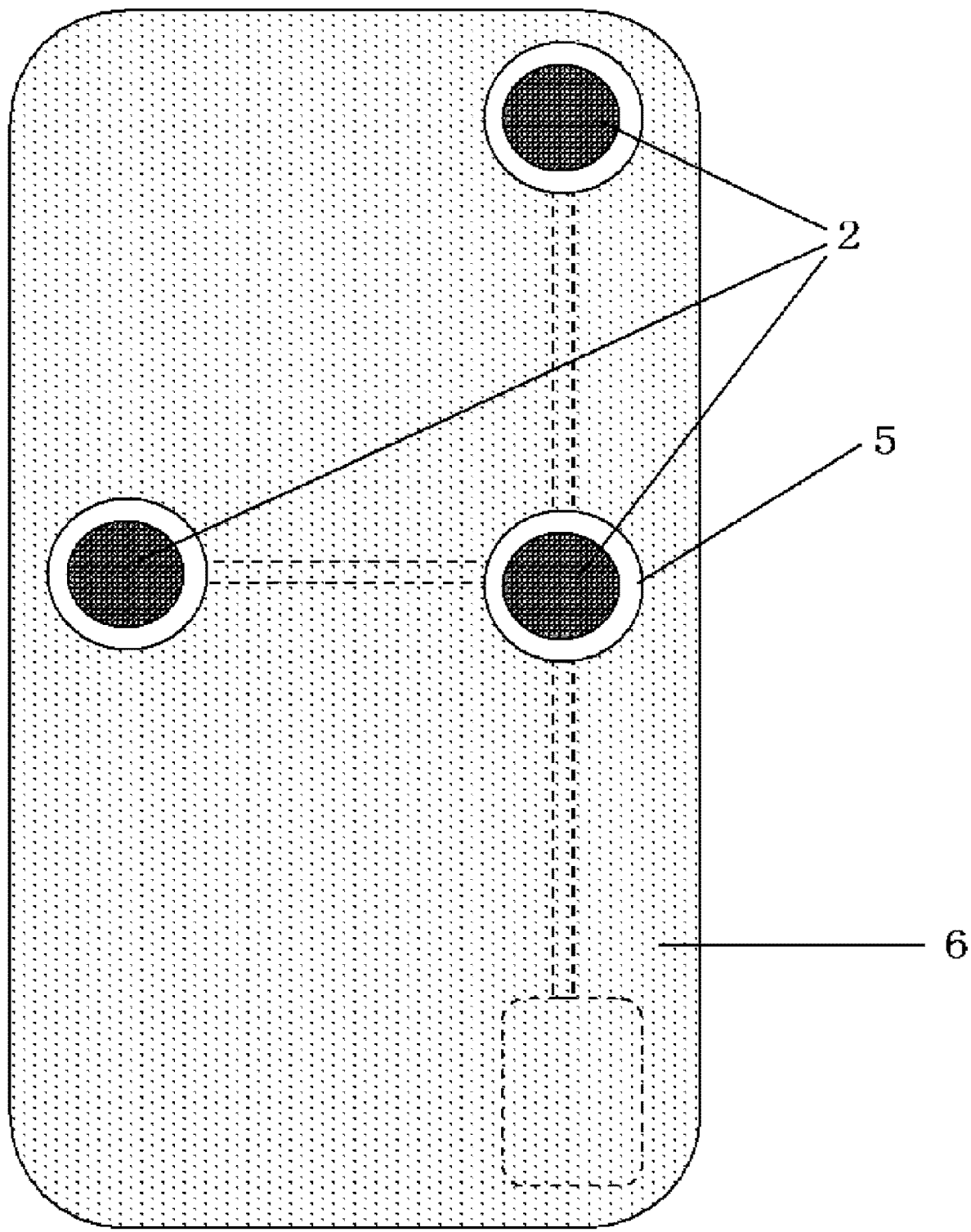
FIG. 2 is a schematic view of the electrocardiograph in FIG. 1 viewed from the bio-electrode.
Figure 3:
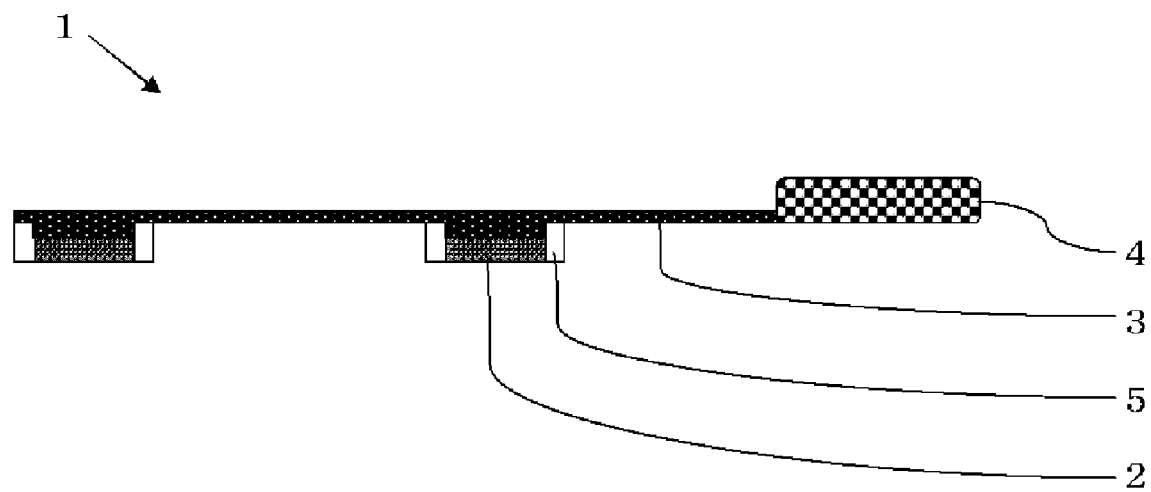
FIG. 3 is a cross-sectional view showing an electrocardiograph before being covered with the inventive stretchable film.
Figure 4:
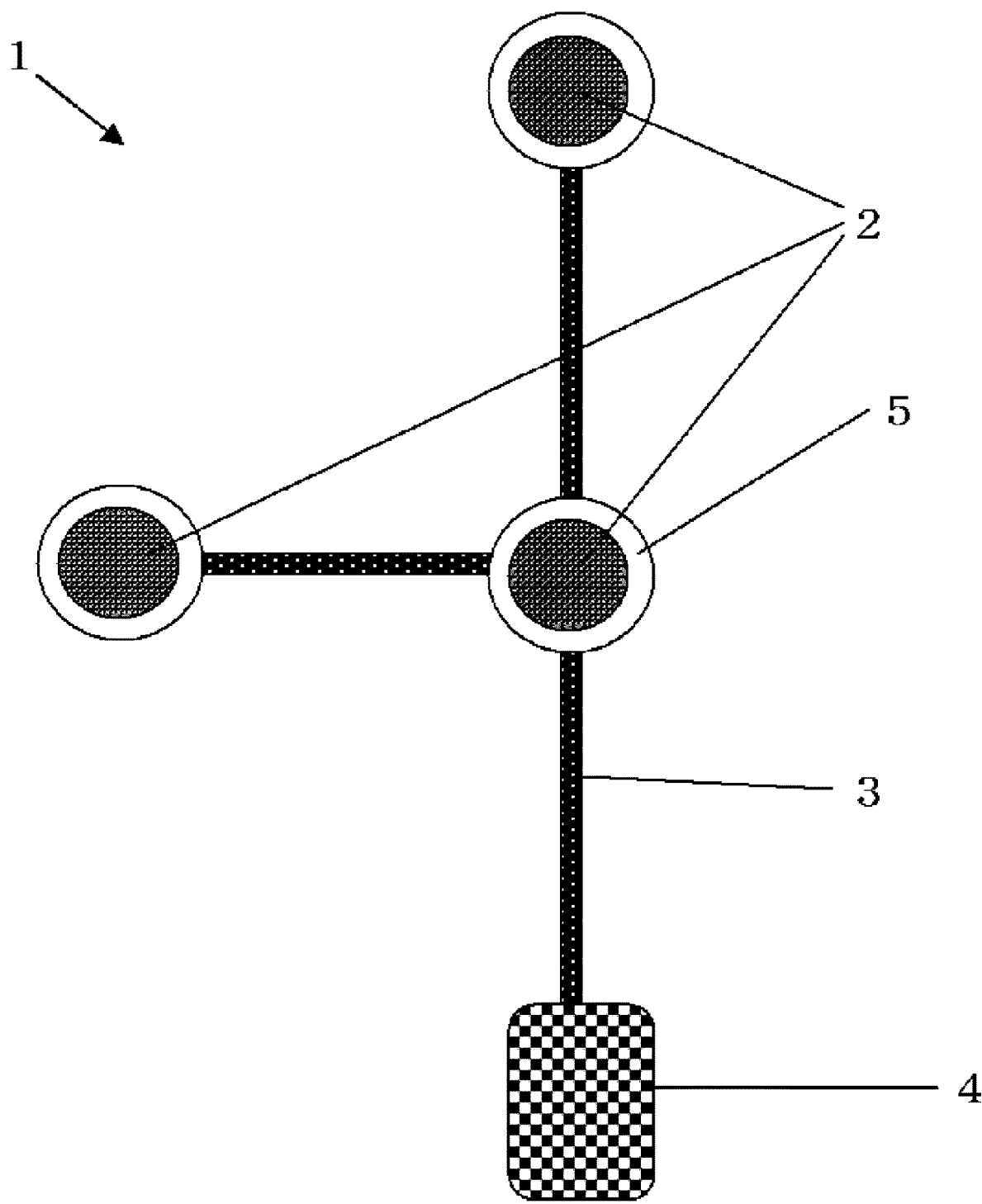
FIG. 4 is a schematic view of the electrocardiograph in FIG. 3 viewed from the bio-electrode.

Application examples of the inventive stretchable film are shown in FIGS. 1 to 9. FIG. 1 is a sectional view of an electrocardiograph covered with the inventive stretchable film, and FIG. 2 is a schematic view of the electrocardiograph in FIG. 1 viewed from the bio-electrode. FIG. 3 is a cross-sectional view showing an electrocardiograph before being covered with the inventive stretchable film, FIG. 4 is a schematic view of the electrocardiograph in FIG. 3 viewed from the bio-electrode, and the electrocardiograph in FIGS. 3 and 4 is the one described in Patent Document 1. As shown in FIGS. 3 and 4, in the electrocardiograph 1, three bio-electrodes 2 are linked to the wiring 3, which conducts electric signals, and are connected to the center device 4.

As the wiring 3, electrically conductive material and electrically conductive polymer material are generally used, including metal such as gold, silver, platinum, titanium, stainless, copper, and alloys thereof as well as carbon. The wiring can be a meandering-shape as described in Patent Literature 1 to provide stretchability, and can be formed by pasting powder of the electrically conductive material or wire of the electrically conductive material on a stretchable film, printing electrically conductive ink that contains the electrically conductive material on a stretchable film, or using an electrically conductive fabric in which electrically conductive material and fibers are combined.

The electrocardiograph 1 have to be stuck to skin. Accordingly, in FIGS. 3 and 4, the self-adhesive part 5 is disposed around the bio-electrode 2 in order not to separate the bio-electrode 2 from skin. Incidentally, when the bio-electrode 2 has self-adhesiveness, the surrounding self-adhesive part 5 is inessential.

This electrocardiograph 1 is covered with the stretchable film 6, which is the inventive stretchable film, as shown in FIG. 1. As shown in FIG. 2, however, the bio-electrode 2 and the self-adhesive part 5 have to be stuck to the skin and are not covered with the stretchable film 6 thereby.

When the electrocardiograph 1 is covered with the stretchable film 6, it is possible to cover the back and front sides of the electrocardiograph 1 simultaneously, or cover each side one by one. The bio-electrode 2 and the self-adhesive part 5, which will be in contact with skin, have to be left uncovered, the electrocardiograph 1 covered with the stretchable film 6 as shown in FIG. 1 can be obtained such that the electrocardiograph 1 is placed on a substrate 7 with releasability so as to be in contact with the self-adhesive part 5 and is covered with a stretchable film material as shown in FIG. 5, for example, and the material is cured by light or heat to form the stretchable film 6, followed by being separated from the substrate 7.

Figure 6:
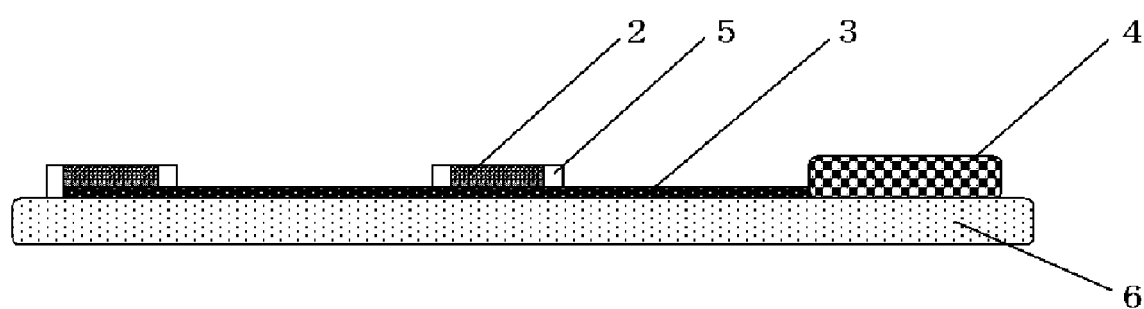
FIG. 6 is a cross-sectional view showing the inventive stretchable film on which a bio-electrode, a self-adhesive part, and wiring are formed, and a center device is connected thereto.
Figure 7:
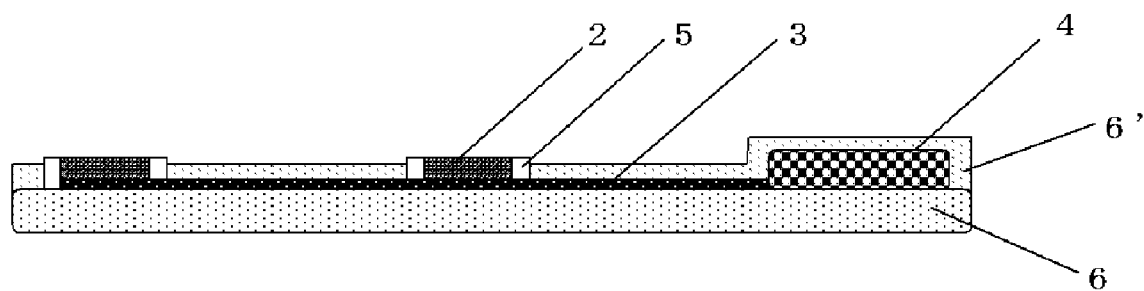
FIG. 7 is a sectional view showing the wiring and the center device in FIG. 6 covered with the inventive stretchable film.

Additionally, it is also possible to exemplify a method in which the bio-electrode 2, the self-adhesive part 5, and the wiring 3 are formed on the stretchable film 6 to connect the center device 4 as shown in FIG. 6, and then stretchable film material is applied thereon and is cured to form a stretchable film 6' as shown in FIG. 7. In this case, the bio-electrode 2, the self-adhesive part 5, and the wiring 3 may be formed on the stretchable film 6 that has been formed on the releasable substrate 7.

Figure 8:
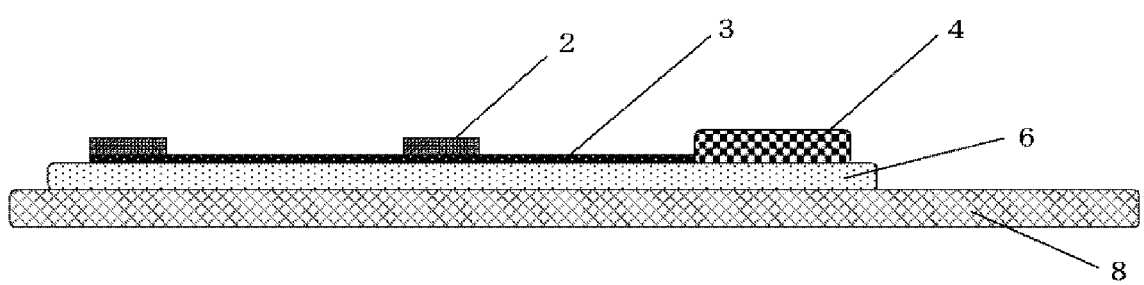
FIG. 8 is a sectional view showing the inventive stretchable film formed on a fabric, having wiring and an electrode formed thereon, together with a center device connected thereto.
Figure 9:
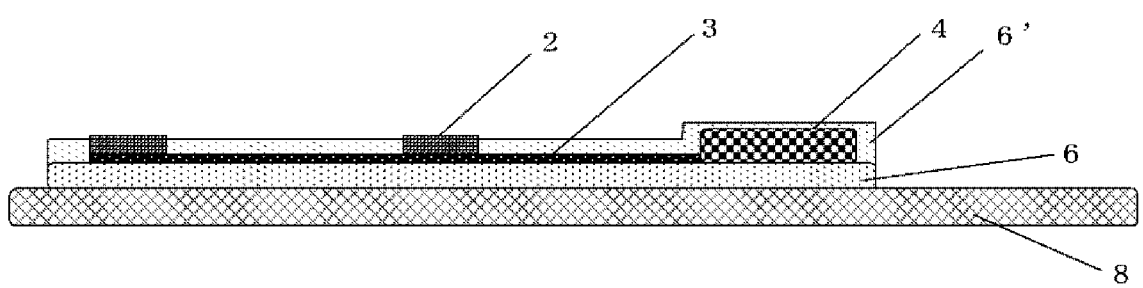
FIG. 9 is a sectional view showing the wiring and the center device in FIG. 8 covered with the inventive stretchable film.

Additionally, it is also possible to form the stretchable film 6 on a fabric 8, followed by forming the bio-electrode 2 and the wiring 3 thereon to connect the center device 4 as shown in FIG. 8, and to form the stretchable film 6' thereon to coat the wiring 3 and the center device 4 as shown in FIG. 9. In this case, the cloth equipped with the device is possibly washed. Accordingly, the inventive stretchable film is required to have higher mechanical strength, water resistance, stretchability, adhesion to a cloth, adhesion to a device, and sealing properties of a device that are durable to washing.

Figure 5:
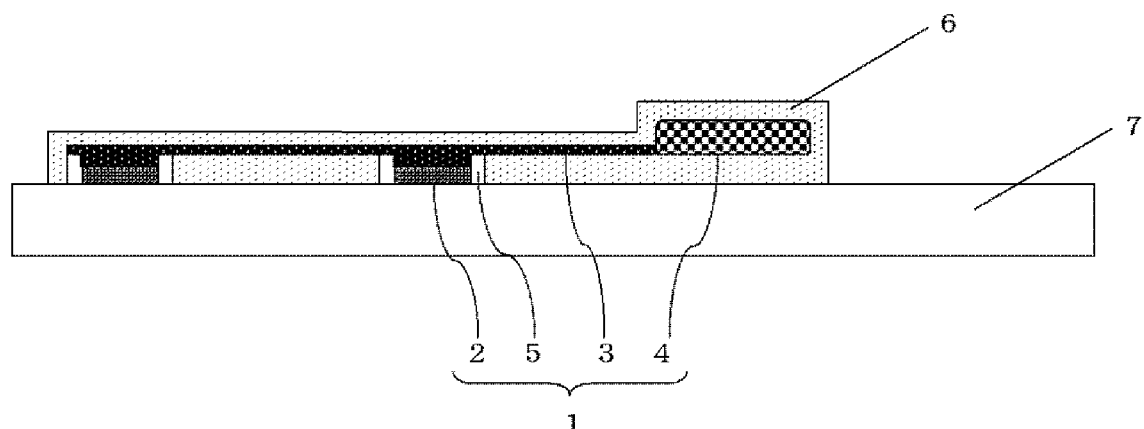
FIG. 5 is a cross-sectional view showing the state in which an electrocardiograph is in contact with a substrate and covered with the inventive stretchable film.

Incidentally, when the stretchable film is formed on parts having unevenness as shown in FIGS. 5, 7, and 9, the above described methods are preferable, such as roll coating, spray coating, and a method by screen printing to coat a part that is required to be coated, etc.

Alternatively, when the stretchable film 6' is formed on the stretchable film 6 as shown in FIGS. 6 to 9, the use of a compound shown by the general formula (3) makes it possible to form the stretchable film 6 previously by heat curing, and to form the stretchable film 6' thereon by photo-curing.

The inventive urethane polymer having a urethane bond shown by the general formula (1) can be used for fiber not only for forming a stretchable film. The fiber can be woven to form a stretchable cloth or formed to a nonwoven fabric. Alternatively, the inventive urethane polymer can be used for coating polyester or cotton, and a cloth or a nonwoven fabric can be obtained therefrom.

The urethane polymer having a urethane bond shown by the general formula (1) can be formed to urethane gel. By decreasing the crosslinking density, gel can be formed to have higher water repellency, high stratchability, high modulus, and lower hardness. Soft gel gives a comfortable feeling and ability to repel perspiration or water.

EXAMPLES

Hereinafter, the present invention will be specifically described with reference to Examples and Comparative Examples, but the present invention is not limited thereto. Incidentally, the weight average molecular weight (Mw) and the dispersity (Mw/Mn) were determined by gel permeation chromatography (GPC). The weight average molecular weight (Mw) represents a weight average molecular weight in terms of polystyrene determined by GPC.

The following are Fluoro-pendant diol compounds-1 to 5, Silicone-pendant diol compounds-1 to 6, Isocyanate compounds-1 and 2, and Hydroxy compounds-1 to 5 used for obtaining a polymer compound for forming a stretchable film.

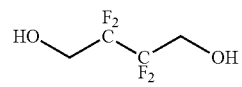

Fluoro-pendant diol compound-1

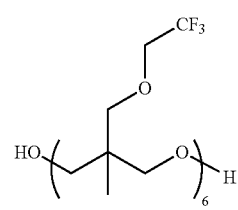

Fluoro-pendant diol compound-2

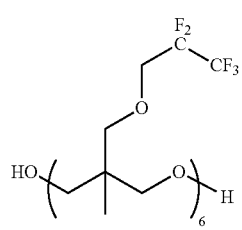

Fluoro-pendant diol compound-3

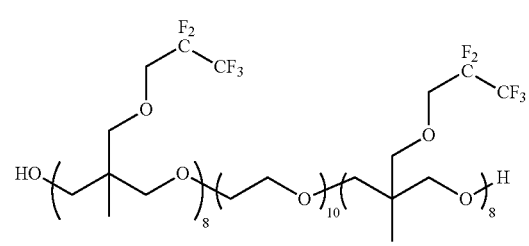

Fluoro-pendant diol compound-4

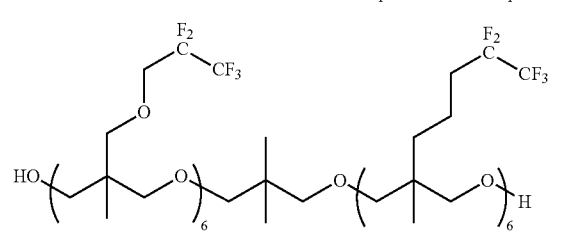

Fluoro-pendant diol compound-5

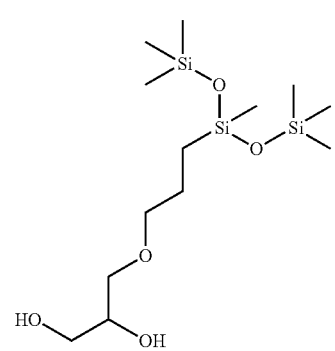

Silicone-pendant diol compound-1

-continued

Silicone-pendant diol compound-2

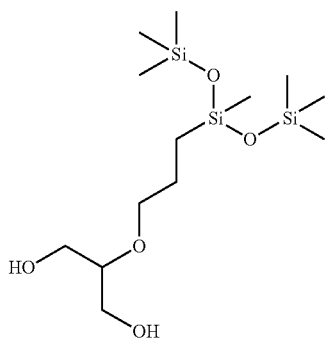

Silicone-pendant diol compound-3

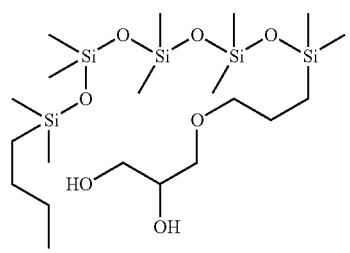

Silicone-pendant diol compound-4

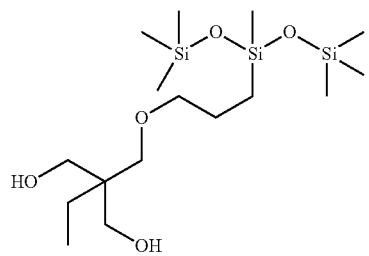

Silicone-pendant diol compound-5

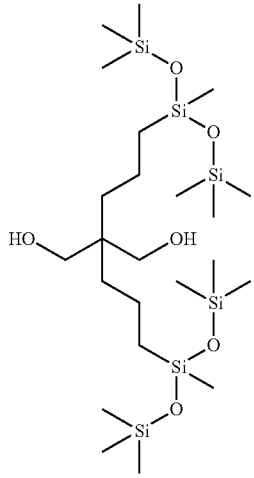

-continued

Silicone-pendant diol compound-6

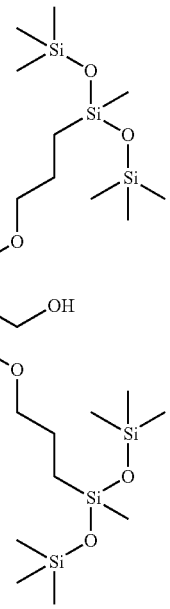

Isocyanete compound-1

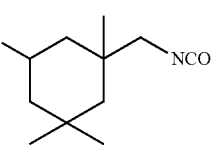

Isocyanete compound-2

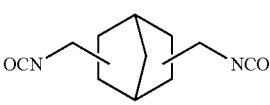

Hydroxy compound-1

134 in average

Hydroxy compound-2

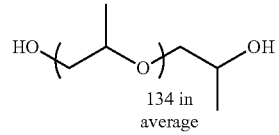

19 in average

Hydroxy compound-3

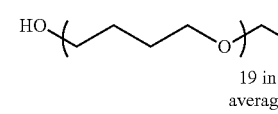

7 in average

Hydroxy compound-4

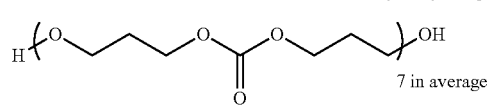

20 in average

Hydroxy compound-5

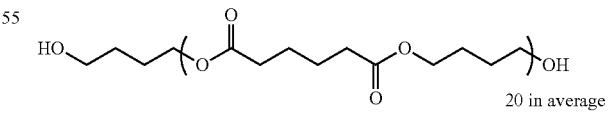

20 in average

In the formulae, the number of repeating units each represent the average value.

Synthesis Example of Silicone-Pendant Urethane-(Meth)Acrylate Blended as a Compound Having (Meth)Acrylate Group at the Terminal A mixture of 0.5 mol of Hydroxy compound-1, 0.5 mol of Hydroxy compound-2, 0.5 mol of Fluoro-pendant diol compound-1, and 0.5 mol of Silicone-pendant diol compound-1 was heated at 60° C. to remove water by vacuum drying. To this, 0.5 mol of Isocyanate compound-1 and 0.01 mol of dibutyltin dilaurate were added to perform the reaction at 60° C. for 3 hours with stirring, and 2 mol of hydroxyethyl acrylate was added to perform the reaction at 60° C. for 3 hours with stirring to give Fluorosilicone-pendant urethane-(meth)acrylate-1. The obtained polymer was measured for $^{13}$C-NMR, $^{1}$H-NMR, and GPC to give following analytical results.

In the same way as described above except for changing the combination of Fluoro-pendant diol compounds-1 to 5, Silicone-pendant diol compounds-1 to 6, Isocyanate compounds-1 and 2, and Hydroxy compounds-1 to 3, each of Fluorosilicone-pendant urethane-(meth)acrylates-2 to 11 and Comparative urethane-(meth)acrylates-1 to 3 was synthesized as a compound having (meth)acrylate groups at the terminals. The obtained polymers are shown below.

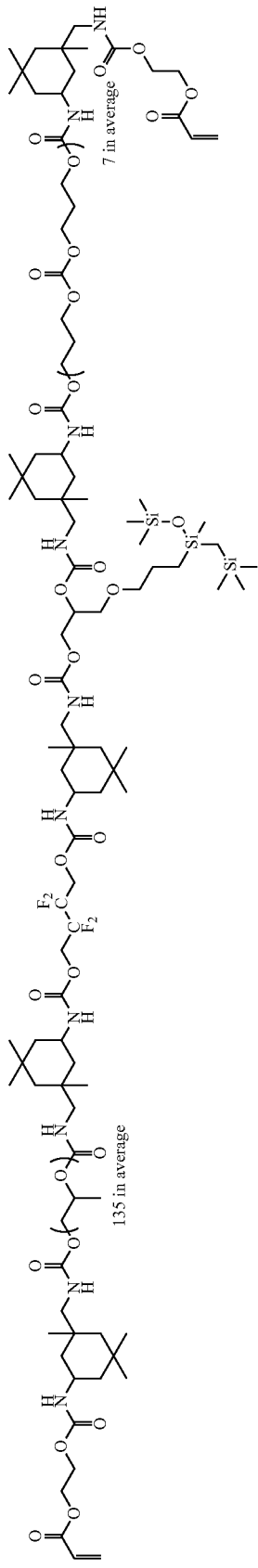
Fluorosilicone-pendant urethane-(meth)acrylate-1
Mw15200 Mw/Mn3.05
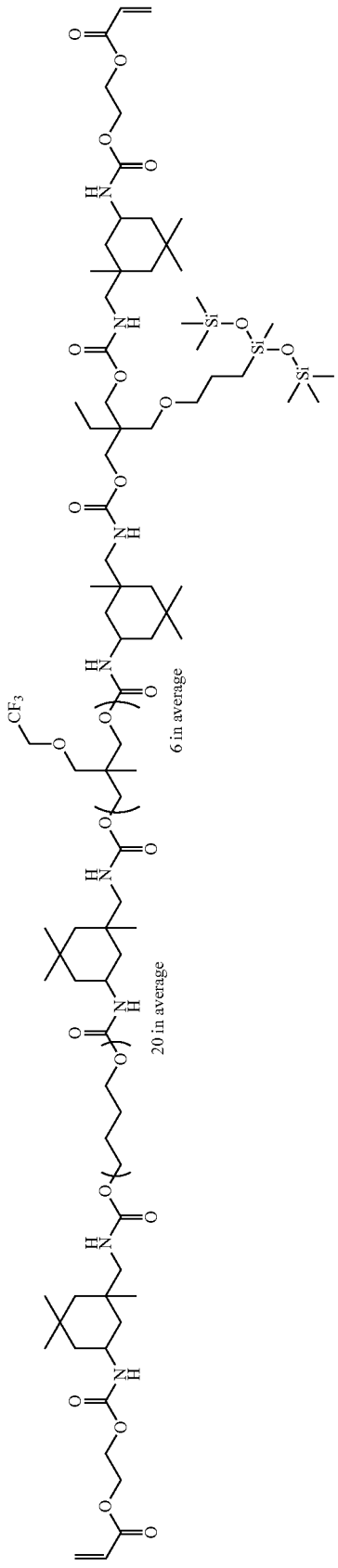
Fluorosilicone-pendant urethane-(meth)acrylate-2
Mw8200 Mw/Mn2.35

-continued
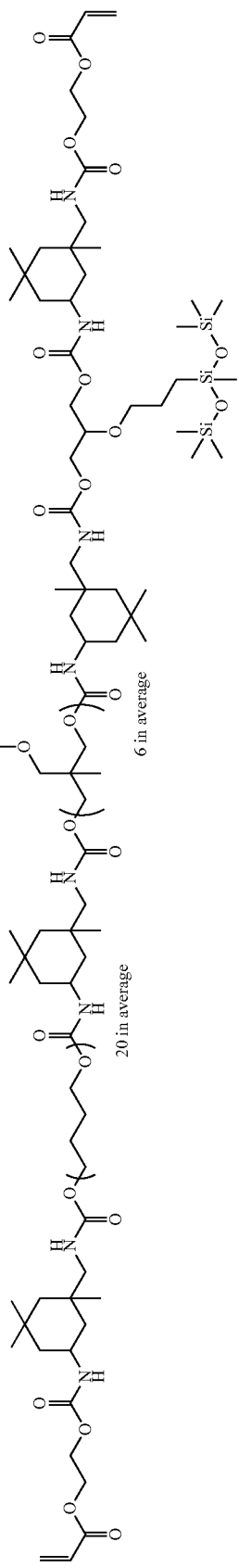
Fluorosilicone-pendant urethane-(meth)acrylate-3
Mw8400 Mw/Mn2.30
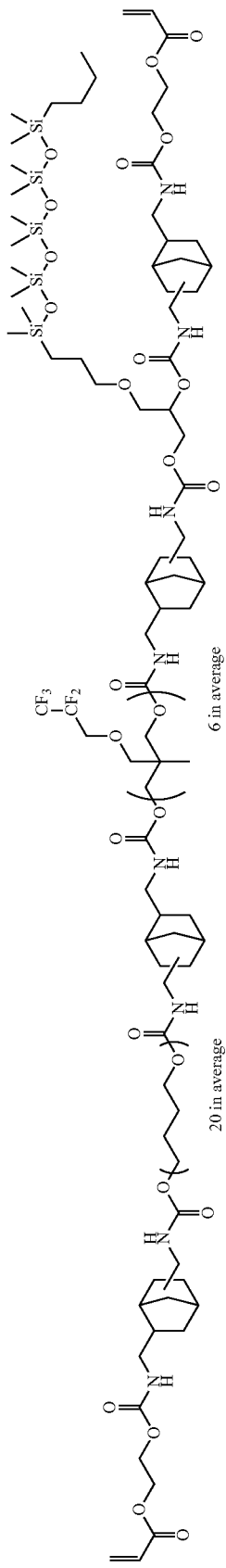
Fluorosilicone-pendant urethane-(meth)acrylate-4
Mw8900 Mw/Mn2.22

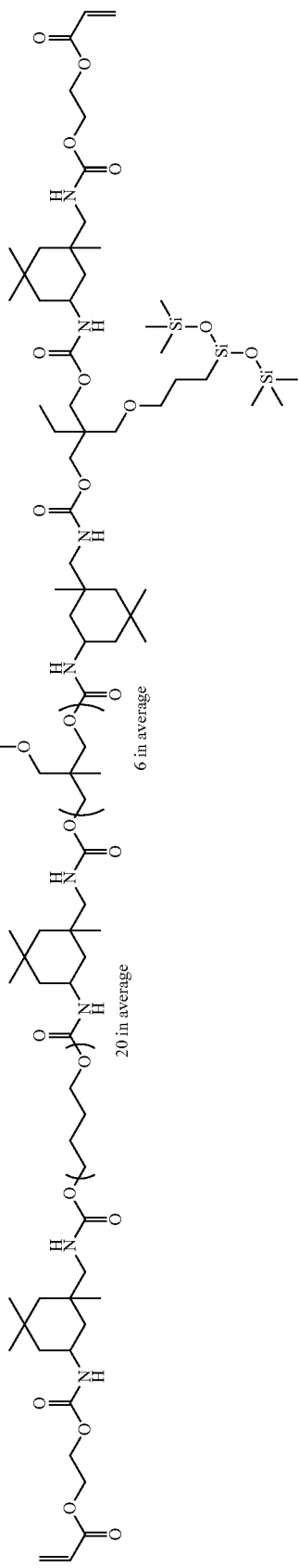
Fluorosilicone-pendant urethane-(meth)acrylate-5
Mw8200 Mw/Mn2.41
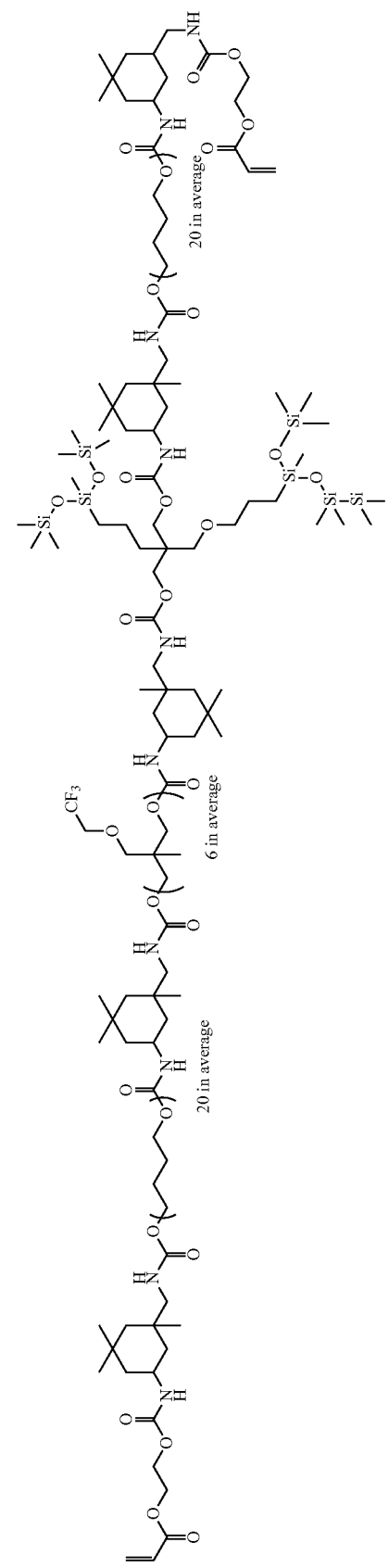
Fluorosilicone-pendant urethane-(meth)acrylate-6
Mw9010 Mw/Mn2.01

-continued
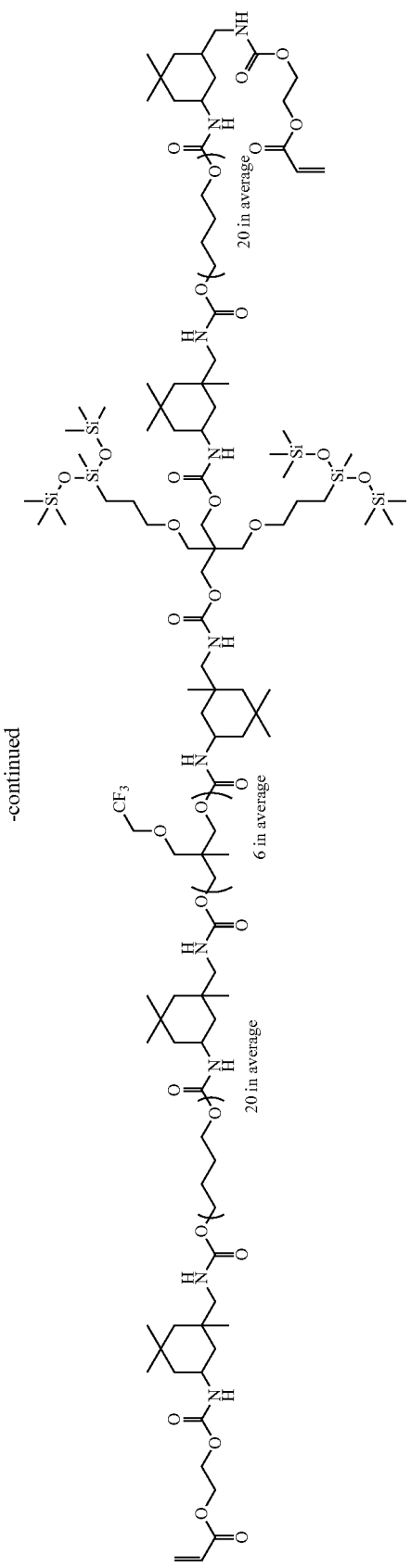
Fluorosilicone-pendant urethane-(meth)acrylate-7
Mw9600 Mw/Mn2.05
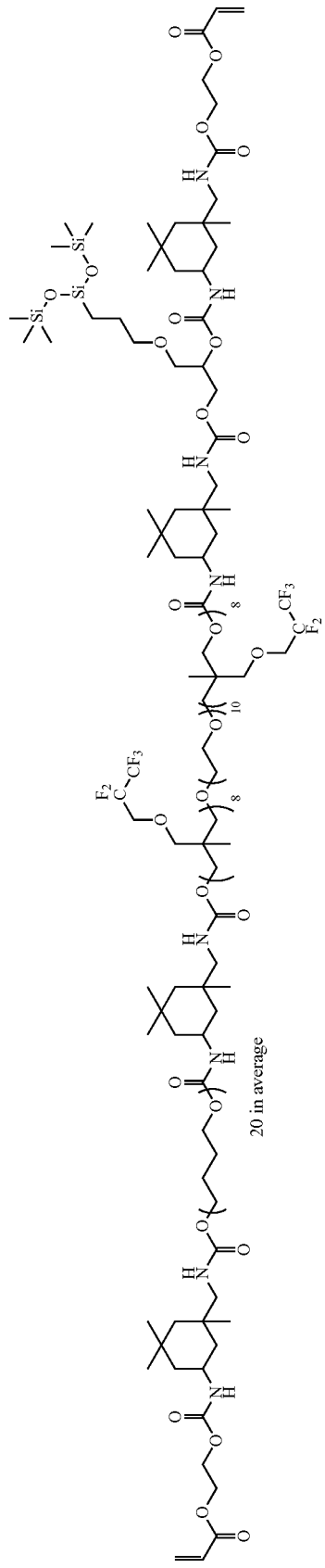
Fluorosilicone-pendant urethane-(meth)acrylate-8
Mw9600 Mw/Mn2.55

-continued
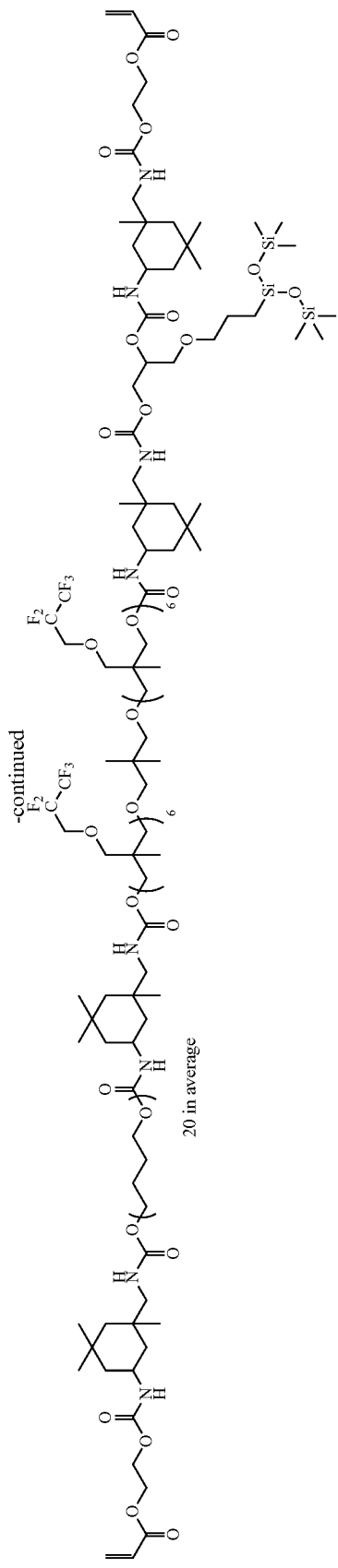
Fluorosilicone-pendant urethane-(meth)acrylate-9
Mw8700 Mw/Mn2.25
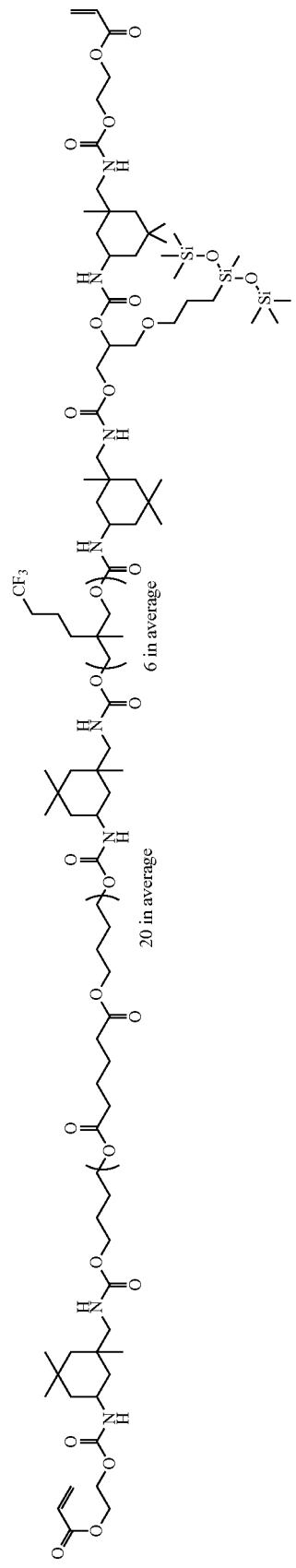
Fluorosilicone-pendant urethane-(meth)acrylate-10
Mw12200 Mw/Mn2.56

-continued
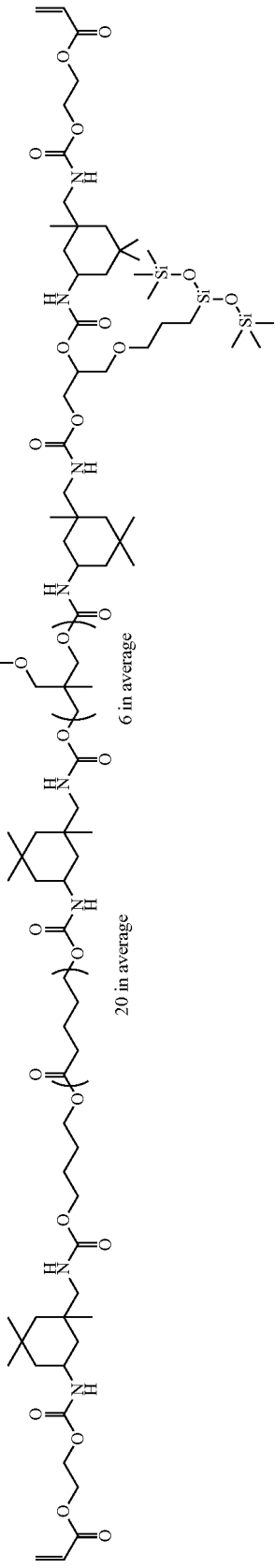
Fluorosilicone-pendant urethane-(meth)acrylate-11
Mw 16800 Mw/Mn 2.87
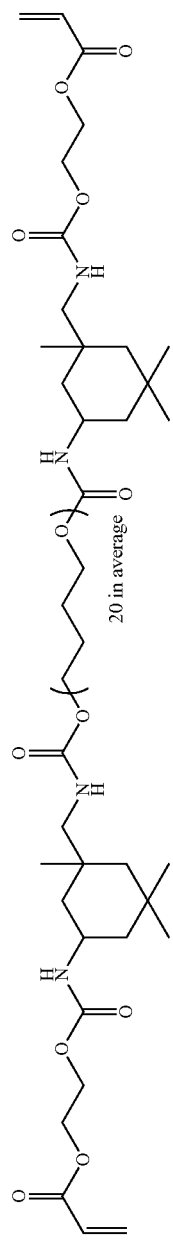
Comparative urethane-(meth)acrylate-1
Mw 7800 Mw/Mn 2.30

-continued
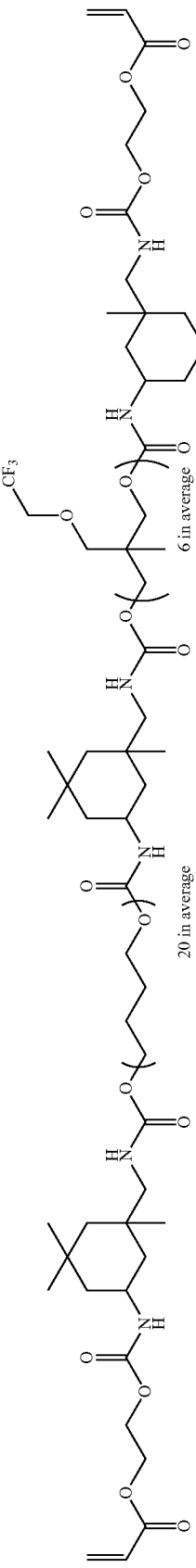
Comparative urethane-(meth)acrylate-2
Mw8600 Mw/Mn2.33
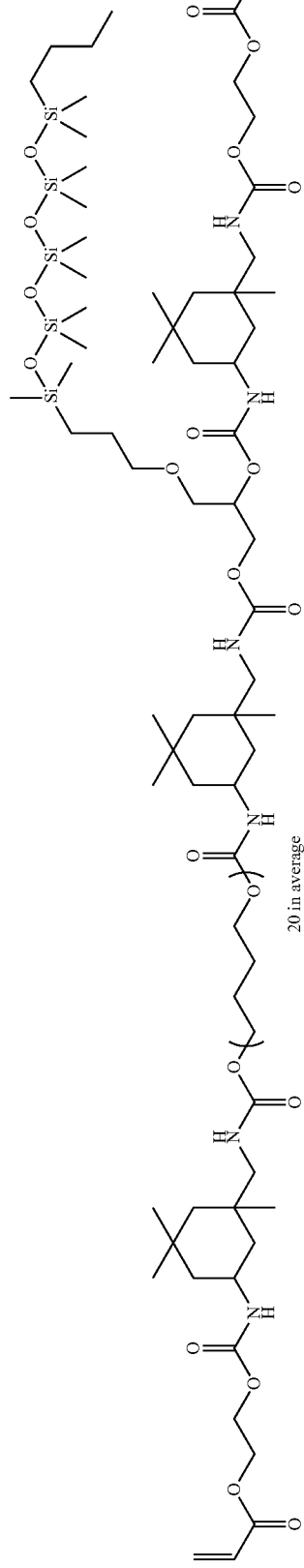
Comparative urethane-(meth)acrylate-3
Mw8900 Mw/Mn2.29

The following are Photo-radical generators-1 to 3 as well as Thermal-radical generators-1 and 2 blended to compositions for forming a stretchable film as an additive.
Photo-radical generator-1: 2,4,6-trimethylbenzoyl-diphenylphosphine oxide
Photo-radical generator-2: 2,2-dimethoxy-2-phenylacetophenone
Photo-radical generator-3: (±)-camphorquinone Thermal-radical generator-1: dimethyl 2,2'-azobis(2-methylpropionate)
Thermal-radical generator-2: 2,2'-azobisisobutyronitrile (AIBN)
The following is an organic solvent blended to compositions for forming a stretchable film.
Organic solvent: propylene glycol monomethyl ether acetate (PGMEA)

Examples and Comparative Examples

Each composition for forming a stretchable film (Stretchable film materials-1 to 14, Comparative stretchable film materials-1 to 3) was prepared by mixing a compound having (meth)acrylate groups at the terminals, Photo-radical generators-1 to 3, Thermal-radical generators-1 and 2, and an organic solvent in accordance with needs, in the composition described in Table 1. The prepared composition (material) for forming a stretchable film was applied onto a polyethylene substrate by bar coating method. In cases of Stretchable film materials-1 to 10, 13, and 14 as well as Comparative stretchable film materials-1 to 3, the coated film of each composition was cured by irradiation with 500 mJ/cm$^2$ of light using a 1,000 W xenon lamp in a nitrogen atmosphere to produce a stretchable film (Films-1 to 10, 13, and 14; Comparative Films-1 to 3). In cases of Stretchable film materials-11 and 12, each prepared composition for forming a stretchable film was applied onto a polyethylene substrate by bar coating method, followed by baking at 120° C. for 20 minutes in a nitrogen atmosphere to produce a stretchable film (Films-1 and 12).

TABLE 1

| Stretchable film material | Fluorosilicone-pendant urethane-(meth)acrylate (parts by mass) | Additive (parts by mass) |
|---|---|---|
| Stretchable film material 1 | Fluorosilicone-pendant urethane-(meth)acrylate-1 (70) isobornyl acrylate (30) | Photo-radical generator-1 (1) |
| Stretchable film material 2 | Fluorosilicone-pendant urethane-(meth)acrylate-2 (70) isobornyl acrylate (30) | Photo-radical generator-2 (2) |
| Stretchable film material 3 | Fluorosilicone-pendant urethane-(meth)acrylate-3 (70) isobornyl acrylate (30) | Photo-radical generator-3 (2) |
| Stretchable film material 4 | Fluorosilicone-pendant urethane-(meth)acrylate-4 (70) isobornyl acrylate (30) | Photo-radical generator-1 (1) |
| Stretchable film material 5 | Fluorosilicone-pendant urethane-(meth)acrylate-5 (70) isobornyl acrylate (30) | Photo-radical generator-1 (1) |
| Stretchable film material 6 | Fluorosilicone-pendant urethane-(meth)acrylate-6 (70) isobornyl acrylate (30) | Photo-radical generator-1 (1) |
| Stretchable film material 7 | Fluorosilicone-pendant urethane-(meth)acrylate-7 (70) isobornyl acrylate (30) | Photo-radical generator-1 (1) |
| Stretchable film material 8 | Fluorosilicone-pendant urethane-(meth)acrylate-8 (70) isobornyl acrylate (30) | Photo-radical generator-1 (1) |
| Stretchable film material 9 | Fluorosilicone-pendant urethane-(meth)acrylate-9 (70) isobornyl acrylate (30) | Photo-radical generator-1 (1) |
| Stretchable film material 10 | Fluorosilicone-pendant urethane-(meth)acrylate-1 (30) Fluorosilicone-pendant urethane-(meth)acrylate-4 (40) isobornyl acrylate (30) | Photo-radical generator-1 (1) |
| Stretchable film material 11 | Fluorosilicone-pendant urethane-(meth)acrylate-1 (80) Fluorosilicone-pendant urethane-(meth)acrylate-8 (20) PEGMEA (20) | Thermal-radical generator-1 (3) |
| Stretchable film material 12 | Fluorosilicone-pendant urethane-(meth)acrylate-1 (100) PEGMEA (20) | Thermal-radical generator-2 (3) |
| Stretchable film material 13 | Fluorosilicone-pendant urethane-(meth)acrylate-10 (70) isobornyl acrylate (30) | Photo-radical generator-1 (1) |
| Stretchable film material 14 | Fluorosilicone-pendant urethane-(meth)acrylate-11 (70) isobornyl acrylate (30) | Photo-radical generator-1 (1) |
| Comparative stretchable film material 1 | Comparative urethane-(meth)acrylate-1 (70) isobornyl acrylate (30) | Photo-radical generator-1 (1) |
| Comparative stretchable film material 2 | Comparative urethane-(meth)acrylate-2 (70) isobornyl acrylate (30) | Photo-radical generator-1 (1) |
| Comparative stretchable film material 3 | Comparative urethane-(meth)acrylate-3 (70) isobornyl acrylate (30) | Photo-radical generator-1 (1) |

(Measurement of Film Thickness, Contact Angle, Stretching Property, and Strength)

Each of the cured stretchable films was measured for film thickness and contact angle with water on the surface. After measuring the contact angle with water on the surface of the stretchable film, the stretchable film was peeled from the substrate, and subjected to measurement of the stretching property (elongation) and strength in conformity to JIS K6251. The results are shown in Table 2.

TABLE 2

| | Stretchable film | Stretchable film material | Film thickness (μm) | Contact angle (°) | Elongation (%) | Strength (MPa) |
|---|---|---|---|---|---|---|
| Example 1 | Film 1 | Stretchable film material 1 | 310 | 118 | 410 | 13.1 |
| Example 2 | Film 2 | Stretchable film material 2 | 320 | 122 | 390 | 12.1 |
| Example 3 | Film 3 | Stretchable film material 3 | 360 | 125 | 420 | 14.6 |
| Example 4 | Film 4 | Stretchable film material 4 | 350 | 128 | 330 | 11.0 |
| Example 5 | Film 5 | Stretchable film material 5 | 360 | 124 | 430 | 14.1 |
| Example 6 | Film 6 | Stretchable film material 6 | 340 | 119 | 330 | 11.3 |
| Example 7 | Film 7 | Stretchable film material 7 | 330 | 118 | 410 | 13.0 |
| Example 8 | Film 8 | Stretchable film material 8 | 380 | 121 | 490 | 10.4 |
| Example 9 | Film 9 | Stretchable film material 9 | 370 | 122 | 350 | 11.0 |
| Example 10 | Film 10 | Stretchable film material 10 | 370 | 123 | 360 | 11.8 |
| Example 11 | Film 11 | Stretchable film material 11 | 230 | 124 | 320 | 11.7 |
| Example 12 | Film 12 | Stretchable film material 12 | 240 | 125 | 330 | 12.1 |
| Example 13 | Film 13 | Stretchable film material 13 | 310 | 125 | 410 | 18.1 |
| Example 14 | Film 14 | Stretchable film material 14 | 300 | 122 | 390 | 17.3 |
| Comparative Example 1 | Comparative Film 1 | Comparative stretchable film material 1 | 300 | 70 | 350 | 15.3 |
| Comparative Example 2 | Comparative Film 2 | Comparative stretchable film material 2 | 330 | 99 | 310 | 8.1 |
| Comparative Example 3 | Comparative Film 3 | Comparative stretchable film material 3 | 330 | 94 | 390 | 12.1 |

As shown in Table 2, the stretchable films in Examples 1 to 14, using polyurethane having both pendants of fluorine and silicone, gave very high contact angle with water, that is, showed very high water repellency, together with excellent stretching property and strength.

On the other hand, the stretchable films in Comparative Examples 1 to 3, having no fluorine nor silicone, only fluorine, or only silicone pendant, showed lower water repellency compared to those of Examples.

From the above, it was revealed that the inventive stretchable film has excellent stretching property and strength, together with excellent water repellency on the film surface, and has excellent properties as a film to cover stretchable wiring used for a wearable device and so on thereby.

It is to be noted that the present invention is not restricted to the foregoing embodiment. The embodiment is just an exemplification, and any examples that have substantially the same feature and demonstrate the same functions and effects as those in the technical concept described in claims of the present invention are included in the technical scope of the present invention.

The invention claimed is:

1. A stretchable film of a cured product of a resin comprising a polymer compound having a urethane bond in a main chain thereof, a repeating unit containing a fluorine atom, and a repeating unit containing a silicon atom, wherein the polymer compound is a compound having a (meth)acrylate group at a terminal thereof, shown by the following general formula (3):

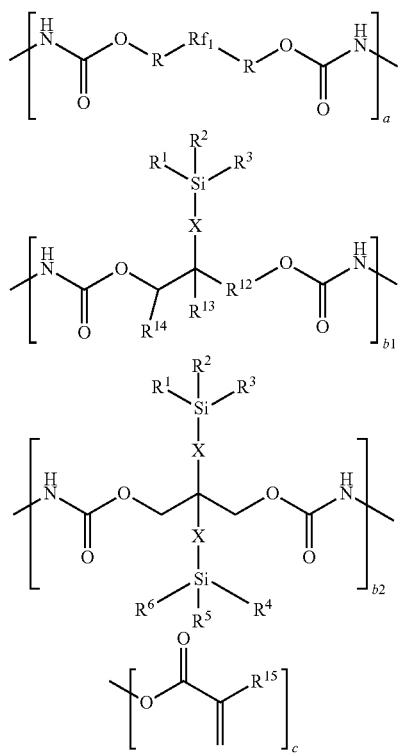

(3)

wherein $R^1$, $R^2$, $R^3$, $R^4$, $R^5$, and $R^6$ each represent a linear, branched, or cyclic alkyl group having 1 to 6 carbon atoms, a phenyl group, a 3,3,3-trifluoropropyl group, or a —$(OSiR^7R^8)_n$—$OSiR^9R^{10}R^{11}$ group; $R^7$, $R^8$, $R^9$, $R^{10}$, and $R^{11}$ each have the same meaning as $R^1$ to $R^6$; each R independently represents a single bond or a methylene group; "n" represents a number in a range of 0 to 100; $R^{12}$ represents a single bond, a methylene group, or an ethylene group; $R^{13}$ represents a hydrogen atom or a linear alkyl group having 1 to 4 carbon atoms; $R^{14}$ represents a hydrogen atom or a methyl group; X represents a linear or branched alkylene group having 3 to 7 carbon atoms, optionally containing an ether group; $Rf_1$ represents a linear or branched alkylene group having 1 to 200 carbon atoms and at least one fluorine atom, optionally containing an ether group; $R^{15}$ represents a hydrogen atom or a methyl group; and "a", "b1", "b2", and "c" are each number of units in one molecule and are integers in ranges of $1 \leq a \leq 20$, $0 \leq b1 \leq 20$, $0 \leq b2 \leq 20$, $1 \leq b1+b2 \leq 20$, and $1 \leq c \leq 4$.

2. The stretchable film according to claim 1, wherein the polymer compound has a weight average molecular weight of 500 or more.

3. The stretchable film according to claim 1, wherein the stretchable film exhibits a stretching property of 40 to 1000% in a tensile test regulated by JIS K6251.

4. The stretchable film according to claim 1, wherein the stretchable film is used as a film to be in contact with a conductive wiring having stretchability.

5. A stretchable film of a cured product of a resin comprising a polymer compound having a urethane bond in a main chain thereof, a repeating unit containing a fluorine atom, and a repeating unit containing a silicon atom, wherein the polymer compound is a compound having a (meth)acrylate group at a terminal thereof, shown by the following general formula (3):

(3)

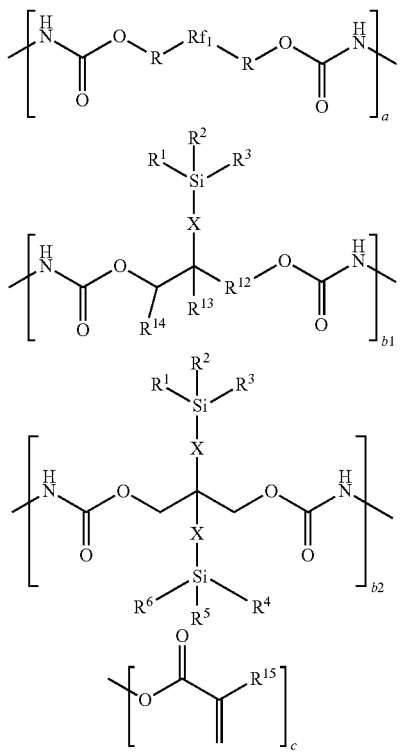

wherein $R^1$, $R^2$, $R^3$, $R^4$, $R^5$, and $R^6$ each represent a linear, branched, or cyclic alkyl group having 1 to 6 carbon atoms, a phenyl group, a 3,3,3-trifluoropropyl group, or a —$(OSiR^7R^8)_n$—$OSiR^9R^{10}R^{11}$ group; $R^7$, $R^8$, $R^9$, $R^{10}$, and $R^{11}$ each have the same meaning as $R^1$ to $R^6$; each R independently represents a single bond or a methylene group; "n" represents a number in a range of 0 to 100; $R^{12}$ represents a single bond, a methylene group, or an ethylene group; $R^{13}$ represents a hydrogen atom or a linear alkyl group having 1 to 4 carbon atoms; $R^{14}$ represents a hydrogen atom or a methyl group; X represents a linear or branched alkylene group having 3 to 7 carbon atoms, optionally containing an ether group; $Rf_1$ represents a linear or branched alkylene group having 1 to 200 carbon atoms and at least one fluorine atom, optionally containing an ether group; $R^{15}$ represents a hydrogen atom or a methyl group; and "a", "b1", "b2", and "c" are each number of units in one molecule and are integers in ranges of $1 \leq a \leq 20$, $0 \leq b1 \leq 20$, $0 \leq b2 \leq 20$, $1 \leq b1+b2 \leq 20$, and $1 \leq c \leq 4$, and wherein the polymer compound is derived in part from a reaction product of a diol compound and a compound having an isocyanate group, and the diol compound contains a diol compound Ma as well as a diol compound Mb1 and/or a diol compound Mb2 shown by the following general formulae (2):

(2)

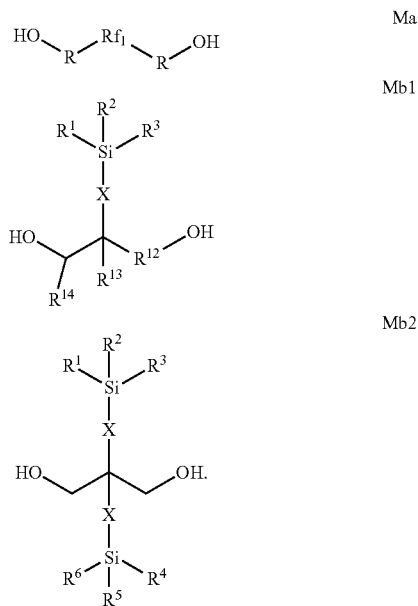

6. The stretchable film according to claim 5, wherein the polymer compound has a weight average molecular weight of 500 or more.

7. The stretchable film according to claim 5, wherein the stretchable film exhibits a stretching property of 40 to 1000% in a tensile test regulated by JIS K6251.

8. The stretchable film according to claim 5, wherein the stretchable film is used as a film to be in contact with a conductive wiring having stretchability.

9. A method for forming a stretchable film according to claim 5, comprising:
mixing a diol compound containing a diol compound Ma as well as a diol compound Mb1 and/or a diol compound Mb2, together with a compound having an isocyanate group, to form a mixture, and adding a (meth)acrylate to the mixture;
forming a film from the mixture; and
curing the film by heating.

10. A method for forming a stretchable film according to claim 1, comprising:
forming a film of the resin comprising a polymer compound having a (meth)acrylate group at a terminal thereof; and
curing the film by heating and/or light irradiation.

* * * * *